United States Patent
Chen et al.

(10) Patent No.: US 9,163,003 B2
(45) Date of Patent: Oct. 20, 2015

(54) 4-PIPERIDINYL COMPOUNDS FOR USE AS TANKYRASE INHIBITORS

(75) Inventors: Christine Hiu-Tung Chen, Cambridge, MA (US); Donovan Noel Chin, Cambridge, MA (US); Lucien V. DiPietro, Cambridge, MA (US); Jianmei Fan, Cambridge, MA (US); Mark G. Palermo, Cambridge, MA (US); Michael David Shultz, Cambridge, MA (US); Bakary-Barry Toure, Cambridge, MA (US)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 14/154,173

(22) PCT Filed: Jul. 13, 2012

(86) PCT No.: PCT/IB2012/053613
§ 371 (c)(1),
(2), (4) Date: May 27, 2014

(87) PCT Pub. No.: WO2013/008217
PCT Pub. Date: Jan. 17, 2013

(65) Prior Publication Data
US 2015/0126513 A1  May 7, 2015

Related U.S. Application Data

(60) Provisional application No. 61/507,321, filed on Jul. 13, 2011.

(51) Int. Cl.
| | |
|---|---|
| C07D 491/052 | (2006.01) |
| C07D 493/04 | (2006.01) |
| C07D 401/12 | (2006.01) |
| C07D 401/04 | (2006.01) |
| C07D 401/14 | (2006.01) |
| C07D 471/04 | (2006.01) |
| C07D 487/04 | (2006.01) |
| C07D 491/04 | (2006.01) |
| C07D 495/04 | (2006.01) |
| C07D 498/04 | (2006.01) |
| C07D 513/04 | (2006.01) |

(52) U.S. Cl.
CPC ............ *C07D 401/04* (2013.01); *C07D 401/14* (2013.01); *C07D 471/04* (2013.01); *C07D 487/04* (2013.01); *C07D 491/04* (2013.01); *C07D 491/052* (2013.01); *C07D 495/04* (2013.01); *C07D 498/04* (2013.01); *C07D 513/04* (2013.01)

(58) Field of Classification Search
None
See application file for complete search history.

(56) References Cited

U.S. PATENT DOCUMENTS

| | | | |
|---|---|---|---|
| 2004/0132718 A1* | 7/2004 | Jacobson et al. | 514/217.04 |
| 2005/0075347 A1 | 4/2005 | Albrecht et al. | |
| 2005/0085476 A1 | 4/2005 | Seko et al. | |
| 2005/0159431 A1 | 7/2005 | Albrecht et al. | |
| 2008/0269234 A1 | 10/2008 | Gandhi et al. | |
| 2009/0163545 A1 | 6/2009 | Goldfarb | |

FOREIGN PATENT DOCUMENTS

| | | |
|---|---|---|
| EP | 1 142 881 A1 | 10/2001 |
| EP | 1 396 488 A1 | 3/2004 |
| WO | 99/11624 A1 | 3/1999 |
| WO | 02/48117 A1 | 6/2002 |
| WO | 02/094790 A1 | 11/2002 |
| WO | 03/049678 A2 | 6/2003 |
| WO | 03/063874 A1 | 8/2003 |
| WO | 03/080581 A1 | 10/2003 |
| WO | 2004/087677 A2 | 10/2004 |
| WO | 2004/111014 A1 | 12/2004 |
| WO | 2005/018557 A2 | 3/2005 |
| WO | 2005/061460 A1 | 7/2005 |
| WO | 2006/003146 A1 | 1/2006 |
| WO | 2006/004925 A1 | 1/2006 |
| WO | 2007/002701 A2 | 1/2007 |
| WO | 2007/127726 A2 | 11/2007 |
| WO | 2009/059994 A2 | 5/2009 |

(Continued)

OTHER PUBLICATIONS

Bae et al., Tankyrase 1 interacts with Mcl-1 proteins and inhibits their regulation of apoptosis. J Biol Chem. Feb. 14, 2003;278(7):5195-204. Epub Dec. 9, 2002.

(Continued)

*Primary Examiner* — Timothy R Rozof
(74) *Attorney, Agent, or Firm* — Qian Zhang

(57) ABSTRACT

The present invention provides for compounds of formula (I):

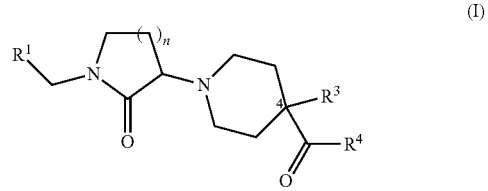

(I)

wherein $R^1$-$R^4$ and n are defined herein. The present invention also provides for pharmaceutical compositions and combinations comprising a compound of formula (I) as well as for the use of such compounds as tankyrase inhibitors and in the treatment of Wnt signaling and tankyrase 1 and 2 signaling related disorders which include, but are not limited to, cancer.

20 Claims, No Drawings

(56) References Cited

FOREIGN PATENT DOCUMENTS

WO 2009/061131 A2 5/2009
WO 2009/118382 A1 10/2009

OTHER PUBLICATIONS

Barker et al., Mining the Wnt pathway for cancer therapeutics. Nat Rev Drug Discov. Dec. 2006;5(12):997-1014. Review.
Behrens et al., Functional interaction of an axin homolog, conductin, with beta-catenin, APC, and GSK3beta. Science. Apr. 24, 1998;280(5363):596-9.
Chang et al., Poly(ADP-ribose) is required for spindle assembly and structure. Nature. Dec. 2, 2004;432(7017):645-9.
Chang et al., NuMA is a major acceptor of poly(ADP-ribosyl)ation by tankyrase 1 in mitosis. Biochem J. Oct. 15, 2005;391(Pt 2):177-84.
Chi et al., Tankyrase is a golgi-associated mitogen-activated protein kinase substrate that interacts with IRAP in GLUT4 vesicles. J Biol Chem. Dec. 8, 2000;275(49):38437-44.
Clevers, Wnt/beta-catenin signaling in development and disease. Cell. Nov. 3, 2006;127(3):469-80.
Cook et al., Role for the related poly(ADP-Ribose) polymerases tankyrase 1 and 2 at human telomeres. Mol Cell Biol. Jan. 2002;22(1):332-42.
Dynek et al., Resolution of sister telomere association is required for progression through mitosis. Science. Apr. 2, 2004;304(5667):97-100.
Fancy et al., Axing as regulatory and therapeutic target in newborn brain injury and remyelination.
Nat Neurosci. Jun. 26, 2011;14(8):1009-16.
Hahn et al. Inhibition of telomerase limits the growth of human cancer cells. Nat Med. 1999;5(10):1164-70.
Hart et al., Downregulation of beta-catenin by human Axin and its association with the APC tumor suppressor, beta-catenin and GSK3 beta. Curr Biol. May 7, 1998;8(10):573-81.
Huang et al., Tankyrase inhibition stabilizes axin and antagonizes Wnt signalling. Nature. Oct. 1, 2009;461(7264):614-20.
Kishida et al., Axin prevents Wnt-3a-induced accumulation of beta-catenin. Oncogene. Jan. 28, 1999;18(4):979-85.
Kwon et al., Mechanisms to suppress multipolar divisions in cancer cells with extra centrosomes. Genes Dev. Aug. 15, 2008;22(16):2189-203.

Lammi et al., Mutations in AXIN2 cause familial tooth agenesis and predispose to colorectal cancer. Am J Hum Genet. May 2004;74(5):1043-50. Epub Mar. 23, 2004.
Lee et al., The roles of APC and Axin derived from experimental and theoretical analysis of the Wnt pathway. PLoS Biol. Oct. 2003;1(1):E10. Epub Oct. 13, 2003.
Li et al., Herpes simplex virus requires poly(Adp-ribose) polymerase activity for efficient replication and induces extracellular signal-related kinase-dependent phosphorylation and ICP0-dependent nuclear localization of tankyrase 1. J Virol. Jan. 2012;86(1):492-503. Epub Oct. 19, 2011.
Liu et al., Efficient total synthesis of (S)-14-azacamptothecin. Chem Asian J. Jun. 1, 2010;5(6):1382-8.
Liu et al., Mutations in AXIN2 cause colorectal cancer with defective mismatch repair by activating beta-catenin/TCF signalling. Nat Genet. Oct. 2000;26(2):146-7.
Miyaki et al., Characteristics of somatic mutation of the adenomatous polyposis coli gene in colorectal tumors. Cancer Res. Jun. 1, 1994;54(11):3011-20.
Miyoshi et al., Somatic mutations of the APC gene in colorectal tumors: mutation cluster region in the APC gene. Hum Mol Genet. Jul. 1992;1(4):229-33.
Polakis, The many ways of Wnt in cancer. Curr Opin Genet Dev. Feb. 2007;17(1):45-51.
Powell et al., APC mutations occur early during colorectal tumorigenesis. Nature. Sep. 17, 1992;359(6392):235-7.
Salic et al., Control of beta-catenin stability: reconstitution of the cytoplasmic steps of the wnt pathway in *Xenopus* egg extracts. Mol Cell. Mar. 2000;5(3):523-32.
Seimiya et al., Tankyrase 1 as a target for telomere-directed molecular cancer therapeutics. Cancer Cell. Jan. 2005;7(1):25-37.
Smith et al., Tankyrase, a poly(ADP-ribose) polymerase at human telomeres. Science. Nov. 20, 1998;282(5393):1484-7.
Taniguchi et al., Mutational spectrum of beta-catenin, AXIN1, and AXIN2 in hepatocellular carcinomas and hepatoblastomas. Oncogene. Jul. 18, 2002;21(31):4863-71.
Ulsamer et al., Axin pathway activity regulates in vivo pY654-β-catenin accumulation and pulmonary fibrosis. J Biol Chem. Feb. 10, 2012;287(7):5164-72.
Yeh et al., Hypermetabolism, hyperphagia, and reduced adiposity in tankyrase-deficient mice. Diabetes. Nov. 2009;58(11):2476-85.

* cited by examiner

4-PIPERIDINYL COMPOUNDS FOR USE AS TANKYRASE INHIBITORS

FIELD OF THE INVENTION

The present invention relates to novel 4-piperidinyl compounds, pharmaceutical compositions containing them, and the use of such compounds as tankyrase inhibitors and in the treatment of Wnt signaling and tankyrase 1 and 2 signaling related disorders which include, but are not limited to, cancer.

BACKGROUND OF THE INVENTION

The evolutionarily conserved canonical Wnt/β-catenin signal transduction cascade controls many aspects of metazoan development. Context-dependent activation of the pathway is involved in embryonic cell fate decisions, stem cell regulation and tissue homeostasis (Clevers, H. Cell 2006, 127, 469-80).

A key feature of the Wnt/β-catenin pathway is the regulated proteolysis of the downstream effector β-catenin by the β-catenin destruction complex. The principal constituents of the β-catenin destruction complex are adenomatous polyposis coli (APC), Axin, and GSK3α/β. In the absence of Wnt pathway activation, cytosolic β-catenin is constitutively phosphorylated and targeted for degradation. Upon Wnt stimulation, the β-catenin destruction complex disassociates, which leads to the accumulation of nuclear β-catenin and transcription of Wnt pathway responsive genes.

Inappropriate activation of the pathway, mediated by over expression of Wnt proteins or mutations affecting components of the β-catenin destruction complex, thus leading to stabilization of β-catenin, has been observed in many cancers. Notably, truncating mutations of the tumour suppressor APC are the most prevalent genetic alterations in colorectal carcinomas (Miyaki, M. et al. Cancer Res 1994, 54, 3011-20; Miyoshi, Y. et al. Hum Mol Genet 1992, 1, 229-33; and Powell, S. M. et al. Nature 1992, 359, 235-7). In addition, Axin1 and Axin2 mutations have been identified in patients with hepatocarcinomas and colorectal cancer respectively (Taniguchi, K. et al. Oncogene 2002, 21, 4863-71; Liu, W. et al. Nat Genet 2000, 26, 146-7; Lammi, L. et al. Am J Hum Genet 2004, 74, 1043-50). These somatic mutations result in Wnt-independent stabilization of β-catenin and constitutive activation of β-catenin-mediated transcription.

Deregulated Wnt pathway activity has also been implicated in many other cancers (Polakis, P. Curr Opin Genet Dev 2007, 17, 45-51; and Barker, N. et al. Nat Rev Drug Discov 2006, 5, 997-1014), including colorectal, melanoma, breast, liver, lung and gastric cancers. Other disorders associated with aberrant Wnt signaling include osteoporosis, osteoarthritis, polycystic kidney disease, pulmonary fibrosis, diabetes, schizophrenia, vascular disease, cardiac disease, non-oncogenic proliferative diseases, and neurodegenerative diseases such as Alzheimer's disease.

The efficient assembly of the multi-protein β-catenin destruction complex is dependent on the steady state levels of its principal constituents. Axin has been reported to be the concentration-limiting factor in regulating the efficiency of the β-catenin destruction complex (Salic, A., et al. Mol Cell 2000, 5, 523-32; and Lee, E. et al. PLoS Biol 2003, 1, E10) and increased expression of Axin can enhance β-catenin degradation in cell lines expressing truncated APC (Behrens, J. et al. Science 1998, 280, 596-9; Kishida, M. et al. Oncogene 1999, 18, 979-85; and Hart, M. J., et al. Curr Biol 1998, 8, 573-81). Thus, it is likely that Axin protein levels need to be tightly regulated to ensure proper Wnt pathway signaling.

It has recently been found that β-catenin degradation can be promoted by stablising Axin through the inhibition of the poly-ADP-ribose polymerase (PARP) enzymes tankyrase 1 and tankyrase 2, as explained in WO 2009/059994 and Huang et al., (Huang, S. M., et al. Nature 2009, 461, 614-620). Both tankyrase isoforms interact with a highly conserved domain of Axin and stimulate its degradation through the ubiquitin-proteasome pathway. This previously unknown mechanism for stabilising Axin protein, thereby enhancing β-catenin degradation, can be exploited for treating Wnt signaling-related disorders. Axin proteins are essential regulators of a spectrum of physiological processes, including brain oligodendrocyte progenitor cell differentiation for remyelination (Fancy, S., et al. Nature NeuroSci 2011, 14, 1009-1017), and epithelial-to-mesenchymal transition during pulmonary fibrosis (Ulsamer, A., et al. J Bio Chem 2012, 287, 5164-5172). Thus, by way of stabilizing Axin proteins, Tankyrase inhibitors could be used as a therapy for remyelination post brain injury and pulmonary fibrosis.

Tankyrase has several binding protein partners, including TRF1, a double-stranded telomeric repeat binding protein (Smith, S., et al. Science 1998, 282, 1484-1487); NuMA, an essential protein in mitotic spindle assembly (Chang, W., et al. Biochem J, 2005, 391, 177-184); IRAP, an integral membrane protein involved in glucose uptake in response to insulin (Chi, N. W., et al. J Biol Chem 2000, 275, 38437-38444); and Mcl-1, a pro-apoptotic protein (Bae, J., et al. J Biol Chem 2003, 278, 5195-5204).

By way of its various interacting proteins, tankyrase proteins have been implicated in different biological functions. Tankyrase poly (ADP-ribosyl)ates TRF1, releasing it from telomeres and enhancing telomere access to telomerase. Thus, tankyrase functions as a positive regulator for telomere elongation by telomerase, supported by the findings that long-term overexpression of tankyrase leads to telomere elongation (Cook, B. D., et al Mol Cell Biol 2002, 22, 332-242). Telomere maintenance by telomerase has been attributed to the uncontrolled proliferation of cancer cells (Hahn, W. C., et al, Nat Med 1999, 5, 1164-1169). Tankyrase could be a target for cancer therapy by inhibiting the telomere accessibility for telomerase. Tankyrase inhibition could be used as an effective cancer therapy to treat patients with a wide spectrum of cancers, including leukemia, lymphoma, multiple myeloma, lung, and breast cancer.

Tankyrase also plays a role in cell mitosis by: 1) poly(ADP-ribosyl)ating NuMA during mitosis and regulating its functions at spindle poles (Chang, W., et al. Biochem J 2005, 391, 177-184); 2) by regulating spindle assembly and structure (Chang, P., et al. Nature 2004, 432, 645-649); and 3) by maintaining sister chromatid resolution at telomeres (Dynek, J., et al. Science 2004, 304, 97-100). Inhibition of tankyrase leads to cell mitotic arrest or senescence, and thus could be exploited for treating diseases that have abnormal mitotic division, such as cancer. Examples include breast, lung, ovarian, leukemia, lymphoma, and melanoma. In addition, tankyrase 1 was identified as a gene required for centrosome clustering, a mechanism that cancer cells with supernumerary centrosomes employs to suppress multipolar mitosis and enable bipolar mitosis (Kwon, M., et al. Genes Dev 2008, 22, 2189-2203). Thus inhibition of tankyrase could be exploited for treating cancers with centrosome amplification, including both solid and haematological cancers, examples include breast, bladder, lung, colon, and leukemia.

Moreover, One of the cellular localizations of tankyrase is at the Golgi apparatus co-localizing with the glucose transporter GLUT4 vesicles where tankyrase is associated with IRAP, and tankyrase is implicated in the regulation of GLUT4 trafficking in adipocytes (Chi, N. W., et al. *J Biol Chem* 2000, 275, 38437-38444). Tankyrase-deficient mice exhibit reduced adiposity and increased energy expenditure by increases in both fatty acid oxidation and insulin-stimulated glucose utilization (Yeh, T., et al. *Diabetes* 2009). This supports tankyrase involvement in energy homeostasis in mammals and inhibiting tankyrase can be exploited for treating metabolic diseases, such as obesity.

Tankyrase has been repoted to be a host protein targeted by Herpes Simplex Virus (HSV), modulated by HSV through hyperphosphorylation, nuclear transport and proteasomal degradation (Li Z., et al. *J of Virol* 2012, 86, 492-503). More importantly, efficient HSV viral replication requires the enzymatic activity of tankyrase proteins. Inhibition of tankyrase activity by inhibitor XAV939 (WO 2009/059994, Huang, S. M., et al. *Nature* 2009, 461, 614-620) suppressed HSV viral protein expression and decreased viral growth. Thus, inhibition of tankyrase can be exploited as anti-viral therapeutics, including but not limited to treatment of HSV infection.

Consequently, compounds that inhibit tankyrase (TNKS) and/or Wnt Signaling may be useful for treatment of diseases mediated by such inhibitions.

SUMMARY OF THE INVENTION

The present invention provides for compounds of formula (I):

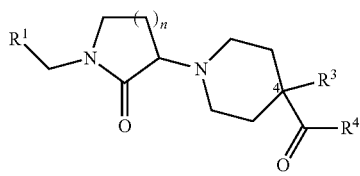

(I)

wherein $R^1$-$R^4$ and n are defined herein. The present invention also provides for pharmaceutical compositions and combinations comprising a compound of formula (I) as well as for the use of such compounds as tankyrase inhibitors and in the treatment of Wnt signaling and tankyrase 1 and 2 signaling related disorders which include, but are not limited to, cancer.

DETAILED DESCRIPTION OF THE INVENTION

The present invention provides for compounds of formula (I)

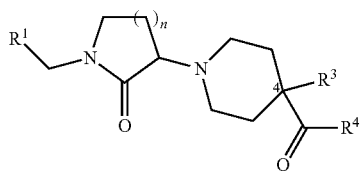

(I)

wherein:
$R^1$ is $R^2$ or $R^2$—NHC(O)—;
$R^2$ is phenyl optionally substituted with one or two substituents each independently selected from the group consisting of: halo, OH, CN, $NO_2$, $C_{1-6}$ alkyl, $C_{1-6}$ alkoxy, $C_{1-6}$ haloalkyl, $C(O)R^a$, $COOR^a$, $NR^aR^b$, $NHC(O)R^a$, and $C(O)NR^aR^b$;

or
$R^2$ is a 5 membered heteroaryl having one to four heteroatoms selected from the group consisting of N, O, and S, or $R^2$ is a 6 membered heteroaryl having one or two N,
said 5 and 6 membered heteroaryl rings being optionally substituted with one to three substituents each independently selected from the group consisting of: halo, oxo, OH, CN, $NO_2$, $C_{1-6}$ alkyl, $C_{1-6}$ alkoxy, $C_{1-6}$ haloalkyl, $C(O)R^a$, $COOR^a$, $NR^aR^b$, $NHC(O)R^a$, and $C(O)NR^aR^b$;
or
$R^2$ is an 8-10 membered bicyclic heteroaryl having 1 to 4 heteroatoms selected from the group consisting of N, O, and S,
said 8-10 membered heteroaryl being optionally substituted with one to three substituents each independently selected from the group consisting of:
(a) halo,
(b) oxo,
(c) OH,
(d) CN,
(e) $NO_2$,
(f) $C_{1-6}$ alkyl optionally substituted with one hydroxy or one $C_{1-6}$ alkoxy,
(g) $C_{1-6}$ alkoxy,
(h) $C_{1-6}$ haloalkyl,
(i) $C(O)R^a$,
(j) $COOR^a$,
(k) $NR^aR^b$,
(l) $NHC(O)R^a$, and
(m) $C(O)NR^aR^b$;
$R^3$ is H and $R^4$ is phenyl optionally substituted with one to three substituents each independently selected from the group consisting of: halo, OH, CN, $NO_2$, $C_{1-6}$ alkyl, $C_{1-6}$ alkoxy, $C_{1-6}$ haloalkyl, $C(O)R^a$, $COOR^a$, $NR^aR^b$, $NHC(O)R^a$, and $C(O)NR^aR^b$;
or
$R^3$ and $R^4$ together with the atoms to which they are attached form optionally substituted indan-1-one, said indan-1-one is attached to the piperidine ring of formula (I) through spiro carbon 4 and is optionally substituted with one to three substituents each independently selected from the group consisting of: halo and $C_{1-6}$ alkoxy;
$R^a$ is H or $C_{1-6}$ alkyl;
$R^b$ is H or $C_{1-6}$ alkyl; and
n is 1 or 2.

As used herein, the term "alkyl" refers to a fully saturated branched or unbranched hydrocarbon moiety having up to 6 carbon atoms. Unless otherwise provided, alkyl refers to hydrocarbon moieties having 1 to 6 carbon atoms. Alkyl groups may be optionally substituted with one or more substituents as defined. Representative examples of alkyl include, but are not limited to, methyl, ethyl, n-propyl, iso-propyl, n-butyl, sec-butyl, iso-butyl, tert-butyl, n-pentyl, iso-pentyl, neopentyl, and n-hexyl.

As used herein, the term "alkoxy" refers to an alkyl moiety attached through a oxygen bridge (i.e. a —O—$C_{1-6}$ alkyl wherein alkyl is defined herein). Typically, alkoxy groups have 1 to 6 carbon atoms. Representative examples of alkoxy include, but are not limited to, methoxy, ethoxy, propoxy, 2-propoxy, butoxy, tert-butoxy, pentyloxy, hexyloxy.

As used herein, the term "cycloalkyl" refers to a 4 to 7 membered monocyclic saturated hydrocarbon ring system. Cycloalkyl groups may be optionally substituted with one or more substituents as defined herein. Cycloalkyl includes cyclobutyl, cyclopentyl, cyclohexyl, and cycloheptyl.

As used herein, the term "cycloalkenyl" refers to a 5 to 7 membered monocyclic unsaturated, but not aromatic, hydrocarbon ring system. Cycloalkenyl groups may be optionally substituted with one or more substituents as defined here. Cycloalkenyl includes cyclopentenyl, cyclohexenyl, and cycloheptenyl.

As used herein, the term "halo" refers to fluorine, bromine, chlorine or iodine, in particular fluorine or chlorine. Halogen-substituted groups and moieties, such as alkyl substituted by halogen (haloalkyl) can be mono-, poly- or per-halogenated.

As used herein, the term "haloalkyl" refers to an alkyl as defined herein, which is substituted by one or more halo groups as defined herein. The haloalkyl can be monohaloalkyl, dihaloalkyl or polyhaloalkyl including perhaloalkyl. A monohaloalkyl can have one iodo, bromo, chloro or fluoro within the alkyl group. Dihaloalkyl and polyhaloalkyl groups can have two or more of the same halo atoms or a combination of different halo groups within the alkyl. Typically the polyhaloalkyl contains up to 12, or 10, or 8, or 6, or 4, or 3, or 2 halo groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhalo-alkyl refers to an alkyl having all hydrogen atoms replaced with halo atoms.

As used herein, the term "heteroatoms" refers to nitrogen (N), oxygen (O) or sulfur (S) atoms, in particular nitrogen or oxygen.

As used herein, the term "heteroaryl" refers to a 5 or 6 membered monocyclic aromatic ring system, having 1 to 4 heteroatoms unless specified otherwise. Typical 5 or 6 membered heteroaryl groups include 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, furazanyl, thiadiazolyl, tetrazolyl, 2-, 3-, or 4-pyridyl, 3- or 4-pyridazinyl, 3-, 4-, or 5-pyrazinyl, 2-pyrazinyl, and 2-, 4-, or 5-pyrimidinyl.

Heteroaryl also refers to an 8 to 10 membered bicyclic aromatic ring system having 1 to 4 heteroaroms unless otherwise specified. Heteroaryl also refers to an 8 to 10 membered ring system in which a heteroaromatic ring is fused to one phenyl, cycloalkyl, cycloalkenyl, or heterocyclyl ring, where the radical or point of attachment is on the heteroaromatic ring. Nonlimiting examples include 1-, 2-, 3-, 5-, 6-, 7-, or 8-indolizinyl, 1-, 3-, 4-, 5-, 6-, or 7-isoindolyl, 2-, 3-, 4-, 5-, 6-, or 7-indolyl, 2-, 3-, 4-, 5-, 6-, or 7-indazolyl, 2-, 4-, 5-, 6-, 7-, or 8-purinyl, 1-, 2-, 3-, 4-, 6-, 7-, 8-, or 9-quinolizinyl, 2-, 3-, 4-, 5-, 6-, 7-, or 8-quinoliyl, 1-, 3-, 4-, 5-, 6-, 7-, or 8-isoquinoliyl, 1-, 4-, 5-, 6-, 7-, or 8-phthalazinyl, 2-, 3-, 4-, 5-, or 6-naphthyridinyl, 2-, 3-, 5-, 6-, 7-, or 8-quinazolinyl, 3-, 4-, 5-, 6-, 7-, or 8-cinnolinyl, 2-, 4-, 6-, or 7-pteridinyl, 1-, 2-, 3-, 4-, 5-, 6-, 7-, or 8-4aH carbazolyl, 1-, 2-, 3-, 4-, 5-, 6-, 7-, or 8-carbzaolyl, 1-, 3-, 4-, 5-, 6-, 7-, 8-, or 9-carbolinyl, 1-, 2-, 3-, 4-, 6-, 7-, 8-, 9-, or 10-phenanthridinyl, 1-, 2-, 3-, 4-, 5-, 6-, 7-, 8-, or 9-acridinyl, 1-, 2-, 4-, 5-, 6-, 7-, 8-, or 9-perimidinyl, 2-, 3-, 4-, 5-, 6-, 8-, 9-, or 10-phenathrolinyl, 1-, 2-, 3-, 4-, 6-, 7-, 8-, or 9-phenazinyl, 1-, 2-, 3-, 4-, 6-, 7-, 8-, 9-, or 10-phenothiazinyl, 1-, 2-, 3-, 4-, 6-, 7-, 8-, 9-, or 10-phenoxazinyl, 2-, 3-, 4-, 5-, 6-, or 1-, 3-, 4-, 5-, 6-, 7-, 8-, 9-, or 10-benzisoqinolinyl, 2-, 3-, 4-, or thieno[2,3-b]furanyl, 2-, 3-, 5-, 6-, 7-, 8-, 9-, 10-, or 11-7H-pyrazino[2,3-c]carbazolyl, 2-, 3-, 5-, 6-, or 7-2H-furo[3,2-b]-pyranyl, 2-, 3-, 4-, 5-, 7-, or 8-5H-pyrido[2,3-d]-o-oxazinyl, 1-, 3-, or 5-1H-pyrazolo[4,3-d]-oxazolyl, 2-, 4-, or 54H-imidazo[4,5-d]thiazolyl, 3-, 5-, or 8-pyrazino[2,3-d]pyridazinyl, 2-, 3-, 5-, or 6-imidazo[2,1-b]thiazolyl, 1-, 3-, 6-, 7-, 8-, or 9-furo[3,4-c]cinnolinyl, 1-, 2-, 3-, 4-, 5-, 6-, 8-, 9-, 10, or 11-4H-pyrido[2,3-c]carbazolyl, 2-, 3-, 6-, or 7-imidazo[1,2-b][1,2,4]triazinyl, 7-benzo[b]thienyl, 2-, 4-, 5-, 6-, or 7-benzoxazolyl, 2-, 4-, 5-, 6-, or 7-benzimidazolyl, 2-, 4-, 4-, 5-, 6-, or 7-benzothiazolyl, 1-, 2-, 4-, 5-, 6-, 7-, 8-, or 9-benzoxapinyl, 2-, 4-, 5-, 6-, 7-, or 8-benzoxazinyl, 1-, 2-, 3-, 5-, 6-, 7-, 8-, 9-, 10-, or 11-1H-pyrrolo[1,2-b][2]benzazapinyl. Typical fused heteroaryl groups include, but are not limited to 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, 2-, 4-, 5-, 6-, or 7-benzothiazolyl, cyclohepta[d]imidazolyl, 7,8-dihydro-5H-pyrano[4,3-d]pyrimidinyl, 1H-pyrazolo[3,4-d]pyrimidinyl, thieno[3,2-d]pyrimidinyl, 6,7-dihydro-5H-cyclopentapyrimidinyl, 5,6-dihydro-thiazolo[2,3-c][1,2,4]triazolyl, [1,2,4]triazolo[4,3-a]pyridinyl, 7,8-dihydro-5H-pyrano[3,4-d]pyridazinyl, and isoxazolo[5,4-b]pyridinyl.

Heteroaryl groups containing more than one heteroatom may contain different heteroatoms unless specified otherwise. Heteroaryl groups may be optionally substituted with one or more substituents as defined herein.

As used herein the term "heterocyclyl" refers to a 4 to 7 membered monocyclic saturated or unsaturated ring containing from 1 to 4 heteroatoms. Heterocyclyl rings are not aromatic. Heterocyclyl containing more than one heteroatom may contain different heteroatoms. Heterocyclyl groups may be optionally substituted with one or more substituents as defined herein. Examples of heterocyclyl include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, and the like.

When any group or moiety, such as alkyl, heteroaryl, or phenyl, is defined herein as being "optionally substituted with one, one or two, or one to three substituents each independently selected from the group consisting of" it is understood that the group or moiety is unsubstituted or substituted with one, one or two, or one to three substituents, wherein each substituent is independently selected from the recited group of substituents.

The skilled artisan will appreciate that salts, including pharmaceutically acceptable salts, of the compounds according to formula (I) may be prepared. These salts may be prepared in situ during the final isolation and purification of the compound, or by separately reacting the purified compound in its free acid or free base form with a suitable base or acid, respectively.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Solvates, including pharmaceutically acceptable solvates, of the compounds of formula (I) may also be prepared. "Solvate" refers to a complex of variable stoichiometry formed by a solute and solvent. Such solvents for the purpose of the invention may not interfere with the biological activity of the solute. Examples of suitable solvents include, but are not limited to, water, MeOH, EtOH, and AcOH. Solvates wherein water is the solvent molecule are typically referred to as hydrates. Hydrates include compositions containing stoichiometric amounts of water, as well as compositions containing variable amounts of water.

As used herein, the term "pharmaceutically acceptable" means a compound which is suitable for pharmaceutical use. Salts and solvates (e.g. hydrates and hydrates of salts) of compounds of the invention which are suitable for use in medicine are those where in the counterion or associated solvent is pharmaceutically acceptable. However, salts and solvates having non-pharmaceutically acceptable counterions or associated solvents are within the scope of the present invention, for example, for use as intermediates in the preparation of other compounds of the invention and their pharmaceutically acceptable salts and solvates.

The compounds of formula (I), including salts and solvates thereof, may exist in crystalline forms, non-crystalline forms, or mixtures thereof. The compound or salt or solvate thereof may also exhibit polymorphism, i.e. the capacity of occurring in different crystalline forms. These different crystalline forms are typically known as "polymorphs". Polymorphs have the same chemical composition but differ in packing, geometrical arrangement, and other descriptive properties of crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, all of which may be used for identification. One of ordinary skill in the art will appreciate that different polymorphs may be produced, for example, by changing or adjusting the conditions used in crystallizing/recrystallizing a compound of formula (I).

The invention also includes various isomers of the compounds of formula (I). "Isomer" refers to compounds that have the same composition and molecular weight but differ in physical and/or chemical properties. The structural difference may be in constitution (geometric isomers) or in the ability to rotate the plane of polarized light (stereosiomers). With regard to stereoisomers, the compounds of formula (I) may have one or more asymmetric carbon atom and may occur as racemates, racemic mixtures and as individual enantiomers or diastereomers. All such isomeric forms are included within the present invention, including mixtures thereof. If the compound contains a double bond, the substituent may be in the E or Z configuration. If the compound contains a disubstituted cycloalkyl, the cycloalkyl substituent may have a cis- or trans-configuration. All tautomeric forms are also intended to be included.

Any asymmetric atom (e.g., carbon or the like) of a compound of formula (I) can be present in racemic or enantiomerically enriched, for example the (R)-, (S)- or (R,S)-configuration. In certain embodiments, each asymmetric atom has at least 50 enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of formula (I) can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

The invention includes unlabeled forms as well as isotopically labeled forms of compounds of formula (I). Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$, $^{31}F$, $^{32}P$, $^{35}S$, $^{36}Cl$, $^{125}I$ respectively. The invention includes various isotopically labeled compounds as defined herein, for example those into which radioactive isotopes, such as $^3H$ and $^{14}C$, or those into which non-radioactive isotopes, such as $^2H$ and $^{13}C$ are present. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Furthermore, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Representative Embodiments

Various embodiments of the invention are described herein. It will be recognized that features specified in each embodiment may be combined with other specified features to provide for further embodiments.

One embodiment of the present invention is a compound according to formula (II):

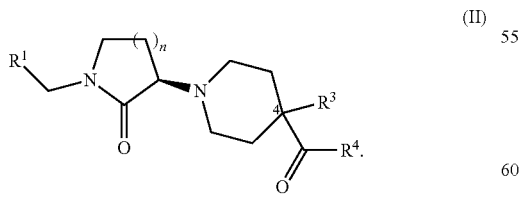

(II)

In another embodiment of the present invention $R^3$ is H and $R^4$ is optionally substituted phenyl. Suitably $R^4$ is phenyl substituted by one or two substituents each independently selected from the group consisting of halo, $C_{1-6}$ alkyl, and $C_{1-6}$ alkoxy. More suitably $R^4$ is phenyl optionally substituted by one or two substituents each independently selected from the group consisting of fluoro, chloro, methyl, and methoxy. In particular $R^4$ is 4-methoxyphenyl, 4-chlorophenyl, 4-fluorophenyl, or 4-methoxyl-3-methylphenyl.

In another embodiment $R^3$ and $R^4$ together with the atoms to which they are attached form optionally substituted indan-1-one. Suitably the indan-1-one is optionally substituted with one $C_{1-6}$ alkoxy, for example methoxy.

In another embodiment n is 1. In another embodiment n is 2. Suitably n is 1.

In another embodiment $R^1$ is $R^2$. Suitably $R^2$ is optionally substituted phenyl. More suitably $R^2$ is phenyl optionally substituted with one or two substituents each independently selected from the group consisting of: halo, for example chloro, and cyano. In particular $R^2$ is 2-chlorobenzonitrile.

In another embodiment $R^2$ is an optionally substituted 5 or 6 membered heteroaryl. Suitably $R^2$ is an optionally substituted pyrimidinyl or tetrazolyl.

In another embodiment $R^2$ is an optionally substituted 8-10 membered bicyclic heteroaryl.

In another embodiment $R^2$ is

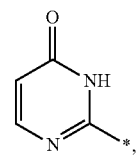

(a)

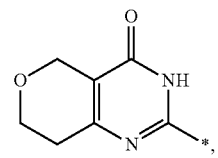

(b)

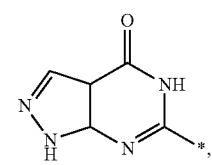

(c)

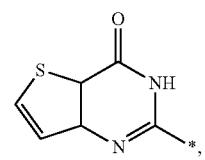

(d)

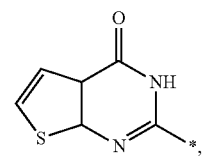

(e)

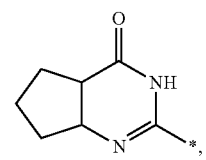

(f)

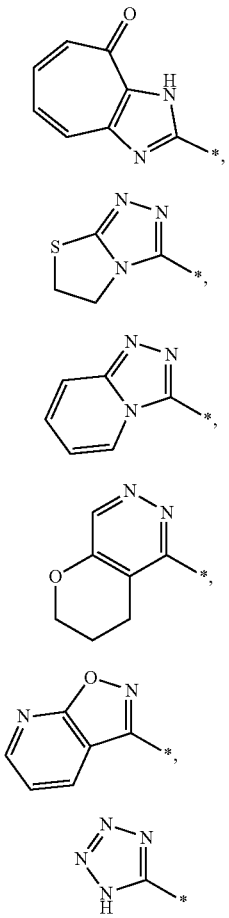

wherein each of (a)-(I) is optionally substituted with one or two substituents each independently selected from the group consisting of halo, OH, CN, $NO_2$, $C_{1-6}$ alkyl, $C_{1-6}$ alkoxy, $C_{1-6}$ haloalkyl, $C(O)R^a$, $COOR^a$, $NR^aR^b$, $NHC(O)R^a$, and $C(O)NR^aR^b$. Suitably $R^2$ is (a)-(I) optionally substituted with one or two substituents each independently selected from the group consisting of halo, CN, and $C_{1-6}$ alkyl. More suitably $R^2$ is (a)-(I) optionally substituted with one or two substituents each independently selected from the group consisting of chloro, bromo, CN, methyl, and ethyl. Suitably $R^2$ is optionally substituted (b), (g), or (h). More suitably $R^2$ is (b), (g), or (h).

Specific compounds of the present invention include:
2-Chloro-6-{3-[4-(4-methoxy-benzoyl)-piperidin-1-yl]-2-oxo-pyrrolidin-1-ylmethyl}-benzonitrile;
2-{3-[4-(4-Methoxy-benzoyl)-piperidin-1-yl]-2-oxo-pyrrolidin-1-ylmethyl}-3,5,7,8-tetrahydro-pyrano[4,3-d]pyrimidin-4-one;
2-{(S)-3-[4-(4-Methoxy-benzoyl)-piperidin-1-yl]-2-oxo-pyrrolidin-1-ylmethyl}-3,5,7,8-tetrahydro-pyrano[4,3-d]pyrimidin-4-one;
2-{(R)-3-[4-(4-Methoxy-benzoyl)-piperidin-1-yl]-2-oxo-pyrrolidin-1-ylmethyl}-3,5,7,8-tetrahydro-pyrano[4,3-d]pyrimidin-4-one;
2-Chloro-5-((3-(4-(4-methoxybenzoyl)piperidin-1-yl)-2-oxopyrrolidin-1-yl)methyl)benzonitrile;
6-{3-[4-(4-Methoxy-benzoyl)-piperidin-1-yl]-2-oxo-pyrrolidin-1-ylmethyl}-1-methyl-1,3a,5,7a-tetrahydro-pyrazolo[3,4-d]pyrimidin-4-one;
2-{3-[4-(4-Methoxy-benzoyl)-piperidin-1-yl]-2-oxo-pyrrolidin-1-ylmethyl}-4a,7a-dihydro-3H-thieno[3,2-d]pyrimidin-4-one;
2-{3-[4-(4-Methoxy-benzoyl)-piperidin-1-yl]-2-oxo-pyrrolidin-1-ylmethyl}-6-methyl-4a,7a-dihydro-3H-thieno[2,3-d]pyrimidin-4-one;
2-{3-[4-(4-Chloro-benzoyl)-piperidin-1-yl]-2-oxo-pyrrolidin-1-ylmethyl}-3,5,7,8-tetrahydro-pyrano[4,3-d]pyrimidin-4-one;
2-{3-[4-(4-Fluoro-benzoyl)-piperidin-1-yl]-2-oxo-pyrrolidin-1-ylmethyl}-3,5,7,8-tetrahydro-pyrano[4,3-d]pyrimidin-4-one;
2-{(S)-3-[4-(4-Fluoro-benzoyl)-piperidin-1-yl]-2-oxo-pyrrolidin-1-ylmethyl}-3,5,7,8-tetrahydro-pyrano[4,3-d]pyrimidin-4-one;
2-{(R)-3-[4-(4-Fluoro-benzoyl)-piperidin-1-yl]-2-oxo-pyrrolidin-1-ylmethyl}-3,5,7,8-tetrahydro-pyrano[4,3-d]pyrimidin-4-one;
2-{(S)-3-[4-(4-Methoxy-3-methyl-benzoyl)-piperidin-1-yl]-2-oxo-pyrrolidin-1-ylmethyl}-3,5,7,8-tetrahydro-pyrano[4,3-d]pyrimidin-4-one;
2-{(R)-3-[4-(4-Methoxy-3-methyl-benzoyl)-piperidin-1-yl]-2-oxo-pyrrolidin-1-ylmethyl}-3,5,7,8-tetrahydro-pyrano[4,3-d]pyrimidin-4-one;
2-((3-(5-methoxy-1-oxo-1,3-dihydrospiro[indene-2,4'-piperidine]-1'-yl)-2-oxopyrrolidin-1-yl)methyl)-7,8-dihydro-3H-pyrano[4,3-d]pyrimidin-4(5H)-one;
(S)-2-((3-(5-methoxy-1-oxo-1,3-dihydrospiro[indene-2,4'-piperidine]-1'-yl)-2-oxopyrrolidin-1-yl)methyl)-7,8-dihydro-3H-pyrano[4,3-d]pyrimidin-4(5H)-one;
(R)-2-((3-(5-methoxy-1-oxo-1,3-dihydrospiro[indene-2,4'-piperidine]-1'-yl)-2-oxopyrrolidin-1-yl)methyl)-7,8-dihydro-3H-pyrano[4,3-d]pyrimidin-4(5H)-one;
2-[4-(4-Methoxy-benzoyl)-2'-oxo-[1,3']bipiperidinyl-1'-ylmethyl]-3,5,7,8-tetrahydro-pyrano[4,3-d]pyrimidin-4-one;
2-[(S)-4-(4-Methoxy-benzoyl)-2'-oxo-[1,3']bipiperidinyl-1'-ylmethyl]-3,5,7,8-tetrahydro-pyrano[4,3-d]pyrimidin-4-one;
2-[(R)-4-(4-Methoxy-benzoyl)-2'-oxo-[1,3']bipiperidinyl-1'-ylmethyl]-3,5,7,8-tetrahydro-pyrano[4,3-d]pyrimidin-4-one;
2-((3-(4-(4-methoxybenzoyl)piperidin-1-yl)-2-oxopyrrolidin-1-yl)methyl)-6,7-dihydro-3H-cyclopenta[d]pyrimidin-4(5H)-one;
2-{3-[4-(4-Methoxy-benzoyl)-piperidin-1-yl]-2-oxo-pyrrolidin-1-ylmethyl}-3H-pyrimidin-4-one;
2-{3-[4-(4-Methoxy-benzoyl)-piperidin-1-yl]-2-oxo-pyrrolidin-1-ylmethyl}-6-methyl-3H-pyrimidin-4-one;
6-Ethyl-2-{3-[4-(4-methoxy-benzoyl)-piperidin-1-yl]-2-oxo-pyrrolidin-1-ylmethyl}-3H-pyrimidin-4-one;
2-{3-[4-(4-Methoxy-benzoyl)-piperidin-1-yl]-2-oxo-pyrrolidin-1-ylmethyl}-5-methyl-3H-pyrimidin-4-one;
2-{3-[4-(4-Methoxy-benzoyl)-piperidin-1-yl]-2-oxo-pyrrolidin-1-ylmethyl}-5,6-dimethyl-3H-pyrimidin-4-one;
2-((3-(4-(4-methoxybenzoyl)piperidin-1-yl)-2-oxopyrrolidin-1-yl)methyl)cyclohepta[d]imidazol-4(3H)-one;
2-{(S)-3-[4-(4-Methoxy-3-methyl-benzoyl)-piperidin-1-yl]-2-oxo-pyrrolidin-1-ylmethyl}-3H-cycloheptaimidazol-4-one;
2-{(R)-3-[4-(4-Methoxy-3-methyl-benzoyl)-piperidin-1-yl]-2-oxo-pyrrolidin-1-ylmethyl}-3H-cycloheptaimidazol-4-one;
2-{(S)-3-[4-(4-Methoxy-benzoyl)-piperidin-1-yl]-2-oxo-pyrrolidin-1-ylmethyl}-3H-cycloheptaimidazol-4-one;
2-{(R)-3-[4-(4-Methoxy-benzoyl)-piperidin-1-yl]-2-oxo-pyrrolidin-1-ylmethyl}-3H-cycloheptaimidazol-4-one;

N-(5,6-dihydrothiazolo[2,3-c][1,2,4]triazol-3-yl)-2-(3-(4-(4-methoxybenzoyl)piperidin-1-yl)-2-oxopyrrolidin-1-yl)acetamide;

N-(5,6-Dihydro-thiazolo[2,3-c][1,2,4]triazol-3-yl)-2-{(S)-3-[4-(4-methoxy-benzoyl)-piperidin-1-yl]-2-oxo-pyrrolidin-1-yl}-acetamide;

N-(5,6-Dihydro-thiazolo[2,3-c][1,2,4]triazol-3-yl)-2-{(R)-3-[4-(4-methoxy-benzoyl)-piperidin-1-yl]-2-oxo-pyrrolidin-1-yl}-acetamide;

N-([1,2,4]triazolo[4,3-a]pyridin-3-yl)-2-(3-(4-(4-methoxybenzoyl)piperidin-1-yl)-2-oxopyrrolidin-1-yl)acetamide;

2-(3-(4-(4-methoxybenzoyl)piperidin-1-yl)-2-oxopyrrolidin-1-yl)-N-(1-methyl-1H-tetrazol-5-yl)acetamide;

N-(3,4-dihydro-2H-pyrano[2,3-d]pyridazin-5-yl)-2-(3-(4-(4-methoxybenzoyl)piperidin-1-yl)-2-oxopyrrolidin-1-yl)acetamide; and N-Isoxazolo[5,4-b]pyridin-3-yl-2-{3-[4-(4-methoxy-benzoyl)-piperidin-1-yl]-2-oxo-pyrrolidin-1-yl}-acetamide.

ENUMERATED EMBODIMENTS

Embodiment 1

A compound according to formula (I)

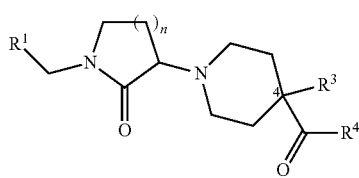

(I)

wherein:

$R^1$ is $R^2$ or $R^2$—NHC(O)—;

$R^2$ is phenyl optionally substituted with one or two substituents each independently selected from the group consisting of: halo, OH, CN, $NO_2$, $C_{1-6}$ alkyl, $C_{1-6}$ alkoxy, $C_{1-6}$ haloalkyl, $C(O)R^a$, $COOR^a$, $NR^aR^b$, $NHC(O)R^a$, and $C(O)NR^aR^b$;

or $R^2$ is a 5 membered heteroaryl having one to four heteroatoms selected from the group consisting of N, O, and S, or $R^2$ is a 6 membered heteraryl having one or two N, said 5 and 6 membered heteroaryl rings being optionally substituted with one to three substituents each independently selected from the group consisting of: halo, oxo, OH, CN, $NO_2$, $C_{1-6}$ alkyl, $C_{1-6}$ alkoxy, $C_{1-6}$ haloalkyl, $C(O)R^a$, $COOR^a$, $NR^aR^b$, $NHC(O)R^a$, and $C(O)NR^aR^b$;

or $R^2$ is an 8-10 membered bicyclic heteroaryl having 3 or 4 heteroatoms selected from the group consisting of N, O, and S, said 8-10 membered heteroaryl being optionally substituted with one to three substituents each independently selected from the group consisting of:

(a) halo,
(b) oxo,
(c) OH,
(d) CN,
(e) $NO_2$,
(f) $C_{1-6}$alkyl optionally substituted with one hydroxy or one $C_{1-6}$ alkoxy,
(g) $C_{1-6}$ alkoxy,
(h) $C_{1-6}$ haloalkyl,
(i) $C(O)R^a$,
(j) $COOR^a$,
(k) $NR^aR^b$,
(l) $NHC(O)R^a$, and
(m) $C(O)NR^aR^b$;

$R^3$ is H and $R^4$ is phenyl optionally substituted with one to three substituents each independently selected from the group consisting of: halo, OH, CN, $NO_2$, $C_{1-6}$alkyl, $C_{1-6}$ alkoxy, $C_{1-6}$ haloalkyl, $C(O)R^a$, $COOR^a$, $NR^aR^b$, $NHC(O)R^a$, and $C(O)NR^aR^b$;

or $R^3$ and $R^4$ together with the atoms to which they are attached form optionally substituted indan-1-one, said indan-1-one is attached to the piperidine ring of formula (I) through spiro carbon 4 and is optionally substituted with one to three substituents each independently selected from the group consisting of: halo and $C_{1-6}$ alkoxy;

$R^a$ is H or $C_{1-6}$ alkyl;

$R^b$ is H or $C_{1-6}$ alkyl; and n is 1 or 2; or a pharmaceutically acceptable salt thereof.

Embodiment 2

The compound according to embodiment 1 having the following formula

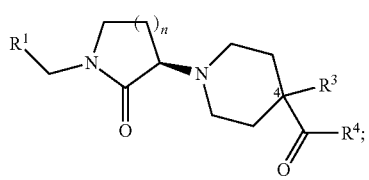

(II)

or a pharmaceutically acceptable salt thereof.

Embodiment 3

The compound according to embodiment 1 or 2 wherein $R^3$ is H; or a pharmaceutically acceptable salt thereof.

Embodiment 4

The compound according to any one of embodiments 1-3 wherein $R^4$ is optionally substituted phenyl; or a pharmaceutically acceptable salt thereof.

Embodiment 5

The compound according to embodiment 4 wherein $R^4$ is substituted phenyl; or a pharmaceutically acceptable salt thereof.

Embodiment 6

The compound according to embodiment 5 wherein $R^4$ is phenyl substituted by one or two substituents each independently selected from the group consisting of halo, $C_{1-6}$ alkyl, and $C_{1-6}$ alkoxy; or a pharmaceutically acceptable salt thereof.

Embodiment 7

The compound according to embodiment 1 or 2 wherein $R^3$ and $R^4$ together with the atoms to which they are attached form optionally substituted indan-1-one; or a pharmaceutically acceptable salt thereof.

Embodiment 8

The compound according to any one of embodiments 1-7 wherein n is 1; or a pharmaceutically acceptable salt thereof.

Embodiment 9

The compound according to any one of embodiments 1-7 wherein n is 2; or a pharmaceutically acceptable salt thereof.

Embodiment 10

The compound according to any one of embodiments 1-9 wherein $R^1$ is $R^2$; or a pharmaceutically acceptable salt thereof.

Embodiment 11

The compound according to any one of embodiments 1-10 wherein $R^2$ is optionally substituted phenyl; or a pharmaceutically acceptable salt thereof.

Embodiment 12

The compound according to any one of embodiments 1-10 wherein $R^2$ is an optionally substituted 5 or 6 membered heteroaryl; or a pharmaceutically acceptable salt thereof.

Embodiment 13

The compound according to any one of embodiments 1-10 wherein $R^2$ is an optionally substituted 8-10 membered bicyclic heteroaryl; or a pharmaceutically acceptable salt thereof.

Embodiment 14

The compound according to any one of embodiments 1-10 wherein $R^2$ is

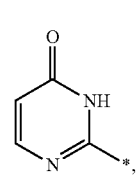
(a)

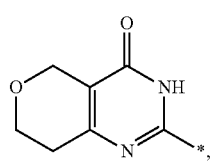
(b)

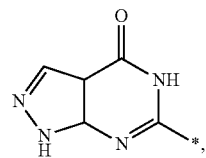
(c)

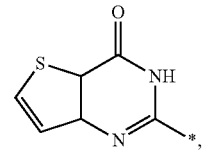
(d)

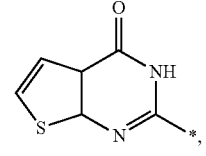
(e)

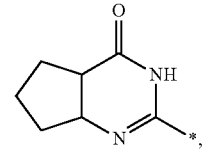
(f)

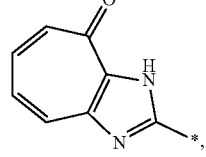
(g)

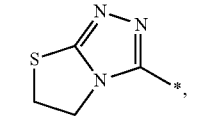
(h)

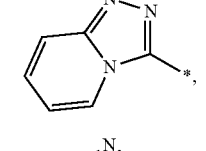
(i)

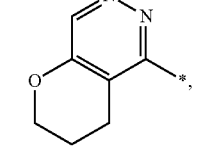
(j)

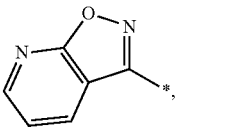
(k) or

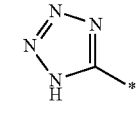
(l)

wherein each of (a)-(l) is optionally substituted with one or two substituents each independently selected from the group consisting of halo, OH, CN, $NO_2$, $C_{1-6}$ alkyl, $C_{1-6}$ alkoxy, $C_{1-6}$ haloalkyl, C(O)R$^a$, COOR$^a$, NR$^a$R$^b$, NHC(O)R$^a$, and C(O)NR$^a$R$^b$; or a pharmaceutically acceptable salt thereof.

General Synthetic Procedures

The compounds of the present invention may be made by a variety of methods, including standard chemistry. Illustrative general synthetic methods are set out below and specific compounds of the invention as prepared are given in the Examples.

The compounds of formula (I) may be prepared by methods known in the art of organic synthesis as set forth in part by the following synthetic schemes. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of formula (I).

Those skilled in the art will recognize if a stereocenter exists in the compounds of formula (I). Accordingly, the present invention includes both possible stereoisomers and includes not only racemic compounds but the individual enantiomers as well. When a compound is desired as a single enantiomer, it may be obtained by stereospecific synthesis or by resolution of the final product or any convenient intermediate. Resolution of the final product, an intermediate, or a starting material may be effected by any suitable method known in the art. See, for example, "Stereochemistry of Organic Compounds" by E. L. Eliel, S. H. Wilen, and L. N. Mander (Wiley-interscience, 1994).

The compounds described herein may be made from commercially available starting materials or synthesized using known organic, inorganic, and/or enzymatic processes.

methods, including the treatment of the lactam with an alkylating agent, such as an alkyl halide 2 or alkyl sulfonic ester in the presence of a suitable base, such as sodium hydride or KHMDS, in a suitable solvent, such as acetonitrile, THF or DMF over a range of suitable temperatures.

Scheme 2

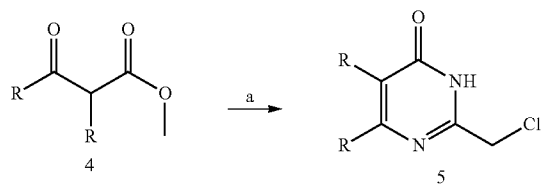

a) TEA, 2-chloroacetamidine, MeOH

Alkyl halides 2 are commercially available or can be made a shown in Scheme 2. There are several methods for making chloromethyl pyrimidinones 5 including the treatment of β-keto esters 4 with 2-chloromethyl acetamide in the presence of a suitable base, such as triethylamine, in a suitable solvent, such as methanol.

Scheme 3

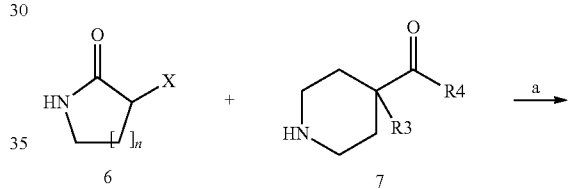

Scheme 1

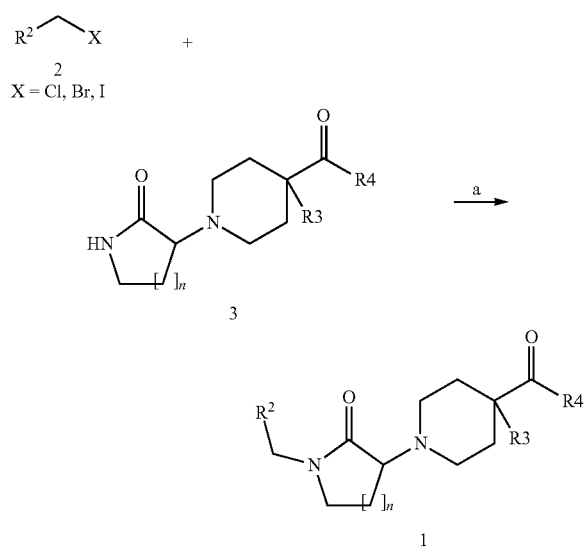

a) NaH or KHMDS, MeCN, THF or DMF, -30 to 70° C.

As shown in Scheme 1, 1 can be prepared by alkylation of the lactam moiety of 3 can be accomplished by a variety of X = Cl, Br, OMs, OTs
n = 1, 2 or 3
a) DIEA, MeCN or DMF or PhMe:MeCn (1:1), 15-85C The synthesis of 3 can be accomplished by a variety of methods, including the elaboration of appropriately substituted 5 and 6 member lactams 6 as shown in Scheme 3. The substitution of a leaving group at the 3-position, such as a chloro, bromo, or mesylate, by an appropriate nucleophile, such as a substituted piperidine 7 in a suitable solvent, such as acetonitrile or DMF or a solvent mixture such as acetonitrile and toluene, can be accomplished over a range of temperatures and reaction durations.

Scheme 4

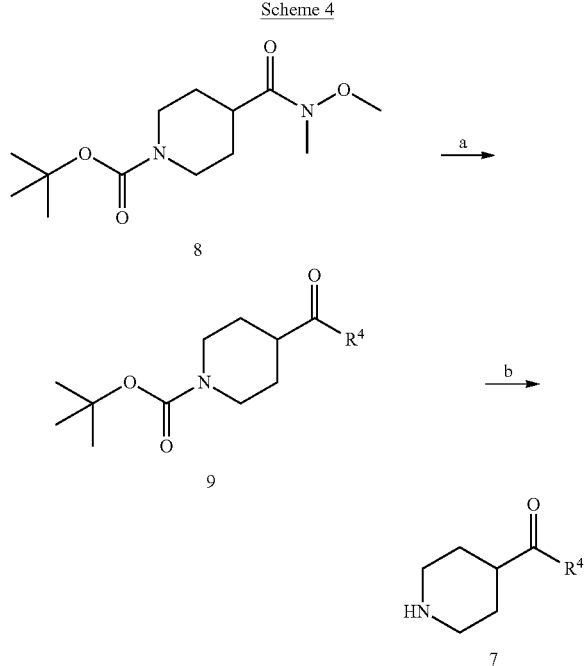

a) R⁴-Br, n-BuLi, THF, -78° C. or Ar-MgBr, THF, 0° C.; b) TFA, DCM

The synthesis of 7 can be achieved by way of the Weinreb ketone synthesis as shown in Scheme 4. In this scheme, Weinreb amide 8 is treated with a Grignard reagent or an organometallic reagent such as n-butyllithium in the presence of R⁴—Br to form ketone 9. The tert-butyl protecting group of 9 is removed through the addition of trifluoroacetic acid in dichloromethane to yield the secondary amine 7.

Scheme 5

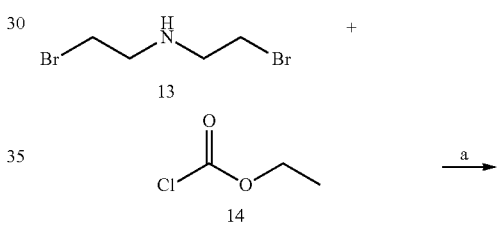

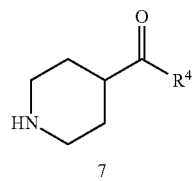

a) Ar-Sh (Ar = Ph or 4-MePh), HATU, DIEA, DMF;
b) R-B(OH)₂), Pd₂(dba)₃, ligand TFP, copper
l) thiophene-2-carboxylate, DME, 50° C.;
c) TFA, DCM or 4 N HCl, dioxane The synthesis of 7 can also be achieved through a thioester boronic acid cross coupling reaction as shown in Scheme 5. Thioester 11 is achieved through the treatment of 10 with the appropriate aryl thiol in the presence of HATU, DIEA and DMF. 11 is converted into ketone 12 through the addition of the appropriate boronic acid in the presence of a palladium metal catalyst such as Pd₂(dba)₃ in the presence of tris(2-furyl)phosphine and copper (I) thiophene-2-carboxylate in dimethoxyethane (DME). The tert-butyl protecting group of 9 is removed through the addition of trifluoroacetic acid in dichloromethane to yield the secondary amine 7.

Scheme 6

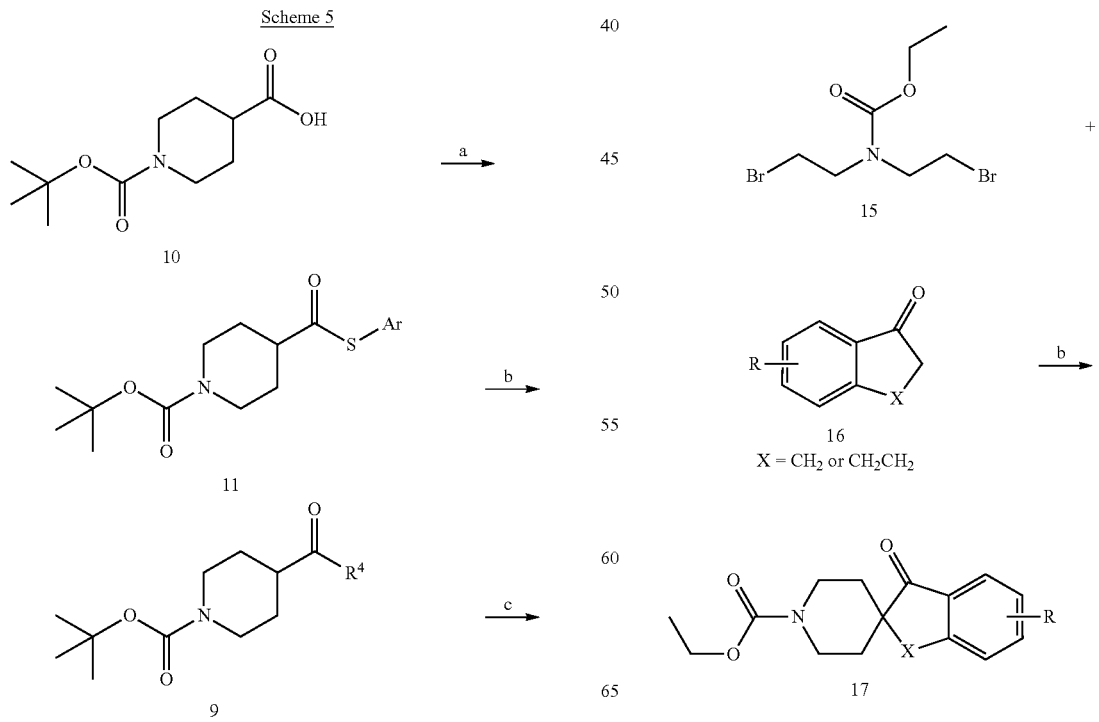

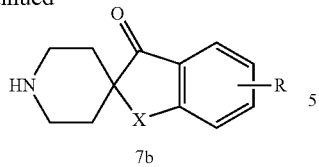

7b a) NaOH, H$_2$O;
b) NaH, DMF, 50° C.;
c) 6 N HCl, reflux

The formation of substituted spiro[indene-2,4'-piperidin]-1(3H)-ones can be accomplished by a variety of methods, including those described below. A suitable bis-(2-bromo-ethyl)-carbamic acid alkyl ester, such as bis-(2-bromo-ethyl)-carbamic acid ethyl ester can by synthesized by protection of bis-(2-bromo-ethyl)-amine with a suitable protecting group, such as a carbamate, such as ethyl carbamate, via reaction with carbamoylating agents, such as alkyl chloroformates, such as ethyl chloroformate, in a suitable solvent, such as water, in the presence of a base, such as NaOH at temperatures from −40° C. to 40° C. Formation of the protected spiro[indene-2,4'-piperidin]-1(3H)-ones can be accomplished by reacting a suitable ketone, such as a substituted indanone, with a strong base, such as sodium hydride, in a polar solvent, such as Dmolecular formula at temperatures from 0° C. to 100° C. Deprotection of the piperidinyl nitrogen can be accomplished via a variety of methods, such as such as treatment with a strong acid or base, such as 6 N HCl at temperatures between 0° C. and 100° C.

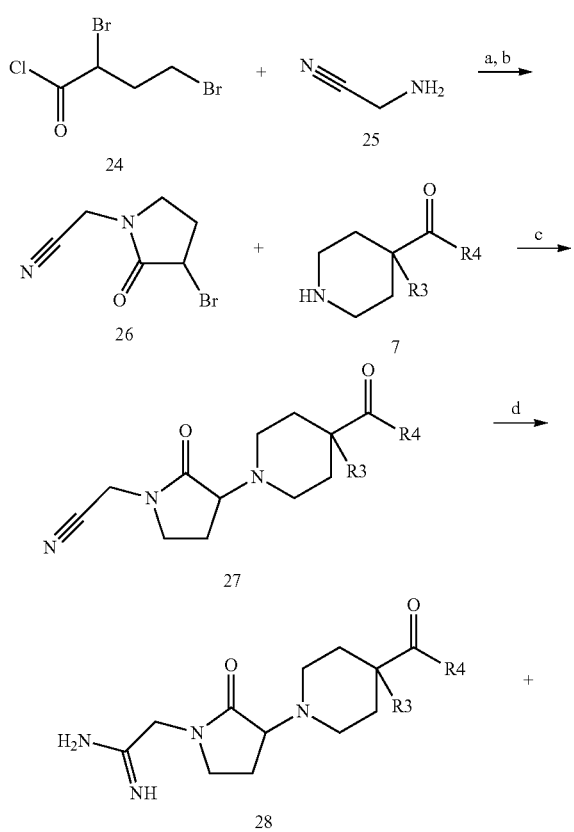

Scheme 7

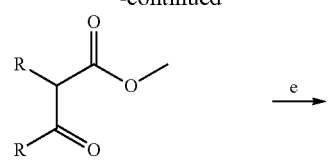

4

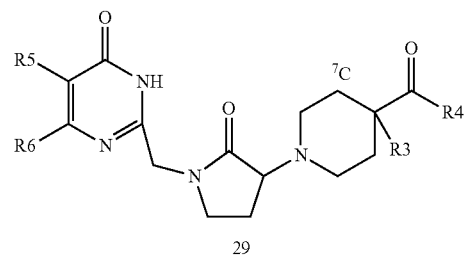

29 a) TEA, DCM;
b) NaH, PhMe;
c) TEA, MeCN;
d) i. NaOMe, MeOH; ii. NH$_4$Cl;
e) NaOEt, EtOH

The synthesis of (2-[3-(4-piperidin-1-yl)-2-oxo-pyrrolidin-1-ylmethyl]-3H-pyrimidin-4-one analogs 29 can be accomplished by a variety of methods, including routes that rely on the use of amidine intermediates to form the pyrimidinone ring. The synthesis of lactam acetonitrile intermediates, such as 2-(3-bromo-2-oxopyrrolidin-1-yl)acetonitrile 26 can be accomplished by a variety of methods, including reacting aminoacetonitrile 25 with a suitable electrophile, such as 2,4-dibromobutanoyl chloride 24, in the presence of a suitable base, such as an amine base, such as triethylamine, in a suitable solvent such as dichloromethane. Installation of the piperidine moiety, such as aryl-piperidin-4-yl-methanone analogs 7, can be accomplished by a variety of methods, such as displacement of a suitable leaving group, such as a bromide, in the presence of a suitable base, such as an amine base, such as triethylamine, in a suitable solvent such as acetonitrile. Conversion of the resulting nitrile 27 to the amidine 28 can be accomplished via a variety of methods, including treatment with an alkoxide base, such as sodium methoxide, and an ammonium source, such as ammonium chloride, in a suitable solvent, such as methanol. Formation of the pyrimidinone moiety 29 can be accomplished by a variety of methods, including reacting the amidine 28 with an appropriately substituted β-ketoester 4, such as methyl 2-oxocyclopentanecarboxylate, in the presence of a suitable base, such as an alkoxide base, such as sodium ethoxide, in a suitable solvent, such as ethanol.

Scheme 8

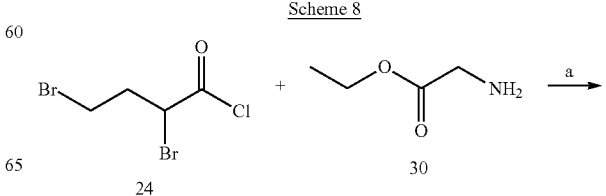

24    30

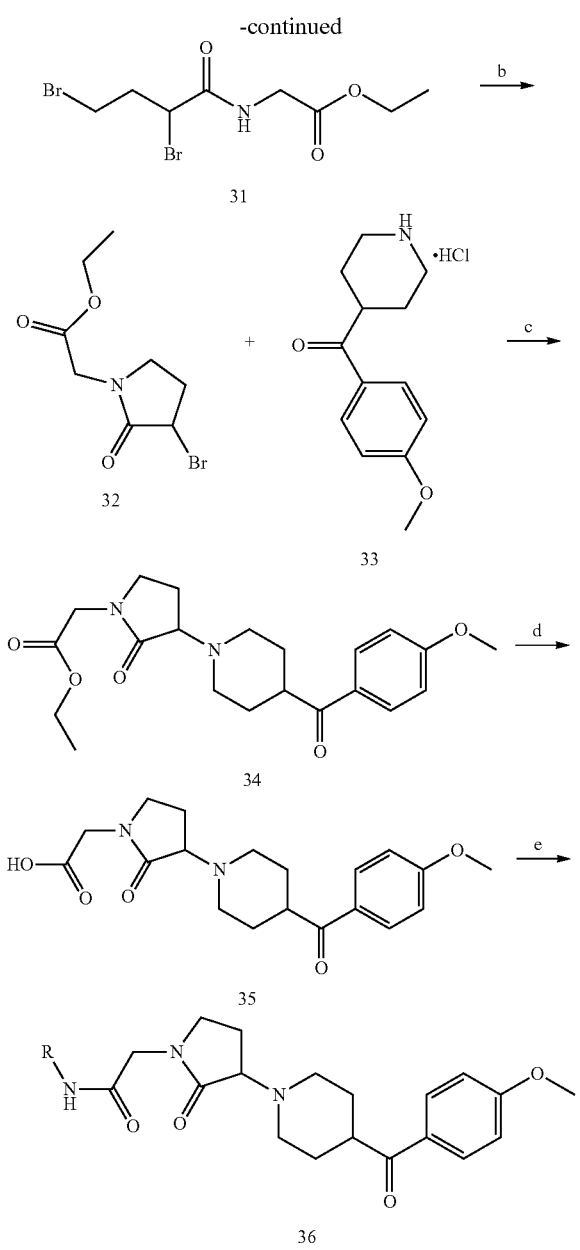

a) DMC, water, 0° C.;
b) NaH, PhH;
c) TEA, MeCN, 70° C.;
d) NaOH, water, EtOH:
e) R-NH₂, HATU, DIEA, DCM The synthesis of N-heterocyclic-2-(3-(4-(4-methoxybenzoyl)piperidin-1-yl)-2-oxopyrrolidin-1-yl)acetamide analogs 36 can be accomplished by a variety of methods, including routes that rely on the use of carboxylic acid intermediates to form the heterocyclic acetamide. The synthesis of ethyl 2-(2,4-dibromobutanamido)acetate intermediate 31 can be accomplished by reacting ethyl 2-aminoacetate hydrochloride 30 with a suitable electrophile, such as 2,4-dibromobutanoyl chloride 24, in a suitable solvent mixture, such as dichloromethane and water. Cyclization to ethyl 2-(3-bromo-2-oxopyrrolidin-1-yl)acetate 32 can be accomplished by reaction with a suitable base, such as sodium hydride, in a suitable solvent, such as benzene. Installation of the piperidine moiety, such as (4-methoxyphenyl)(piperidin-4-yl) methanone, can be accomplished by a variety of methods, such as displacement of a suitable leaving group, such as a bromide, in the presence of a suitable base, such as an amine base, such as triethylamine, in a suitable solvent such as acetonitrile. Conversion of the resulting carboxylic ester 34 to the carboxylic acid 35 can be accomplished via a variety of methods, including treatment with an inorganic base, such as sodium hydroxide, in a suitable solvent combination, such as ethanol and water. Formation of heterocyclic acetamides 36 can be accomplished by a variety of methods, including reacting 2-(3-(4-(4-methoxybenzoyl)piperidin-1-yl)-2-oxopyrrolidin-1-yl)acetic acid 35 with suitable heterocyclic amines in the presence of a suitable coupling reagent, such as HATU, and a suitable amine base, such as diisopropylethylamine, in a suitable solvent, such as dichloromethane.

Compositions

In another aspect, the present invention provides a pharmaceutical composition comprising a compound of formula (I), or a pharmaceutically acceptable salt thereof, and a pharmaceutically acceptable carrier. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers, etc.

Typically, the pharmaceutical compositions are tablets or gelatin capsules comprising the active ingredient together with a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired
d) disintegrants, e.g., starches, agar, alginic acid or its sodium salt, or effervescent mixtures; and/or
e) absorbents, colorants, flavors and sweeteners.

Tablets may be either film coated or enteric coated according to methods known in the art.

Suitable compositions for oral administration include an effective amount of a compound of formula (I), or a pharmaceutically acceptable salt thereof, in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

Methods of Use

The compounds of formula (I) are tankyrase inhibitors and therefore may be useful in the treatment of diseases mediated by tanykyrase, including Wnt signaling related disorders and tankyrase 1 and 2 (TNKS/TNKS2) signaling related disorders.

Wnt signaling related disorders include diseases and conditions associated with aberrant Wnt signaling including but not limited to Wnt signaling-related cancers (e.g., colorectal cancer, malignant medulloblastoma and other primary CNS malignant neuroectodermal tumors, rhabdomyosarcoma, lung cancer, in particular small cell lung cancer, gut-derived tumors, including but not limited to cancer of the esophagus, stomach, pancreas, and biliary duct system, prostate and bladder cancers, and liver cancer); other, non-oncogenic proliferative diseases, such as proliferative skin disorders (e.g., psoriasis, dermatitis); osteoporosis; osteoarthritis; fibrosis; schizophrenia; vascular disease; cardiac disease; neurodegenerative diseases such as Alzheimer's disease; remyelination, including remyelination after brain and/or spinal code injury; and pulmonary fibrosis. Aberrant upregulation of Wnt signaling is associated with cancer, osteoarthritis, and polycystic kidney disease, while aberrant down regulation of Wnt signaling has been linked to osteoporosis, obesity, diabetes, and neuronal degenerative diseases.

Tankyrase signaling related disorders include diseases and conditions associated with aberrant tankyrase 1 and 2 signaling, including but not limited to cancer (e.g., leukemia, lymphoma, melanoma, multiple myeloma, lung, ovarian, and breast cancer) metabolic diseases and viral infection (e.g. Herpes Simplex Virus infection).

The term "a therapeutically effective amount" of a compound of the present invention refers to an amount of a compound of formula (I) that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of a compound of formula (I) when administered to a subject, is effective to (1) at least partially alleviating, inhibiting, preventing and/or ameliorating a condition, or a disorder or a disease (i) mediated by tankyrase, or (ii) associated with tankyrase activity, or (iii) characterized by activity (normal or abnormal) of tankyrase; or (2) reducing or inhibiting the activity of tankyrase or (3) reducing or inhibiting the expression of tankyrase. In another non-limiting embodiment, the term "a therapeutically effective amount" refers to the amount of a compound of formula (I) when administered to a cell, or a tissue, or a non-cellular biological material, or a medium, is effective to at least partially reducing or inhibiting the activity of tankyrase; or at least partially reducing or inhibiting the expression of tankyrase.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

Thus, as a further embodiment, the present invention provides the use of a compound of formula (I) or a pharmaceutically acceptable salt thereof, in therapy. In a further embodiment, the therapy is selected from a disease which may be treated by tankyrase inhibition. In one embodiment the disease is a Wnt signaling related disorder. In another embodiment the disease is a tankyrase signaling related disorder. In another embodiment, the disease is cancer, in particular a cancer selected from the group consisting of leukemia, melanoma, multiple myeloma, lymphoma, lung cancer, esophageal cancer, stomach cancer, pancreas cancer, biliary duct system cancer, ovarian cancer, breast cancer, prostate cancer, bladder cancer, colon cancer and liver cancer. In another embodiment, the disease is cancer, in particular, a cancer selected from the group consisting of leukemia, lung cancer, pancreas cancer, breast cancer and colon cancer. In another embodiment the disease is a cancer selected from the group consisting of colon, pancreas, and breast.

In another embodiment, the invention provides a use of a compound of formula (I), or a pharmaceutically acceptable salt thereof, in that manufacture of a medicament for the treatment of a disease mediated by tankyrase inhibition. In one embodiment the disease is a Wnt signaling related disorder. In another embodiment the disease is a tankyrase signaling related disorder. In another embodiment, the disease is cancer, in particular a cancer selected from the group consisting of leukemia, melanoma, multiple myeloma, lymphoma, lung cancer, esophageal cancer, stomach cancer, pancreas cancer, biliary duct system cancer, ovarian cancer, breast cancer, prostate cancer, bladder cancer, colon cancer and liver cancer. In another embodiment, the disease is cancer, in particular a cancer selected from the group consisting of leukemia, lung cancer, pancreas cancer, breast cancer and colon cancer. In another embodiment the disease is a cancer selected from the group consisting of colon, pancreas, and breast.

In another embodiment, the invention provides a method for the treatment of a disease mediated by tankyrase inhibition comprising administration of a therapeutically effective amount of a compound of formula (I) or a pharmaceutically acceptable salt thereof to a subject in need thereof. In one embodiment the disease is a Wnt signaling related disorder. In another embodiment the disease is a tankyrase signaling related disorder. In a further embodiment, the disease is cancer, in particular a cancer selected from the group consisting of leukemia, melanoma, multiple myeloma, lymphoma, lung cancer, esophageal cancer, stomach cancer, pancreas cancer, biliary duct system cancer, ovarian cancer, breast cancer, prostate cancer, bladder cancer, colon cancer and liver cancer. In another embodiment, the disease is cancer, in particular a cancer selected from the group consisting of leukemia, lung cancer, pancreas cancer, breast cancer and colon cancer. In another embodiment the disease is a cancer selected from the group consisting of colon, pancreas, and breast.

Combinations

The compounds of the present invention may be administered either simultaneously with, or before or after, one or more other therapeutic agent(s). The compounds of the present invention may be administered separately, by the same or different route of administration, or together in the same pharmaceutical composition as the other agents.

In one embodiment, the invention provides a product comprising a compound of formula (I) and at least one other therapeutic agent as a combined preparation for simultaneous, separate or sequential use in therapy. In one embodiment, the therapy is the treatment of a disease or condition mediated by TNKS inhibition. Products provided as a combined preparation include a composition comprising the compound of formula (I) and the other therapeutic agent(s) together in the same pharmaceutical composition, or the compound of formula (I) and the other therapeutic agent(s) in separate form, e.g. in the form of a kit.

In one embodiment, the invention provides a pharmaceutical composition comprising a compound of formula (I) and another therapeutic agent(s). Optionally, the pharmaceutical composition may comprise a pharmaceutically acceptable excipient, as described above.

In one embodiment, the invention provides a kit comprising two or more separate pharmaceutical compositions, at least one of which contains a compound of formula (I). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula (I) for treating a disease or condition mediated by tankyrase inhibition wherein the medicament is prepared for administration with another therapeutic agent. The invention also provides the use of another therapeutic agent for treating a disease or condition mediated by tankyrase inhibition, wherein the medicament is administered with a compound of formula (I).

The invention also provides a compound of formula (I) for use in a method of treating a disease or condition mediated by tankyrase inhibition, wherein the compound of formula (I) is prepared for administration with another therapeutic agent. The invention also provides another therapeutic agent for use in a method of treating a disease or condition mediated by tankyrase inhibition, wherein the other therapeutic agent is prepared for administration with a compound of formula (I). The invention also provides a compound of formula (I) for use in a method of treating a disease or condition mediated by tankyrase inhibition, wherein the compound of formula (I) is administered with another therapeutic agent. The invention also provides another therapeutic agent for use in a method of treating a disease or condition mediated by tankyrase inhibition, wherein the other therapeutic agent is administered with a compound of formula (I).

The invention also provides the use of a compound of formula (I) for treating a disease or condition mediated by tankyrase inhibition, wherein the patient has previously (e.g. within 24 hours) been treated with another therapeutic agent. The invention also provides the use of another therapeutic agent for treating a disease or condition mediated by tankyrase inhibition, wherein the patient has previously (e.g. within 24 hours) been treated with a compound of formula (I).

In one embodiment, the other therapeutic agent is selected from selected from the group of, but not limited to Hedgehog antagonists, PI3K inhibitors, MEK inhibitors, tyrosine kinase inhibitors, alkylating agents, anti-metabolites, microtubule inhibitors, telomerase inhibitors, PARP inhibitors, and RAF inhibitors.

An example of a Hedgehog antagonist is 2-chloro-N-[4-chloro-3-(2-pyridinyl)phenyl]-4-(methylsulfonyl)-benzamide (also known as GDC-0449, and described in PCT Publication No. WO 06/028958).

Some examples of PI3K inhibitors include: 4-[2-(1H-Indazol-4-yl)-6-[[4-(methylsulfonyl)piperazin-1-yl]methyl]thieno[3,2-d]pyrimidin-4-yl]morpholine (also known as GDC 0941 and described in PCT Publication Nos. WO 09/036082 and WO 09/055730) and 2-Methyl-2-[4-[3-methyl-2-oxo-8-(quinolin-3-yl)-2,3-dihydroimidazo[4,5-c]quinolin-1-yl]phenyl]propionitrile (also known as BEZ 235 or NVP-BEZ 235, and described in PCT Publication No. WO 06/122806).

An example of a Mitogen-activated protein kinase kinase (MEK) inhibitor is XL-518 (Cas No. 1029872-29-4, available from ACC Corp.).

Some examples of tyrosine kinase inhibitors include: Erlotinib hydrochloride (sold under the trademark Tarceva® by Genentech/Roche), Linifanib (N-[4-(3-amino-1H-indazol-4-yl)phenyl]-N'-(2-fluoro-5-methylphenyl)urea, also known as ABT 869, available from Genentech), sunitinib malate (sold under the tradename Sutent® by Pfizer), bosutinib (4-[(2,4-dichloro-5-methoxyphenyl)amino]-6-methoxy-7-[3-(4-methylpiperazin-1-yl)propoxy]quinoline-3-carbonitrile, also known as SKI-606, and described in U.S. Pat. No. 6,780,996), dasatinib (sold under the tradename Sprycel® by Bristol-Myers Squibb), pazopanib (also known as Armala™ sold under the tradename Votrient® by GlaxoSmithKline), and imatinib and imatinib mesylate (sold under the tradenames Gilvec® and Gleevec® by Novartis).

Some examples of alkylating agents include: temozolomide (sold under the tradenames Temodar® and Temodal® by Schering-Plough/Merck), dactinomycin (also known as actinomycin-D and sold under the tradename Cosmegen®), melphalan (also known as L-PAM, L-sarcolysin, and phenylalanine mustard, sold under the tradename Alkeran®), altretamine (also known as hexamethylmelamine (HMM), sold under the tradename Hexalen®), carmustine (sold under the tradename BiCNU®), bendamustine (sold under the tradename Treanda®), busulfan (sold under the tradenames Busulfex® and Myleran®), carboplatin (sold under the tradename Paraplatin®), lomustine (also known as CCNU, sold under the tradename CeeNU®), cisplatin (also known as CDDP, sold under the tradenames Platinol® and Platinol®-AQ), chlorambucil (sold under the tradename Leukeran®), cyclophosphamide (sold under the tradenames Cytoxan® and Neosar®), dacarbazine (also known as DTIC, DIC and imidazole carboxamide, sold under the tradename DTIC-Dome®), altretamine (also known as hexamethylmelamine (HMM) sold under the tradename Hexalen®), ifosfamide (sold under the tradename Ifex®), procarbazine (sold under the tradename Matulane®), mechlorethamine (also known as nitrogen mustard, mustine and mechloroethamine hydrochloride, sold under the tradename Mustargen®), streptozocin (sold under the tradename Zanosar®), thiotepa (also known as thiophosphoamide, and TESPA and TSPA, sold under the tradename Thioplex®).

Some examples of Anti-metabolites include: claribine (2-chlorodeoxyadenosine, sold under the tradename Leustatin®), 5-fluorouracil (sold under the tradename Adrucil®), 6-thioguanine (sold under the tradename Purinethol®), pemetrexed (sold under the tradename Alimta®), cytarabine (also known as arabinosylcytosine (Ara-C), sold under the tradename Cytosar-U®), cytarabine liposomal (also known as Liposomal Ara-C, sold under the tradename DepoCyt™), decitabine (sold under the tradename Dacogen®), hydroxyurea (sold under the tradenames Hydrea®, Droxia™ and Mylocel™), fludarabine (sold under the tradename Fludara®), floxuridine (sold under the tradename FUDR®), cladribine (also known as 2-chlorodeoxyadenosine (2-CdA) sold under the tradename Leustatin™), methotrexate (also known as amethopterin, methotrexate sodim (MTX), sold under the tradenames Rheumatrex® and Trexall™), and pentostatin (sold under the tradename Nipent®).

Some examples of microtubule inhibitors are vinorelbine (sold under the trade name Navelbine®), vindesine (sold under the trade name Eldisine®), estramustine (sold under the trade name Emcyt®), vincristine (Oncovin®), triclabendazole (Egaten®), secnidazole, quinfamide, podophyllotoxin, mebendazole, griseofulvin, flubendazole, eribulin, colchicine, ciclobendazole, cabazitaxel, albendazole, and vinorelbine.

An example of a telomerase inhibitor is imetelstat.

Some examples of PARP inhibitors include: olaparib (from Astrazeneca), iniparib (also known as BSI-201), AGO14699 (Pfizer), veliparib (also known as ABT-888 from Enzo), and MK4827 (Merck).

Some examples of RAF inhibitors include: 2-Chloro-5-[2-Phenyl-5-(4-pyridinyl)-1H-imidazol-4-yl]phenol (also known as L-779450), 3-(dimethylamino)-N-[3-[(4-hydroxybenzoyl)amino]-4-methylphenyl]-benzamide (also known as ZM-336372) and sorafenib (marketed as Nexavar® by Bayer).

INTERMEDIATES AND EXAMPLES

The following examples are intended to be illustrative only and not limiting in any way.

Abbreviations used are those conventional in the art or the following:
AcOH acetic acid
BOC tertiary butyl carboxy
C Celsius
d doublet
dd doublet of doublets
DCM dichloromethane
DIEA diethylisopropylamine
DME 1,4-dimethoxyethane
DMF N,N-dimethylformamide
DMSO dimethylsulfoxide
EtOAc ethyl acetate
EtOH ethanol
EDCL 1-ethyl-3-(3'-dimethylaminopropyl)carbodiimide
g gram
h hour(s)
HBTU 1-[bis(dimethylamino)methylene]-1H-benzotriazolium hexafluorophosphate(1-) 3-oxide HOBt 1-hydroxy-7-azabenzotriazole
HPLC high pressure liquid chromatography
IR infrared spectroscopy
kg kilogram
L liter
LCMS liquid chromatography and mass spectrometry
MTBE methyl tert butyl either
MeOH methanol
MS mass spectrometry
MW microwave
m multiplet
min minutes
mL milliliter(s)
µM micromolar
m/z mass to charge ratio
nm nanometer
nM nanomolar
N normal
NMR nuclear magnetic resonance
Pa pascal
Pd/C palladium on carbon
rac racemic
RP-HPLC reverse phase-high pressure liquid chromatography
s singlet
t triplet
TEA triethylamine
TLC thin layer chromatography
TFA trifluoroacetic acid
THF tetrahydrofuran Intermediate 1

4-Oxo-tetrahydro-pyran-3-carboxylic acid methyl ester

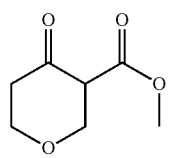

To a solution of tetrahydro-pyran-4-one (1.3 kg, 12.98 mol) and carbonic acid dimethyl ester (11.69 kg, 129.8 mol) was added solid potassium tert-butoxide (1.89 kg, 16.08 mol) in portions at −10° C. over 2 h under nitrogen protection. The suspension was stirred at room temperature 10 h after the addition. LCMS (215 nm) indicated that tetrahydro-pyran-4-one had been completely consumed. The reaction was acidified by HCl (2 N) to pH 6~7 and then the phases were separated. The organic phase was washed with water (3 L×2) and the combined aqueous phases were extracted with MTBE (2.5 L×2). The combined organic phase was concentrated under reduced pressure at 25° C. to remove most of MTBE. The residue was distilled out by oil pump (~200 Pa) at 74° C. to give the title compound as colorless oil (545 g, 26.3%). CHN analysis: calculated (results). C, 53.16 (53.10), H, 6.37 (6.245), N, 0.00 (0.00).

Intermediate 2

2-Chloro-acetamidine

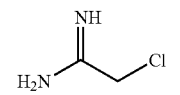

Sodium (18.3 g, 0.795 mol) was completely dissolved in 2 L of MeOH at 25° C. and stirred for 1 hour. To the solution was then added chloro-acetonitrile (600 g, 7.95 mol) dropwise in 1 hour under the protection of $N_2$. After being stirred at about 20° C. for an additional hour, $NH_4Cl$ (514 g, 8.73 mol) was added in portions over 45 minutes (the solution turned to yellow and then red, and then a black liquid was obtained), the reaction mixture was then allowed to stir at 15-20° C. for 16 hours. After filtration, the filtrate was concentrated to give a residue, which was triturated with MTBE (1 L×2) to give the title compound as a black solid (988 g, 96%).

Intermediate 3

2-Chloromethyl-3,5,7,8-tetrahydro-pyrano[4,3-d]pyrimidin-4-one

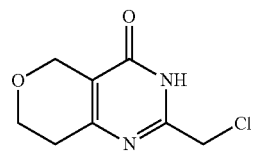 [SMILES: O=c1[nH]c(CCl)nc2c1COCC2]

A mixture of crude 4-oxo-tetrahydro-pyran-3-carboxylic acid methyl ester (1780 g, 11 mol) and triethylamine (830 g, 8.2 mol) in MeOH (3560 mL) was cooled to 0° C. under $N_2$. A solution of 2-chloro-acetamidine (567 g, 4.4 mol) in 890 mL of MeOH was added dropwise over 50 minutes. The reaction mixture was stirred at 0° C. for 30 minutes and then at about 20° C. for 16 hours. LCMS at 215 nm and TLC (DCM:MeOH=10:1) analysis showed that most of 4-oxo-tetrahydro-pyran-3-carboxylic acid methyl ester was consumed. The mixture was then filtered and concentrated to give black oil, which was subsequently purified by flash column chromatography on silica gel and eluted with DCM to give yellow solid/oil mixture, which was further triturated with MTBE (~1200 mL) and $H_2O:CH_3CN:EA=1:1:2$ (~600 mL) to give the title compound as a white solid (318 g). MS m/z 201.2 (M+H). CHN analysis: calculated (results). C, 47.89 (47.95), H, 4.52 (4.401), N, 13.96 (13.76).

Intermediate 4

Bis-(2-bromo-ethyl)-carbamic acid ethyl ester

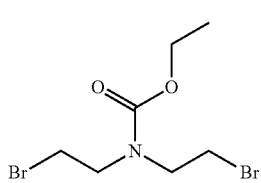

To a stirred solution of bis-(2-bromo-ethyl)-amine (1 g, 3.21 mmol) in water (10 mL) at 0° C. was added ethyl chloroformate (0.293 mL, 3.08 mmol) and then NaOH (4.01 mL, 8.02 mmol), and stirred for 10 min at 0° C. The reaction mixture was acidified by 2 N HCl to pH 5, and extracted three times with 20 mL of ethyl acetate, dried over Na$_2$SO$_4$ and concentrated in vacuo. The crude product was purified by flash chromatography (gradient of 85:15 to 70:30 heptane/ethyl acetate in 30 min) to give the title compound (287 mg, 0.947 mmol, 29.5% yield). MS calculated for C$_7$H$_{14}$Br$_2$NO$_2$ 304.0. found (ESI) m/z 304.2 (M+H)$^+$, retention time 0.56 min.

Intermediate 5

Ethyl 5-fluoro-1-oxo-1,3-dihydrospiro[indene-2,4'-piperidine]-1'-carboxylate

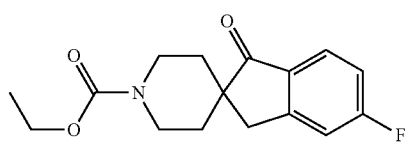 [SMILES: CCOC(=O)N1CCC2(CC1)Cc1cc(F)ccc1C2=O]

To a stirred solution of 5-fluoro-1-indanone (302 mg, 2.013 mmol) and bis-(2-bromo-ethyl)-carbamic acid ethyl ester (610 mg, 2.01 mmol) in DMF (5 mL) at 50° C. was added NaH (121 mg, 5.03 mmol) by small portions. After being stirred at 50° C. for 16 hr, the reaction was cooled to 25° C. The reaction was diluted with 15 mL of ethyl acetate and washed twice with 10 mL of water, dried over Na$_2$SO$_4$ and concentrated in vacuo. The crude product was purified by flash column (gradient of 85:15 to 60:40 heptane/ethyl acetate in 20 min to give the title compound (188 mg, 0.645 mmol, 32.1% yield). MS (ESI) [m/e, (M+H)$^+$]=292.4. HPLC retention time=1.46 minutes (Agilent 1100 HPLC system; 3.0 cm×3.0 mm×3.0 um C8 column; flow rate of 2.0 mL/min; gradient of 5-95% acetonitrile/water with 0.1% formic acid over 2 minutes).

Intermediate 6

5-Fluorospiro[indene-2,4'-piperidin]-1(3H)-one

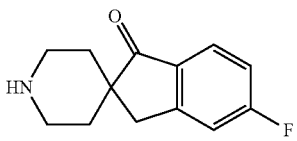 [SMILES: O=C1c2ccc(F)cc2CC12CCNCC2]

To a stirred solution of ethyl 5-fluoro-1-oxo-1,3-dihydrospiro[indene-2,4'-piperidine]-1'-carboxylate (188 mg, 0.645 mmol) in HCl (19.61 µL, 0.645 mmol) was heated at 100° C. over night. The reaction mixture was concentrated to dryness without any further purification to give the title compound (160 mg, 97% yield). MS (ESI) [m/e, (M+H)$^+$]=220.0 (M+H)$^+$, HPLC retention time=0.51 minutes (Agilent 1100 HPLC system; 3.0 cm×3.0 mm×3.0 um C8 column; flow rate of 2.0 mL/min; gradient of 5-95% acetonitrile/water with 0.1% fomic acid over 2 minutes).

Intermediate 7

2,2-Diallyl-5-methoxy-indan-1-one

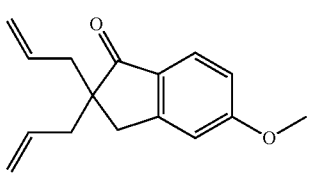 [SMILES: C=CCC1(CC=C)Cc2cc(OC)ccc2C1=O]

To a stirred solution of 5-methoxy-1-indanone (5.24 g, 32.3 mmol) and allyl bromide (9.77 g, 81 mmol) in DMF (80 mL) at ambient temperature was added NaH (3.23 g, 81 mmol) by small portions. After being stirred for 10 min, the reaction mixture was stirred at 50° C. for 8 h, the reaction solution was cooled to ambient temperature, then diluted with 15 mL of EtOAc and washed twice with water (10 mL). The organic phase was dried with anhydrous Na$_2$SO$_4$ and concentrated in vacuo. The crude product was purified by flash column (gradient of 85:15 to 60:40 heptane/ethyl acetate in 20 min) to give the title compound (6.72 g, 27.7 mmol) as colorless liquid. MS (ESI) [m/e, (M+H)$^+$=243.7. Retention time 1.79 min (Agilent 1100 HPLC system; 3.0 cm×3.0 mm×3.0 um C8 column; flow rate of 2.0 mL/min; gradient of 5-95% acetonitrile/water with 0.1% formic acid over 2 minutes).

Intermediate 8

2,2-(5-Methoxy-1-oxo-2,3-dihydro-1H-indene-2,2-diyl)diacetaldehyde

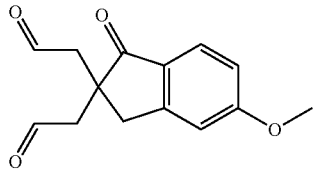 [SMILES: COc1ccc2c(c1)CC(CC=O)(CC=O)C2=O]

A solution 2,2-diallyl-5-methoxy-indan-1-one (600 mg, 2.5 mmol) in $CH_2Cl_2$ (10 mL) was bubbled with $O_3$ at −78° C. for 10 min, then with $N_2$ to remove excess $O_3$. To the reaction solution was added PS-Ph$_3$P (2.75 mg, 4.95 mmol, 1.8 mmol/g) at −78° C. After being stirred at ambient temperature for 1 hr, the reaction mixture was filtered. The filtrate was concentrated in vacuo to give the title compound (535 mg, 2.17 mmol) used without purification in the next step. $^1$H NMR (400 MHz, MeOD) δ ppm 9.61 (s, 2H), 7.64 (d, J=8.6 Hz, 1H), 6.84 (m, 2H), 3.81 (s, 3H), 3.09 (s, 2H), 2.80 (dd, J=69.2 Hz, J=17.7 Hz, 4H).

Intermediate 9

(S)-5-Methoxy-1'-(2-oxopyrrolidin-3-yl)spiro[indene-2,4'-piperidin]-1(3H)-one

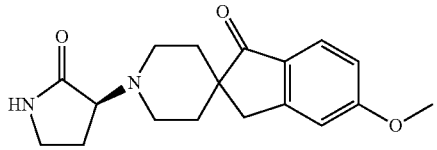 [SMILES: COc1ccc2c(c1)CC1(CCN([C@H]3CCNC3=O)CC1)C2=O]

A solution of 2,2-(5-methoxy-1-oxo-2,3-dihydro-1H-indene-2,2-diyl)diacetaldehyde (100 mg, 0.406 mmol), (S)-3-aminopyrrolidin-2-one (41 mg, 0.41 mmol) and Pd(OH)$_2$ (3 mg, 0.02 mmol) in MeOH (2 mL) was stirred under H$_2$ from a balloon at ambient temperature for 5 h. The reaction mixture was filtered. The filtrate was concentrated. The crude product was purified by HPLC (Column: Sunfire Waters 50×50 mm; mobile: acetonitrile 20%/H$_2$O 80% with 0.1% TFA to acetonitrile 50%/H$_2$O 50% in 10 min gradient, Flow rate: 65 ml/min) to give the title compound (33 mg, 0.11 mmol). MS (ESI) [m/e, (M+H)$^+$=315.1. retention time=0.64 min (Agilent 1100 HPLC system; 3.0 cm×3.0 mm×3.0 um C8 column; flow rate of 2.0 mL/min; gradient of 5-95% acetonitrile/water with 0.1% formic acid over 2 minutes). $^1$H NMR (400 MHz, CDCl$_3$) δ ppm 7.58 (d, J=8.6 Hz, 1H), 7.28 (s, 1H), 6.86 (d, J=8.6 Hz, 1H), 6.80 (s, 1H), 4.23 (t, J=9.1 Hz, 1H), 4.05 (br, s, 1H), 3.48 (m, 1H), 3.82 (s, 3H), 3.73 (s, 1H), 3.46 (m, 2H), 3.30 (br, s, 1H), 2.97 (s, 2H), 2.52 (m, 2H), 2.04 (br, s, 4H).

Intermediate 10

4-(4-Methoxy-3-methyl-benzoyl)-piperidine-1-carboxylic acid tert-butyl ester

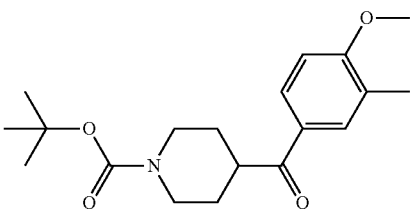 [SMILES: COc1ccc(C(=O)C2CCN(C(=O)OC(C)(C)C)CC2)cc1C]

A stirred solution of 4-(methoxy-methyl-carbamoyl)-piperidine-1-carboxylic acid tert-butyl ester (3.0 g, 11.02 mmol) in 30 mL THF was cooled to 0° C., then (4-methoxy-3-methylphenyl)magnesium bromide (6.21 g, 27.5 mmol) was added dropwise via a syringe under N$_2$ and the reaction mixture was stirred at the same temperature for 1.5 h, then gradually warmed up to room temperature over 1 h when the reaction was judged complete by LCMS. To the reaction mixture was slowly added 40 mL of saturated aqueous NH$_4$Cl then the aqueous solution was extracted with ethyl acetate (2×50 mL). The combined organic phases were washed with brine, dried over Na$_2$SO$_4$ and the solvent was removed to yield the crude product. Purification by flash chromatography gave the title compound as a white solid (1.97 g, 5.62 mmol, 51% yield). MS (ESI) m/z 334.4 (M+H$^+$); HPLC (Novapak 150×3.9 mm C-18 column: mobile phase: 35-90% acetonitrile/water with 0.1% TFA, at 2 mL/min over 2 min.) retention time=1.57 min. $^1$H NMR (400 MHz, CDCL$_3$) δ ppm 1.48 (s, 9H) 1.62-1.91 (m, 4H) 2.27 (s, 3H) 2.78-3.02 (m, 2H) 3.27-3.46 (m, 1H) 3.91 (s, 3H) 4.12-4.27 (m, 2H) 6.87 (d, J=8.59 Hz, 1H) 7.77 (t, J=8.10 Hz, 2H).

Alternative Procedure

To a solution of 4-(methoxy-methyl-carbamoyl)-piperidine-1-carboxylic acid tert-butyl ester (5.0 g, 18.36 mmol) in 50 mL dry THF at ambient temperature was added (4-methoxy-3-methylphenyl)magnesium bromide (55.1 mL, 0.5 M) was added dropwise under N$_2$, the reaction mixture was stirred at the same temperature for 16 hours. The reaction was quenched with saturated sodium sulfate solution (10 mL) and partitioned between brine (150 mL) and 10% isopropyl alcohol/chloroform (200 mL), and the organic layer was removed to yield the crude product. Purification by flash chromatography (silica: 5-35% ethyl acetate/pentane) gave the title compound as a white solid (6.4 g, 19.21 mmol, >99% yield). HPLC (Novapak 150×3.9 mm C-18 column: mobile phase:

10-90% acetonitrile/water with 0.1% TFA, at 2 mL/min over 2 min.) retention time=4.131 min.

Intermediate 11

(4-Methoxy-3-methyl-phenyl)-piperidin-4-yl-methanone

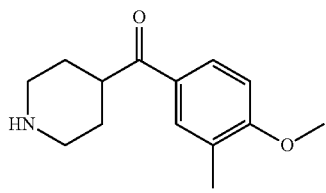 [SMILES: COc1ccc(C(=O)C2CCNCC2)cc1C]

Trifluoroacetic acid (5.55 mL, 72.0 mmol) was added to a solution of 4-(4-methoxy-3-methyl-benzoyl)-piperidine-1-carboxylic acid tert-butyl ester (4.8 g, 14.4 mmol) in dichloromethane (100 mL) and water (10 mL) and allowed to stir for 4 hours at room temperature. The reaction was concentrated under reduced pressure, dissolved in chloroform (200 mL), washed with a saturated sodium bicarbonate solution, dried over $MgSO_4$ and the solvent was evaporated in vacuo to yield the crude product which was used crude in the next step (white solid). Calculated molecular formula=$C_{14}H_{19}NO_2$=233.3130. found MS (ESI) m/e 234.4 (M+H$^+$); $^1$H NMR (400 MHz, CDCl$_3$) δ ppm 1.22 (d, J=6.57 Hz, 6H) 1.64-1.77 (m, 2H) 1.83 (d, J=1.52 Hz, 2H) 1.97-2.08 (br. s, 2H) 2.26 (s, 3H) 2.79 (td, J=12.38, 3.03 Hz, 2H) 3.21 (dt, J=12.63, 3.79 Hz, 2H) 3.33-3.44 (m, J=11.18, 11.18, 3.79, 3.66 Hz, 1H) 3.91 (s, 3H) 4.03 (dq, J=6.32, 6.15 Hz, 0.5H) 6.87 (d, J=8.59 Hz, 1H) 7.83 (dd, J=8.59, 2.53 Hz, 1H) 7.77 (d, J=2.02 Hz, 1H). Analytical RP-HPLC (Novapak 150×3.9 mm C18 column: mobile phase: 10-90% acetonitrile/water with 0.1% TFA, at 2 mL/min over 5 min.) retention time=2.444 min.

Alternative Procedure 1

4-(4-methoxy-3-methyl-benzoyl)-piperidine-1-carboxylic acid tert-butyl ester (6.4 g, 19.21 mmol) was treated with 90% trifluoroacetic acid/water (100 mL) and allowed to stir for 30 minutes at room temperature. The reaction was concentrated under reduced pressure, dissolved in 10% isopropanol/chloroform (200 mL), washed w/ saturated sodium bicarbonate solution, dried over $MgSO_4$ and the solvent was removed to yield the crude product which was used crude in the next step (white solid). Calculated molecular formula=$C_{14}H_{19}NO_2$=233.3130. found MS (ESI) m/e 234.4 (M+H$^+$); $^1$H NMR (400 MHz, chloroform-d) Analytical RP-HPLC (Novapak 150×3.9 mm C18 column: mobile phase: 10-90% acetonitrile/water with 0.1% TFA, at 2 mL/min over 5 min.) retention time=2.514 min.

Alternative Procedure 2

A suspension of 1-(4-(4-methoxy-3-methylbenzoyl)piperidin-1-yl)ethanone (5.45 g, 19.8 mmol) in 6 N HCl (40 mL) was heated to reflux for 12 h then concentrated in vacuo to a light purple solid. The material was taken up in ~100 mL MeOH with heating and sonication, concentrated in vacuo to ~25 mL, added diethyl ether (~200 mL) to form white precipitate and a purple aqueous layer. The aqueous layer was removed via a pipet and concentrated in vacuo. The suspension was decanted through filter to recover a white solid (1.30 g). The aqueous material was concentrated in vacuo to form a purplish oil which was taken up in diethyl ether and the resulting suspension was filtered (0.82 g). The filtrate was concentrated in vacuo to a purple oil. The solid material was confirmed to be the title compound. Calculated molecular formula=$C_{14}H_{19}NO_2$=233.31. found MS (ESI) m/e 233.9 (M+H$^+$)

Intermediate 12

4-Phenylsulfanylcarbonyl-piperidine-1-carboxylic acid tert-butyl ester

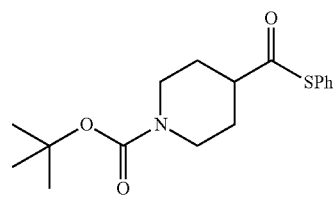

To a solution of piperidine-1,4-dicarboxylic acid mono-tert-butyl ester (5.0 g, 21.81 mmol), diisopropylethylamine (5.64 g, 43.6 mmol) in 40 mL of Dmolecular formula were added HATU (9.2 g, 24.0 mmol) and benzenethiol (2.7 g, 24.0 mmol). The reaction mixture was stirred at ambient temperature for 15 hours. The reaction mixture was quenched with water (50 mL), then extracted with DCM (50 mL). The combined organic layers were washed with water and saturated aqueous NaCl solution, dried over $Na_2SO_4$, filtered and concentrated in vacuo to yield the crude product. (6.85 g, 20.25 mmol) as a yellow oil. MS (ESI) m/z 321.8 (M+H$^+$); HPLC (Novapak 150×3.9 mm C-18 column: mobile phase: 35-90% acetonitrile/water with 0.1% TFA, at 2 mL/min over 2 min.) retention time=1.66 min.

Intermediate 13 methanesulfonic acid (S)-2-oxo-pyrrolidin-3-yl ester

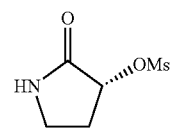

To a stirred mixture of (R)-3-hydroxypyrrolidin-2-one (19.5 g, 193 mmol) and triethylamine (90 mL) at 0° C. was added a solution of methanesulfonic anhydride (33.6 g, 193 mmol) in DCM (90 mL) over 35 minutes maintaining an internal temperature below 5° C. After stirring at 0° C. for 30 min the reaction was allowed to warm to room temperature and stirred for an additional 18 h and then concentrated in vacuo. This material was combined with 12 g crude material from previous batches and then purified via silica gel chromatography to yield 35 g of the title compound.

Intermediate 14 methanesulfonic acid (S)-2-oxo-pyrrolidin-3-yl ester

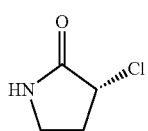

To a 10° C. solution of (S)-3-hydroxypyrrolidin-2-one (120 g, 1.19 mol) in pyridine (38.4 mL, 475 mmol) and dichloromethane (3 L) at 10° C. was added thionyl chloride (173 mL, 2.37 mol) dropwise and the reaction was stirred for an additional 3 h. The reaction was concentrated in vacuo, taken up in dichloromethane and purified by filtering through a plug of silica gel, eluting with 10 L ethyl acetate. The material was concentrated in vacuo to approximately 1 L, diluted with 1.5 L diethyl ether and heated gently for 15 min. The suspension was filtered, washed with diethyl ether (500 mL), dried in vacuo, taken up in diethyl ether (1 L) and heated at 45° C. then filtered to afford 105 g of the title compound as a white solid.

Intermediate 15

Methanesulfonic acid 2-oxo-piperidin-3-yl ester

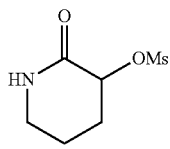

To a suspension of 3-hydroxy-piperidin-2-one (500 mg, 4.34 mmol, 1.0 eq) and triethylamine (0.908 mL, 6.51 mmol, 1.5 eq) in dichloromethane (3 mL) at 0° C. was added dropwise methanesulfonyl chloride (497 mg, 4.34 mmol, 1.0 eq) dissolved in dichloromethane (1 mL). The reaction was complete within 30 min as judged by LCMS. An orange precipitate was filtered, redissolved in dichloromethane and purified by column chromatography (MeOH/CH$_2$Cl$_2$) to give the title compound as a white waxy solid (204 mg, 1.056 mmol, 24.3% yield). $^1$H NMR (400 MHz, chloroform-d) δ ppm 5.78 (br. s, 1H) 4.94-5.05 (m, 1H) 3.30-3.44 (m, 2H) 3.27 (s, 3H)

2.24-2.37 (m, 1H) 2.08-2.21 (m, 1H) 1.98-2.08 (m, 1H) 1.79-1.96 (m, 1H). MS (m/z, MH+): 193.7

Intermediate 16

3-[4-(4-Methoxy-benzoyl)-piperidin-1-yl]-2-one

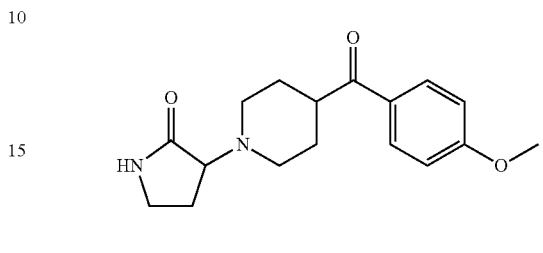

In a 1 L round bottom flask was added methanesulfonic acid (S)-2-oxo-pyrrolidin-3-yl ester (prepared according to procedure in Eur. Pat. Appl., 257602, 2 Mar. 1988) (95 mmol, 17 g) and (4-methoxy-phenyl)-piperidin-4-yl-methanone (95 mmol, 20.8 g) in DIEA (379 mmol, 66.3 mL). The reaction mixture was heated at 85° C. for 18 hours. The top layer was decanted off and silica gel flash column chromatography was performed on the remaining residue eluting with ethyl acetate to 20% MeOH/ethyl acetate to provide the title compound as a light beige solid (13 g, 49% yield). Calculated MS=302.4. found MS (ESI) m/e 303.4 (M+H$^+$); $^1$H NMR (400 MHz, MeOD) δ ppm 1.69-1.89 (m, 4H) 2.11-2.18 (m, 1H) 2.18-2.30 (m, 1H) 2.50 (td, J=11.29, 3.01 Hz, 1H) 2.78 (td, J=11.54, 3.01 Hz, 1H) 2.84-2.91 (m, 1H) 3.13 (d, J=11.54 Hz, 1H) 3.24-3.41 (m, 7H) 3.49 (t, J=8.78 Hz, 1H) 7.01 (d, J=9.00 Hz, 2H) 7.96 (d, J=9.03 Hz, 2H); HPLC (Novapak 150×3.9 mm C$_{18}$ column: mobile phase: 10-90% acetonitrile/water with 0.1% TFA, at 2 mL/min over 5 min.) retention time=2.305 min.

Intermediate 17

4-(4-Methoxy-benzoyl)-[1,3']bipiperidinyl-2'-one

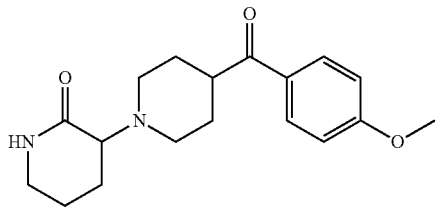 [SMILES: COc1ccc(C(=O)C2CCN(C3CCCNC3=O)CC2)cc1]

To a solution of methanesulfonic acid 2-oxo-piperidin-3-yl ester (250 mg, 1/294 mmol, 1.0 eq) and (4-methoxy-phenyl)-piperidin-4-yl-methanone (312 mg, 1.423 mmol, 1.1 eq) in acetonitrile (2.5 mL) was added diisopropylethylamine (351 mg, 0.475 mL, 2.1 eq) and the reaction was heated at 85° C. for 3 hours. The reaction was cooled to room temperature and the solvent evaporated in vacuo. The resulting oily residue was purified by silica gel column chromatography (MeOH/CH$_2$Cl$_2$) to give the title compound as a clear oil (142 mg, 0.449 mmol, 34.7% yield). $^1$H NMR (400 MHz, DMSO-d$_6$) δ ppm 7.95 (d, J=9.09 Hz, 2H) 7.39-7.43 (br. s, 1H) 7.04 (d, J=8.59 Hz, 2H) 3.84 (s, 3H) 3.23-3.33 (m, 2H) 2.97-3.14 (m, 4H) 2.74-2.85 (m, 2H) 1.75-1.91 (m, 2H) 1.57-1.75 (m, 4H) 1.47-1.54 (m, 2H). MS (m/z, MH+): 316.8

Intermediate 18

(S)-3-[4-(4-Methoxy-benzoyl)-piperidin-1-yl]-pyrrolidin-2-one

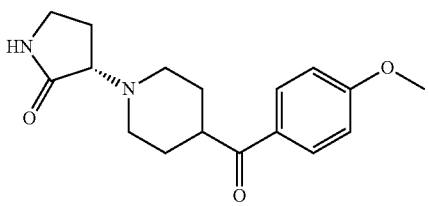 [SMILES: COc1ccc(C(=O)C2CCN([C@H]3CCNC3=O)CC2)cc1]

To a suspension of (4-methoxyphenyl)(piperidin-4-yl) methanone (34 g, 155 mmol) and (R)-2-oxopyrrolidin-3-yl methanesulfonate (34.7 g, 194 mmol) in acetonitrile (388 mL) at room temperature was added DIPEA (108 mL, 620 mmol) and the reaction was heated to 60 C for 29 h then allowed to cool to room temperature and stirred for an additional 24 h. The reaction mixture was concentrated in vacuo to afford a waxy solid which was taken up in ethyl acetate (300 mL) and sonicated. The mixture was filtered and the resulting white solid was washed with ethyl acetate (200 mL) to yield 21.05 g. The combined filtrates were concentrated and purified via silica gel chromatography (330 g isco 0.01% NH$_4$OH 5-10% MeOH/ethyl acetate). Pure fractions were combined, concentrated in vacuo and then taken up in ethyl acetate (80-100 mL) and stirred. A white precipitate formed that was collected by filtration. The filtrate was concentrated to a gold oil, taken up in ethyl acetate to afford a white precipitate that was collected by filtration. A total of 27.7 g of the title material was obtained as a white solid. Calculated MS=302.4. found MS (ESI) m/e 303.4 (M+H$^+$)

Intermediate 19

(R)-3-[4-(4-Methoxy-3-methyl-benzoyl)-piperidin-1-yl]-pyrrolidin-2-one

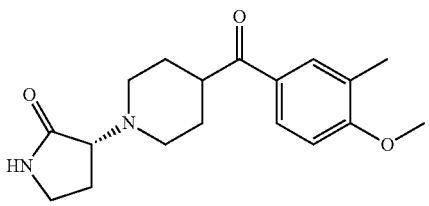 [SMILES: COc1ccc(C(=O)C2CCN([C@@H]3CCNC3=O)CC2)cc1C]

In a 1 L round bottom flask was added methanesulfonic acid (S)-2-oxo-pyrrolidin-3-yl ester (prepared according to procedure in Eur. Pat. Appl., 257602, 2 Mar. 1988) (18.75 mmol, 3.36 g) and (4-methoxy-3-methyl-phenyl)-piperidin-4-yl-methanone (18.75 mmol, 4.37 g) in DIEA (75 mmol, 13.1 mL) and acetonitrile (100 mL). The reaction mixture was heated at 85° C. for 4 hours. The reaction was evaporated under a vacuum and silica gel flash column chromatography was performed on the remaining residue eluting with ethyl acetate to 20% MeOH/ethyl acetate to provide the title compound as a white solid (4 g, 67.4% yield). Calculated for C$_{18}$H$_{24}$N$_2$O$_3$ MS=316.4036. found MS (ESI) m/e 317.1863 (M+H$^+$); $^1$H NMR (400 MHz, MeOD) δ ppm 1.69-1.89 (m, 4H) 2.08-2.21 (m, 1H) 2.24-2.30 (m, 1H) 2.44-2.56 (m, 1H) 2.73-2.84 (m, 1H) 2.84-2.92 (m, 1H) 3.08-3.17 (m, 1H) 3.30-3.42 (m, 6H) 3.45-3.54 (m, 1H) 3.90 (s, 3H) 6.95-7.04 (m, 1H) 7.72-7.81 (m, 1H) 7.83-7.90 (m, 1H); analytical RP-HPLC retention time=4.67 min.

Intermediate 20

(S)-3-[4-(4-Methoxy-3-methyl-benzoyl)-piperidin-1-yl]-pyrrolidin-2-one

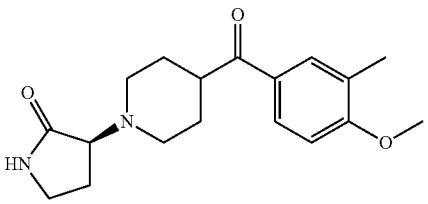 [SMILES: COc1ccc(C(=O)C2CCN([C@H]3CCNC3=O)CC2)cc1C]

In a 1 L round bottom flask was added methanesulfonic acid (R)-2-oxo-pyrrolidin-3-yl ester (19.72 mmol, 3.53 g) (4-methoxy-3-methyl-phenyl)-piperidin-4-yl-methanone (19.72 mmol, 4.60 g) in DIEA (79 mmol, 13.8 mL) and acetonitrile (75 mL). The reaction mixture was heated at 85° C. for 13 hours. The reaction was evaporated under a vacuum and silica gel flash column chromatography was performed on the remaining residue eluting with 5% MeOH/ethyl acetate to 20% MeOH/ethyl acetate to provide the title compound as a white solid (4.6 g, 73.7% yield). Calculated for C$_{18}$H$_{24}$N$_2$O$_3$ MS=316.4036. found MS (ESI) m/e 317.1876 (M+H$^+$); $^1$H NMR (400 MHz, CDCl$_3$) δ ppm 1.82-1.97 (m, 4H) 2.15-2.36 (m, 5H) 2.48-2.59 (m, 1H) 2.90-3.04 (m, 2H) 3.07-3.15 (m, 1H) 3.23-3.44 (m, 3H) 3.48-3.56 (m, 1H) 3.91 (s, 3H) 6.08-6.13 (br. s, 1H) 6.85 (s, 1H) 7.77 (s, 1H) 7.83 (dd, J=8.53, 2.01 Hz, 1H), analytical RP-HPLC (Novapak 150× 3.9 mm C18 column: mobile phase: 10-90% acetonitrile/water with 0.1% TFA, at 2 mL/min over 5 min.) retention time=2.557 min.

Intermediate 21

3-[4-(4-Fluoro-benzoyl)-piperidin-1-yl]-pyrrolidin-2-one

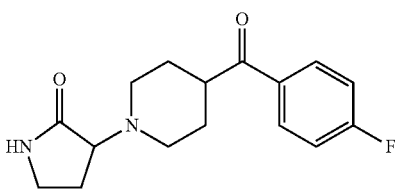 [SMILES: O=C(c1ccc(F)cc1)C1CCN(C2CCNC2=O)CC1]

To a 10 mL microwave vial was added methanesulfonic acid (S)-2-oxo-pyrrolidin-3-yl ester (4.97 mmol, 890 mg) and (4-fluoro-phenyl)-piperidin-4-yl-methanone hydrochloride (4.97 mmol, 1.21 g) in DIEA (24.8 mmol, 5 mL) was heated to 85° C. for 105 min. The DIEA was decanted and flash column chromatography (silica) was performed eluting with ethyl acetate to 20% MeOH/ethyl acetate afforded the title compound (112 mg, 7.8% yield). MS (ESI) m/e 291.2

(M+H⁺), calculated 290.33; HPLC (Novapak 150×3.9 mm C18 column: mobile phase: 10-90% acetonitrile/water with 0.1% TFA, at 2 mL/min over 5 min.) retention time=2.303 min.

Intermediate 22

3-[4-(4-Chloro-benzoyl)-piperidin-1-yl]-pyrrolidin-2-one

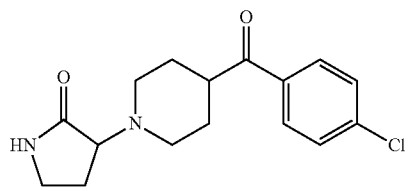 [SMILES: O=C(c1ccc(Cl)cc1)C1CCN(C2CCNC2=O)CC1]

A 10 mL microwave vial containing methanesulfonic acid (S)-2-oxo-pyrrolidin-3-yl ester (0.56 mmol, 100 mg) and (4-chloro-phenyl)-piperidin-4-yl-methanone (0.56 mmol, 125 mg) in DIEA (2.8 mmol, 0.5 mL) was heated to 85° C. for 105 min. The diisopropylethylamine was decanted off and flash column chromatography (silica) was performed eluting with ethyl acetate to 20% MeOH/ethyl acetate afforded the title compound (53 mg, 31% yield). MS (ESI) m/e 307.3 (M+H⁺), calculated 306.2; HPLC (Novapak 150×3.9 mm C18 column: mobile phase: 10-90% acetonitrile/water with 0.1% TFA, at 2 mL/min over 5 min.) retention time=2.506 min.

Intermediate 23

5-methoxy-1'-(2-oxopyrrolidin-3-yl)spiro[indene-2,4'-piperidin]-1 (3H)-one

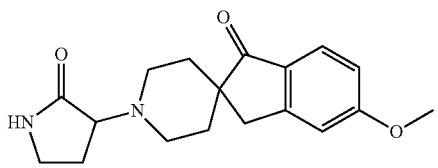 [SMILES: COc1ccc2c(c1)CC1(CCN(C3CCNC3=O)CC1)C2=O]

To a 250 mL round bottom flask was added methanesulfonic acid (S)-2-oxo-pyrrolidin-3-yl ester (2) (4.76 mmol, 852 mg) and 5-methoxyspiro[indene-2,4'-piperidin]-1(3H)-one (3) (4.32 mmol, 1.00 g) in DIEA (17.29 mmol, 3.02 mL) and acetonitrile (20 mL). The solution was then heated to 85° C. for 90 min. The reaction was concentrated in vacuo and flash column chromatography (silica) was performed eluting with ethyl acetate to 20% MeOH/ethyl acetate afforded the title compound (1.05 g, 77% yield). Calculated MS=306.2. found MS (ESI) m/e 307.3 (M+H⁺); HPLC (Novapak 150× 3.9 mm C18 column: mobile phase: 10-90% acetonitrile/water with 0.1% TFA, at 2 mL/min over 5 min.) retention time=2.253 min.

Intermediate 24

2-(bromomethyl)-6-chlorobenzonitrile

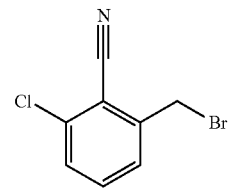 [SMILES: N#Cc1c(Cl)cccc1CBr]

To a solution of 2-chloro-6-methylbenzonitrile (2.0 g, 13 mmol) and N-bromosuccinimide (2.6 g, 15 mmol) in carbon tetrachloride (20 mL) was added azobisisobutyronitrile (0.20 g, 1.2 mmol). The mixture was refluxed for 3 h and then cooled, diluted with dichloromethane and washed with water and brine. The organic phase was dried over anhydrous sodium sulfate, filtered, and concentrated in vacuo. The resultant oil was purified via flash column chromatography (ethyl acetate:hexane, 0:100 to 30:70) to yield white solid product (1.4 g, 46%). ¹H NMR (400 MHz, CDCl₃) δ 7.43-7.59 (m, 3H), 4.64 (s, 2H).

Intermediate 25

2-(3-bromo-2-oxopyrrolidin-1-yl)acetonitrile

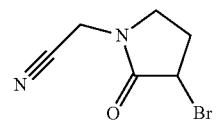

To a solution of 2,4-dibromobutanoyl chloride (3.6 g, 14 mmol) in DCM (100 mL) and 2-aminoacetonitrile hydrochloride (1.3 g, 14 mmol) was added triethylamine (5.7 mL, 41 mmol) at 0° C. The mixture was stirred at ambient temperature for 24 h. To the resulting material was added methylene chloride and it was washed with water and then brine. The combined organic layers were dried over sodium sulfate, filtered, and the solvent was removed in vacuo. The resulting residue was taken up in toluene (130 mL) and at 0° C. was added sodium hydride (545 mg, 13.6 mmol, 60% in mineral oil) portion-wise over 20 minutes. The reaction was stirred at ambient temperature for 60 h. The mixture was diluted with ethyl acetate and then poured into ice water. The organic layer was separated, washed with brine, dried over sodium sulfate, and purified via flash column chromatography (ethyl acetate: hexane, 0:100 to 100:0) to provide a brown oil (730 mg, 26% yield). ¹H NMR (400 MHz, CDCl₃) δ 4.37-4.50 (m, 2H), 4.10-4.28 (m, 1H), 3.70 (dq, J=7.6, 2.0 Hz, 1H), 3.51-3.59 (m, 1H), 2.65-2.79 (m, J=7.0 Hz, 1H), 2.33-2.50 (m, 1H).

Intermediate 26

2-(3-(4-(4-methoxybenzoyl)piperidin-1-yl)-2-oxopyrrolidin-1-yl)acetonitrile

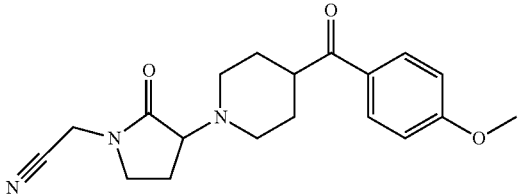 [SMILES: COc1ccc(C(=O)C2CCN(C3CCN(CC#N)C3=O)CC2)cc1]

To a solution of 2-(2-bromo-5-oxopyrrolidin-1-yl)acetonitrile (730 mg, 3.6 mmol) and (4-methoxyphenyl)(piperidin-4-yl)methanone hydrochloride (920 mg, 3.6 mmol) in acetonitrile (4 mL) was added triethylamine (1.5 mL, 11 mmol). The mixture was microwave at 130° C. for 12 minutes. The solvent was removed in vacuo and the residue was taken up in methylene chloride and water. The organic layer was purified via flash column chromatography (ethyl acetate:hexane, 10:90 to 100:0) to provide slightly yellow oil (950 mg, 74% yield). $^1$H NMR (400 MHz, CDCl$_3$) δ 7.94 (d, J=8.5 Hz, 2H), 6.96 (d, J=8.5 Hz, 2H), 4.22-4.39 (m, 2H), 3.90 (s, 3H), 3.57 (dt, J=22.6, 9.0 Hz, 2H), 3.40-3.51 (m, J=8.5 Hz, 1H), 3.23-3.39 (br s, 1H), 2.93-3.20 (m, 3H), 2.33-2.61 (m, 2H), 2.13-2.31 (m, 1H), 1.83-2.03 (m, 4H). HRMS calculated for C$_{13}$H$_{23}$N$_3$O$_3$ 342.1818. found (ESI, [M+H]$^+$), 342.1830.

Intermediate 27

2-(3-(4-(4-methoxybenzoyl)piperidin-1-yl)-2-oxopyrrolidin-1-yl)acetimidamide hydrochloride

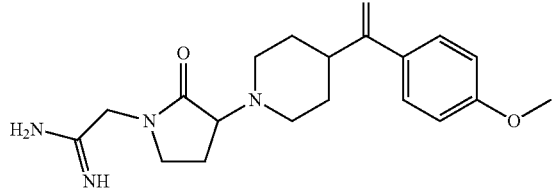

To a solution of 2-(3-(4-(4-methoxybenzoyl)piperidin-1-yl)-2-oxopyrrolidin-1-yl)acetonitrile (690 mg, 2.0 mmol) in methanol (15 mL) was added sodium methoxide (0.046 mL, 0.20 mmol, 25%) and the mixture was stirred at ambient temperature for 2 h. Ammonium chloride (120 mg, 2.3 mmol) was added and the mixture was stirred at ambient temperature for 60 h. The reaction mixture was concentrated in vacuo, ethyl acetate in heptane (40%) was added, stirred at ambient temperature for 1 h then filtrated. the resulting solid was washed with ether to give a pale solid (800 mg, 100% yield). MS m/z 342.4 (M+1), retention time 0.79

Intermediate 28

2-(3-(4-(4-methoxybenzoyl)piperidin-1-yl)-2-oxopyrrolidin-1-yl)acetonitrile

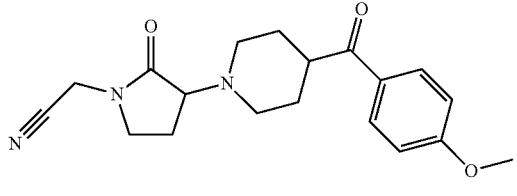 [SMILES: COc1ccc(C(=O)C2CCN(C3CCN(CC#N)C3=O)CC2)cc1]

To a solution of 3-[4-(4-methoxy-benzoyl)-piperidin-1-yl]-pyrrolidin-2-one (1.65 mmol, 500 mg) and chloroacetonitrile (1.65 mmol, 0.125 g) in THF (30 mL) and DMF (5 mL) was added sodium hydride (60%, 2.48 mmol, 0.099 g) and heated to 70° C. for 30 min. The reaction was allowed to cool to ambient temperature and dried under vacuum. Flash column chromatography (silica) was performed eluting with ethyl acetate to 20% MeOH/ethyl acetate and provided the title compound as an off-white residue (125 mg, 22.1% yield). Calculated MS=341.4. found MS (ESI) m/e 342.9 (M+H$^+$); HPLC (Novapak 150×3.9 mm C18 column: mobile phase: 10-90% acetonitrile/water with 0.1% TFA, at 2 mL/min over 5 min.) retention time=2.472 min.

Intermediate 29

{(S)-3-[4-(4-Methoxy-3-methyl-benzoyl)-piperidin-1-yl]-2-oxo-pyrrolidin-1-yl}-acetonitrile

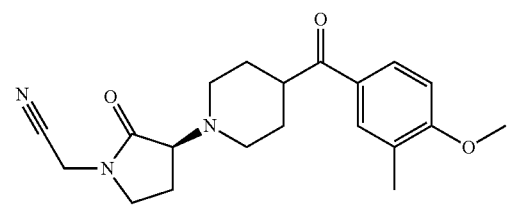 [SMILES: COc1ccc(C(=O)C2CCN([C@H]3CCN(CC#N)C3=O)CC2)cc1C]

To a solution of (S)-3-[4-(4-methoxy-3-methyl-benzoyl)-piperidin-1-yl]-pyrrolidin-2-one (6.32 mmol, 2.0 g) and bromoacetonitrile (18.96 mmol, 2.275 g) in THF (60 mL) at 0° C. was added sodium hydride (60%, 18.96 mmol, 0.76 g) and allowed to stir under N$_2$ for 1 hour. Allowed to warm to ambient temperature and chloroacetonitrile (2 mL) was added. After 30 min the reaction was cooled to 0° C. and quenched with saturated ammonium chloride solution. Flash column chromatography (silica) was performed eluting with 3% MeOH/ethyl acetate to 15% MeOH/ethyl acetate and provided the title compound as an red-brown foam (1.6 g, 71.2% yield). Calculated molecular formula=C$_{20}$H$_{25}$N$_3$O$_3$=355.4406. found MS (ESI) m/e 356.6 (M+H$^+$); analytical RP-HPLC (Novapak 150×3.9 mm C18 column: mobile phase: 10-90% acetonitrile/water with 0.1% TFA, at 2 mL/min over 5 min.) retention time=2.831 min.

Intermediate 30

{(R)-3-[4-(4-Methoxy-3-methyl-benzoyl)-piperidin-1-yl]-2-oxo-pyrrolidin-1-yl}-acetonitrile

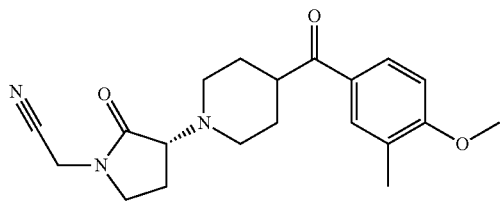 [SMILES: COc1ccc(C(=O)C2CCN([C@@H]3CCN(CC#N)C3=O)CC2)cc1C]

To a solution of (R)-3-[4-(4-methoxy-3-methyl-benzoyl)-piperidin-1-yl]-pyrrolidin-2-one (6.32 mmol, 2.0 g) and chloroacetonitrile (6.32 mmol, 0.48 g) in THF (50 mL) was added sodium hydride (60%, 9.48 mmol, 0.38 g) and heated to 70° C. for 30 min. The reaction was allowed to cool to ambient temperature and dried under vacuum. Flash column chromatography (silica) was performed eluting with ethyl acetate to 20% MeOH/ethyl acetate and provided the title compound as an off-white residue (1.1 g, 49% yield). Calculated molecular formula=$C_{20}H_{25}N_3O_3$=355.4406. found MS (ESI) m/e 356.1978 (M+H$^+$); analytical RP-HPLC (Novapak 150×3.9 mm C18 column: mobile phase: 10-90% acetonitrile/water with 0.1% TFA, at 2 mL/min over 5 min.) retention time=2.591 min.

Intermediate 31

2-{3-[4-(4-Methoxy-benzoyl)-piperidin-1-yl]-2-oxo-pyrrolidin-1-yl}-acetamidine

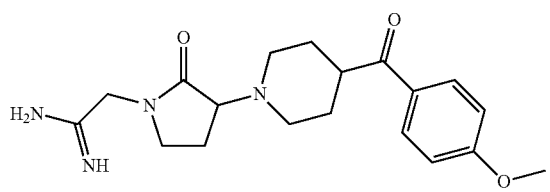 [SMILES: COc1ccc(C(=O)C2CCN(C3CCN(CC(=N)N)C3=O)CC2)cc1]

To a solution of 2-(3-(4-(4-methoxybenzoyl)piperidin-1-yl)-2-oxopyrrolidin-1-yl)acetonitrile (125 mg, 0.366 mmol) in methanol (4 mL) was added sodium methoxide (2 mg, 0.037 mmol) and stirred at ambient temperature for 2 h. Ammonium chloride (23.5 mg, 0.439 mmol) was added and the mixture was stirred at ambient temperature for 16 h. The reaction mixture was concentrated then ethyl acetate in pentane (1:1) was added and stirred at ambient temperature for 1 h. Filtration provided a solid that was washed with ether to give a pale solid (130 mg, 100%). MS m/z 360.0 (M+1), HPLC (Novapak 150×3.9 mm C18 column: mobile phase: 10-90% acetonitrile/water with 0.1% TFA, at 2 mL/min over 5 min.) retention time=2.139 min.

Intermediate 32

2-{(S)-3-[4-(4-Methoxy-3-methyl-benzoyl)-piperidin-1-yl]-2-oxo-pyrrolidin-1-yl}-acetamidine

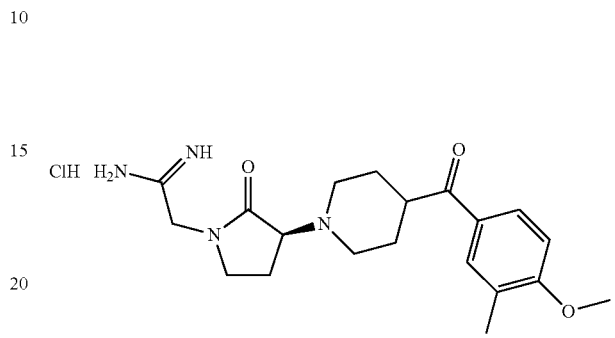

To a solution of {(S)-3-[4-(4-methoxy-3-methyl-benzoyl)-piperidin-1-yl]-2-oxo-pyrrolidin-1-yl}-acetonitrile (1.60 g, 4.5 mmol) in methanol (40 mL) was added sodium methoxide (511 mg, 9.45 mmol) and stirred at 40° C. for 3 hours. Ammonium chloride (265 mg, 9.45 mmol) was added and the mixture was stirred at 40° C. temperature for 2 h. The reaction mixture was concentrated then chloroform in ethyl acetate (volume of 1:2) was added and stirred at ambient temperature for 1 h. Centrifugation at 1500 rpm for 30 min. provided a beige solid (1.8 g, 98%). HRMS calculated for $C_{20}H_{29}N_4O_3Cl$ 372.4712. found (ESI, [M+H]$^+$). found 373.2242. $^1$H NMR (400 MHz, CDCl$_3$-d) δ ppm 1.75-1.98 (m, 5H) 2.19-2.40 (m, 7H) 2.48-2.65 (m, 1H) 2.76-3.01 (m, 3H) 3.16-3.36 (m, 3H) 3.46-3.64 (m, 3H) 3.81-3.94 (m, 6H) 4.34 (d, J=16.56 Hz, 1H) 4.52 (d, J=16.56 Hz, 1H) 6.84 (d, J=8.53 Hz, 1H) 7.28 (s, 1H) 7.70-7.87 (m, 3H) 8.51 (s, 1H), HPLC (Novapak 150×3.9 mm C18 column: mobile phase: 10-90% acetonitrile/water with 0.1% TFA, at 2 mL/min over 5 min.) retention time=2.385 min.

Intermediate 33

Toluene-4-sulfonic acid 7-oxo-cyclohepta-1,3,5-trienyl ester

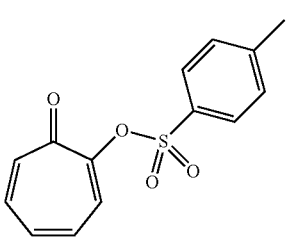 [SMILES: Cc1ccc(S(=O)(=O)Oc2cccccc2=O)cc1]

The title material was synthesized according to the conditions found in *Chem. Pharm. Bull.* 54(5), 703, (2006).

Intermediate 34

Ethyl 2-(2,4-dibromobutanamido)acetate

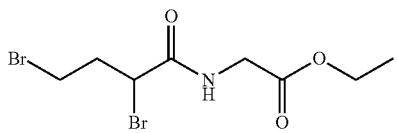

To a stirred mixture of ethyl 2-aminoacetate hydrochloride (1.568 g, 11.24 mmol) in dichloromethane (9 mL) and water (2 mL) at 0° C. was added a solution of 2,4-dibromobutanoyl chloride (3.0 g, 10.21 mmol) in dichloromethane (2 mL). A solution of sodium hydroxide in water (11.5 M, 2 mL) was then added slowly. The reaction was stirred 1 hour at 0° C. and then 15 minutes at room temperature. The reaction was then treated with dichloromethane (40 mL) and water (25 mL). The layers were separated, and the organic layer was brine-washed, dried over sodium sulfate, filtered, concentrated down, and dried under vacuum to afford the crude title racemic compound (3.165 g in 90% purity, 84% yield) as a clear oil. $^1$H NMR (400 MHz, chloroform-d) δ ppm 6.81 (br s, 1H), 4.58 (dd, J=8.84, 4.80 Hz, 1H), 4.21-4.31 (m, 2H), 4.07 (d, J=5.56 Hz, 2H), 3.51-3.63 (m, 2H), 2.62-2.75 (m, 1H), 2.44-2.57 (m, 1H), 1.28-1.36 (m, 3H).

Intermediate 35

Ethyl 2-(3-bromo-2-oxopyrrolidin-1-yl)acetate

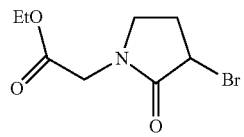 [SMILES: CCOC(=O)CN1CCC(Br)C1=O]

To a stirred solution of crude ethyl 2-(2,4-dibromobutanamido)acetate (2.847 g, 8.60 mmol) in benzene (8.6 mL) at 5° C. was added portionwise a 60% mineral oil dispersion (344 mg) of sodium hydride (206 mg, 8.60 mmol) over 20 minutes. The reaction was stirred an additional 10 minutes before being poured onto ice water and diluted with ethyl acetate. The layers were separated. The organic phase was brine-washed, dried over sodium sulfate, filtered, concentrated down, and dried. The mixture of starting dibromide and product was purified by eluting through a silica gel column with a 0 to 100% ethyl acetate/heptane gradient to afford the title racemic compound (523 mg, 24% yield) as a clear oil. MS (ESI) [m/e, (M+H)$^+$]=251.5. $^1$H NMR (400 MHz, chloroform-d) δ ppm 4.46 (dd, J=7.07, 3.03 Hz, 1H), 3.96-4.28 (m, 4H), 3.63-3.72 (m, 1H), 3.43-3.53 (m, 1H), 2.63-2.76 (m, 1H), 2.34-2.43 (m, 1H), 1.26-1.34 (m, 3H).

Intermediate 36

Ethyl 2-(3-(4-(4-methoxybenzoyl)piperidin-1-yl)-2-oxopyrrolidin-1-yl)acetate

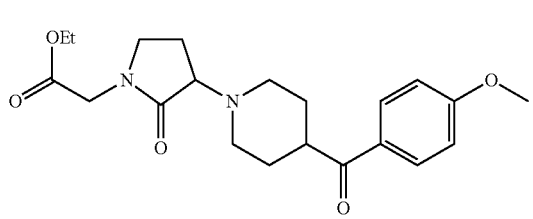 [SMILES: COc1ccc(C(=O)C2CCN(C3CCN(CC(=O)O)C3=O)CC2)cc1]

(4-Methoxyphenyl)(piperidin-4-yl)methanone hydrochloride (524 mg, 2.05 mmol) was stirred at room temperature with triethylamine (0.657 mL, 477 mg, 4.71 mmol) in acetonitrile (80 mL). A solution of ethyl 2-(3-bromo-2-oxopyrrolidin-1-yl)acetate (513 mg, 2.05 mmol) in acetonitrile (20 mL) was added to the mix. The reaction was stirred 3 hours at 40° C. and then overnight at 50° C. After 24 hours the reaction was not complete and the reaction was stirred an additional 48 hours at 70° C. then allowed to cool to room temperature. The solvents were removed in vacuo. The crude orange solid was eluted through a silica gel column with a 0 to 10% methanol/dichloromethane gradient to afford the title racemic compound (730 mg, 87% yield, 95% purity) as a thick amber oil. MS (ESI) [m/e, (M+H)$^+$]=389.5. $^1$H NMR (400 MHz, chloroform-d) δ ppm 7.90-7.95 (m, 2H), 6.91-6.96 (m, 2H), 4.17-4.24 (m, 2H), 3.95-4.17 (m, 2H), 3.88 (s, 3H), 3.56-3.64 (m, 1H), 3.36-3.50 (m, 2H), 3.18-3.29 (m, 1H), 3.04-3.13 (m, 1H), 2.93-3.04 (m, 2H), 2.41-2.56 (m, 1H), 2.20-2.35 (m, 1H), 2.04-2.19 (m, 1H), 1.80-1.95 (m, 4H), 1.26-1.32 (m, 3H).

Intermediate 37

2-(3-(4-(4-Methoxybenzoyl)piperidin-1-yl)-2-oxopyrrolidin-1-yl)acetic acid

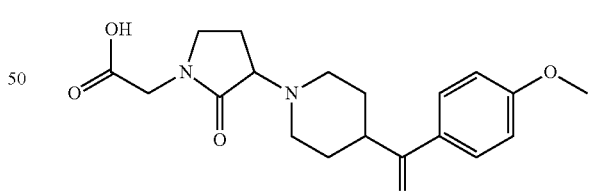

To a solution of ethyl 2-(3-(4-(4-methoxybenzoyl)piperidin-1-yl)-2-oxopyrrolidin-1-yl)acetate (727 mg, 1.778 mmol) in ethanol (36 mL) was added a 2 N aqueous NaOH solution (1.8 mL). The mixture was stirred 1 hour at room temperature. The reaction was then neutralized to pH 7 with 1 N HCl. The solvents were removed in vacuo, then azeotroped 3 times with dichloromethane. The light yellow foamy solid was dried under high vacuum to afford the title racemic product (835 mg). MS (ESI) [m/e, (M+H)$^+$]=360.9. $^1$H NMR (400 MHz, DMSO-d$_6$) δ ppm 7.89-8.01 (m, 2H), 6.96-7.11 (m, 2H), 3.85 (s, 3H), 3.46-3.68 (m, 2H), 3.13-3.46 (m, 5H), 2.93-3.04 (m, 1H), 2.61-2.84 (m, 1H), 2.30-2.42 (m, 1H), 1.95-2.11 (m, 1H), 1.81-1.95 (m, 1H), 1.64-1.78 (m, 2H), 1.44-1.63 (m, 2H).

Intermediate 38

5,6-dihydrothiazolo[2,3-c][1,2,4]triazol-3-amine hydrobromide

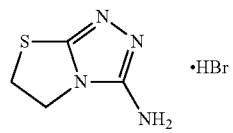

The title compound was prepared in accordance with the procedure exemplified in the following citation: On triazoles XLVIII [1]. Synthesis of isomeric aminothiazolo[1,2,4]triazole, amino[1,2,4]triazolo[1,3]thiazine and -[1,3]thiazepine derivatives. Prauda, Ibolya; Reiter, Jozsef. Egis Pharmaceuticals Ltd., Budapest, Hung. *Journal of Heterocyclic Chemistry* (2003), 40(5), 821-826.

Intermediate 39

Ethyl 6-formyl-3,4-dihydro-2H-pyran-5-carboxylate

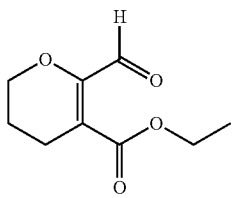

A mixture of ethyl 6-methyl-3,4-dihydro-2H-pyran-5-carboxylate (6.0 g, 35.3 mmol) and selenium dioxide (4.3 g, 38.8 mmol) was stirred in acetic acid (141 mL) 5 hours at 110° C. The reaction was then cooled to room temperature and the solids were removed by filtration. The filtrate was concentrated down and purified by silica gel chromatography with 0 to 15% ethyl acetate/heptane gradient, followed by 15% to afford the title compound (1.710 g) as an amber oil in about 90% purity. MS (ESI) [m/e, (M+H)$^+$]=185.3. $^1$H NMR (400 MHz, chloroform-d) δ ppm 10.22 (s, 1H), 4.28 (q, J=7.24 Hz, 2H), 4.12-4.19 (m, 2H), 2.54 (t, J=6.57 Hz, 2H), 1.88-1.98 (m, 2H), 1.30-1.38 (m, 3H).

Intermediate 40

3,4-Dihydro-2H-pyrano[2,3-d]pyridazin-5(6H)-one

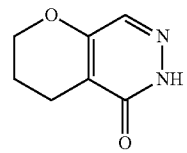 [SMILES: O=c1[nH]ncc2c1CCCO2]

To a stirred 0° C. mixture of ethyl 6-formyl-3,4-dihydro-2H-pyran-5-carboxylate (1.705 g, 9.26 mmol) in methanol (80 mL) was added very quickly 35% hydrazine hydrate (0.311 g, 9.72 mmol). After 20 minutes, the solvent was removed under reduced pressure, and the residue was treated with acetic acid (70 mL) and water (7 mL) and stirred at 110° C. for 20 minutes. The solvents were removed in vacuo. The crude residue was eluted by silica gel chromatography with a 0 to 25% gradient of methanol/dichloromethane to afford the title compound (1.384 g) as a light yellow solid in better than 90% purity. MS (ESI) [m/e, (M+H)$^+$]=153.2. $^1$H NMR (400 MHz, chloroform-d) δ ppm 10.56 (br s, 1H), 7.53 (s, 1H), 4.17-4.35 (m, 2H), 2.57 (t, J=6.57 Hz, 2H), 1.99-2.08 (m, 2H).

Intermediate 41

5-Chloro-3,4-dihydro-2H-pyrano[2,3-d]pyridazine

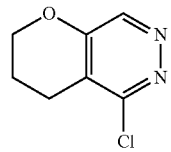 [SMILES: Clc1nncc2c1CCCO2]

3,4-Dihydro-2H-pyrano[2,3-d]pyridazin-5(6H)-one (400 mg, 2.63 mmol) was stirred in phosphorus oxychloride (4 mL, 6.58 g, 42.9 mmol) at 95° C. for nearly 2 hours. The reaction was then cooled to room temperature and excess phosphorus oxychloride was removed in vacuo. The residue was treated with ice (~15 g) and very slowly with solid potassium carbonate until pH >7. A tan solid was isolated by filtration and dried under vacuum to afford the title compound (267 mg, 57% yield). MS (ESI) [m/e, (M)$^+$]=170.6. 1H NMR (400 MHz, chloroform-d) δ ppm 8.68 (s, 1H), 4.28-4.42 (m, 2H), 2.78 (t, J=6.32 Hz, 2H), 2.05-2.20 (m, 2H).

Intermediate 42

N-(2,4-dimethoxybenzyl)-3,4-dihydro-2H-pyrano[2,3-d]pyridazin-5-amine

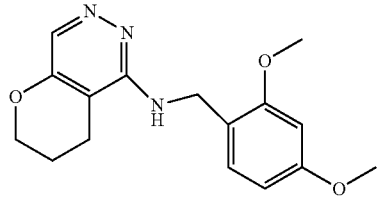 [SMILES: COc1ccc(CNc2nncc3c2CCCO3)c(OC)c1]

A mixture of 5-chloro-3,4-dihydro-2H-pyrano[2,3-d]pyridazine (150 mg, 0.879 mmol), N,N-diisopropylethylamine (0.154 mL, 114 mg, 0.879 mmol), and 2,4-dimethoxybenzylamine (294 mg, 1.76 mmol) in isopropanol (2 mL) was heated in a sealed tube 18 hours at 115° C. and then 4.5 hours at 145° C. before addition of excess 2,4-dimethoxybenzylamine (about 2 g, 12 mmol). The reaction was stirred at 145° C. for 18 hours. After cooling to room temperature, isopropanol was removed in vacuo. The crude was then treated with diethyl ether (30 mL). A tan solid was removed by filtration. The filtrate was washed twice with small amounts of saturated aqueous ammonium chloride. The organic layer was dried over sodium sulfate, filtered, and concentrated down. The crude was purified by silica gel chromatography with a 0 to 10% methanol/dichloromethane gradient to afford the title compound (159 mg) as an amber foamy oil. MS (ESI) [m/e, (M)$^+$]=301.8. $^1$H NMR (400 MHz, chloroform-d) δ ppm 8.22 (s, 1H), 7.35 (d, J=8.08 Hz, 1H), 6.36-6.56 (m, 2H), 4.73 (d, J=5.56 Hz, 2H), 4.37-4.56 (m, 1H), 4.11-4.24 (m, 2H), 3.86 (s, 3H), 3.81 (s, 3H), 2.27-2.31 (m, 2H), 2.04-2.11 (m, 2H).

Intermediate 43

3,4-Dihydro-2H-pyrano[2,3-d]pyridazin-5-amine hydrobromide

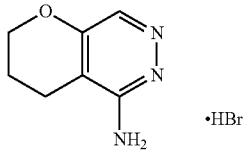 [SMILES: Nc1nncc2c1CCCO2 ; Br]

A mixture of N-(2,4-dimethoxybenzyl)-3,4-dihydro-2H-pyrano[2,3-d]pyridazin-5-amine (158, 0.524 mmol) and 30% by weight hydrobromic acid/acetic acid (0.3 mL, 0.4 g, 1.5 mmol) in acetic acid (3 mL) was stirred nearly 2 hours at 90° C. The reaction was then cooled to room temperature and the solvents were removed in vacuo. The dark red solid was washed with diethyl ether and then dried to afford the crude title compound (122 mg) in about 65% purity. MS (ESI) [m/e, (M)$^+$]=151.7. $^1$H NMR (400 MHz, DMSO-d$_6$) δ ppm 8.22 (s, 1H), 8.11 (br s, 2H), 4.36-4.40 (m, 2H), 2.47 (t, J=6.32 Hz, 2H), 1.98-2.06 (m, 2H).

Example 1

2-Chloro-6-{3-[4-(4-methoxy-benzoyl)-piperidin-1-yl]-2-oxo-pyrrolidin-1-ylmethyl}-benzonitrile

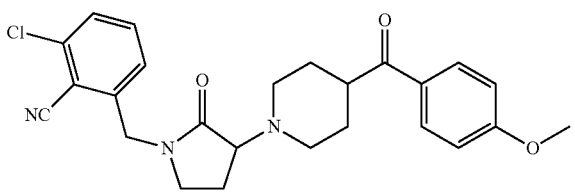 [SMILES: COc1ccc(C(=O)C2CCN(C3CCN(Cc4cccc(Cl)c4C#N)C3=O)CC2)cc1]

To a solution of 3-(4-(4-methoxybenzoyl)piperidin-1-yl) pyrrolidin-2-one (70 mg, 0.23 mmol) and 2-(bromomethyl)-6-chlorobenzonitrile (80 mg, 0.35 mmol) in tetrahydrofuran (1 mL) and dimethylformamide (0.1 mL) was added sodium hydride (46 mg, 1.2 mmol, 60% in mineral oil). The mixture was stirred at ambient temperature for 30 minutes. Dichloromethane and methanol were added slowly to quench the reaction. Then the mixture was filtered through a short pad of silical gel column, the solvent was removed in vacuo, and the residue was purified via flash column chromatography (ethyl acetate:hexane, 10:90 to 100:0) first and then (methanol: dichloromethane, 1:99 to 10:90) to give brown oil which is further purified by HPLC to give a colorless product. $^1$H NMR (400 MHz, CDCl$_3$) δ 7.85 (m, 2H), 7.45 (t, J=8.0 Hz, 1H), 7.35-7.41 (m, 1H), 7.30 (d, J=7.5 Hz, 1H), 6.87 (m, J=9.0 Hz, 2H), 4.62 (q, J=15.6 Hz, 2H), 3.80 (s, 3H), 3.50 (t, J=9.0 Hz, 1H), 3.11-3.37 (m, 3H), 2.94-3.11 (m, 1H), 2.75-2.94 (m, 2H), 2.28-2.54 (m, 1H), 2.09-2.28 (m, 1H), 1.90-2.09 (m, 1H), 1.66-1.90 (m, 4H). HRMS calculated for C$_{25}$H$_{26}$ClN$_3$O$_3$ 452.1741. found (ESI, [M+H]$^+$), 452.1760.

Example 2

2-{3-[4-(4-Methoxy-benzoyl)-piperidin-1-yl]-2-oxo-pyrrolidin-1-ylmethyl}-3,5,7,8-tetrahydro-pyrano[4,3-d]pyrimidin-4-one

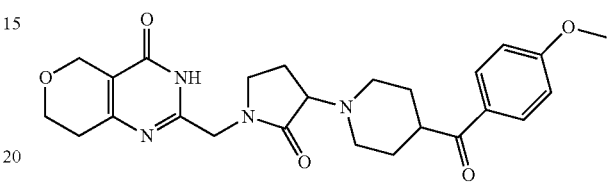

To a solution of 3-[4-(4-methoxy-benzoyl)-piperidin-1-yl]-pyrrolidin-2-one (43.7 mmol, 13.2 g) and 2-chloromethyl-3,5,7,8-tetrahydro-pyrano[4,3-d]pyrimidin-4-one (48 mmol, 9.6 g) in THF (400 mL) and DMF formula (20 mL) was added sodium hydride (60%, 153 mmol, 6.1 g) and heated to 70° C. for 1 hour. The reaction was allowed to cool to ambient temperature, diluted with 1 L of ether, and the resulting solid in suspension was filtered and dried under vacuum provided the title compound as an off-white solid (22 g, 95.3% yield). HRMS calculated for C$_{25}$H$_{30}$N$_4$O$_5$ 466.5417. found (ESI, [M+H]$^+$) 467.2305. $^1$H NMR (400 MHz, MeOD) δ ppm 1.67-1.92 (m, 4H) 2.05-2.24 (m, 2H) 2.47-2.64 (m, 3H) 2.72-2.82 (m, 1H) 2.84-2.93 (m, 1H) 3.06-3.15 (m, 1H) 3.26-3.47 (m, 10H) 3.68 (t, J=8.78 Hz, 1H) 3.83-3.99 (m, 5H) 4.16 (d, J=15.56 Hz, 1H) 4.40-4.58 (m, 3H) 7.01 (d, J=9.03 Hz, 2H) 7.97 (d, J=9.03 Hz, 2H), analytical RP-HPLC (Novapak 150×3.9 mm C18 column: mobile phase: 10-90% acetonitrile/water with 0.1% TFA, at 2 mL/min over 5 min.) retention time=2.455 min.

Example 3

2-{(S)-3-[4-(4-Methoxy-benzoyl)-piperidin-1-yl]-2-oxo-pyrrolidin-1-ylmethyl}-3,5,7,8-tetrahydro-pyrano[4,3-d]pyrimidin-4-one

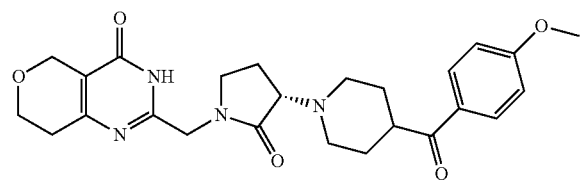 [SMILES: COc1ccc(C(=O)C2CCN([C@H]3CCN(Cc4nc5c(c(=O)[nH]4)COCC5)C3=O)CC2)cc1]

2-{3-[4-(4-Methoxy-benzoyl)-piperidin-1-yl]-2-oxo-pyrrolidin-1-ylmethyl}-3,5,7,8-tetrahydro-pyrano[4,3-d]pyrimidin-4-one (21 g) was dissolved in methanol (2.1 L) and sonicated for 30 min and the undissolved material was removed by filtration. Chiral separation via SFC chromatography on a 3.0×25.0 cm (S,S) Whelk 0-1 column eluting 50% MeOH/1% isopropylamine/CO$_2$ (v/v) at 70 mL/min at 125 bar afforded 7.91 g of material. The material was codistilled with chloroform (10×1 L) under vacuum until dry. The dried sample was dissolved in acetonitrile/water and frozen by immersing in liquid $N_2$ and put under vacuum (0.014 torr) for 3 days. The lyophilized material was dissolved in acetonitrile and treated with $K_2CO_3$ (6.3 g) and heated to 80° C. for 45 min., filtered and dried (9.1 g). The salt (8 g) was dissolved in 40 mL of water and chilled to 0° C., aqueous HCl (5 mL of a 15% solution chilled to 0° C.) was added dropwise until pH 9.5 whereupon the solution became cloudy. The solution was extracted with dichloromethane (2×50 mL) and concentrated to dryness. The compound was further dried in a tube under vacuum at 65° C. resulted in the free base of (4.246 g, 40.4% yield). HRMS calculated for $C_{25}H_{30}N_4O_5$ 466.5417. found (ESI, [M+H]$^+$) 467.2305. $^1$H NMR (400 MHz, MeOD) 8 ppm 1.67-1.91 (m, 4H) 2.08-2.31 (m, 2H) 2.48-2.58 (m, 1H) 2.59-2.66 (m, 2H) 2.78-2.87 (m, 1H) 2.89-2.98 (m, 1H) 3.11-3.19 (m, 1H) 3.27-3.41 (m, 12H) 3.45-3.52 (m, 2H) 3.64 (t, J=8.53 Hz, 1H) 3.87 (s, 3H) 3.91 (t, J=5.52 Hz, 2H) 4.38 (d, J=10.54 Hz, 2H) 4.48 (s, 2H) 7.01 (d, J=9.03 Hz, 2H) 7.96 (d, J=9.03 Hz, 2H). HPLC (Novapak 150×3.9 mm C18 column: mobile phase: 10-90% acetonitrile/water with 0.1% TFA, at 2 mL/min over 5 min.) retention time=2.455 min Alternative Procedure A solution of (S)-3-(4-(4-methoxybenzoyl)piperidin-1-yl)pyrrolidin-2-one (25.66 g, 85 mmol) in THF (283 mL) was cooled to −1.7° C. and to this was slowly added NaH (10.18 g, 255 mmol) and 2-chloromethyl-3,5,7,8-tetrahydro-pyrano[4,3-d]pyrimidin-4-one (89 mmol, 17.88 g) maintaining the temperature below 5° C. The reaction vessel was immersed into an ice-water bath and allowed bath to expire overnight. When reaction was complete by LCMS (approximately 15 h), the reaction was cooled to 1.7° C. and saturated $NH_4Cl$ was slowly added, keeping the internal temperature below 10° C. The mixture was diluted with dichloromethane (500 mL) and 1 N NaOH (500 mL) and split into two batches that were processed identically. Additional 1 N NaOH (500 mL) was added and the aqueous layer was washed with dichloromethane (2×500 mL). The aqueous layer was adjusted to pH 7 using approximately 250 mL 3 N HCl and extracted with dichloromethane (4×500 mL), dried over $Na_2SO_4$, filtered and concentrated in vacuo. The crude material was taken up in dichloromethane (500 mL) and ethyl acetate (500 mL) was added. The resulting solution was concentrated to an approximate volume of 300 mL and seeded with pure title compound and concentrated further in vacuo. To this stirred solution was added ethyl acetate (500 mL) and a seed of pure title compound. Filtration of the suspension provided the title compound as a white solid (32.87 g, 70.5 mmol).

Example 4

2-{(R)-3-[4-(4-Methoxy-benzoyl)-piperidin-1-yl]-2-oxo-pyrrolidin-1-ylmethyl}-3,5,7,8-tetrahydro-pyrano[4,3-d]pyrimidin-4-one

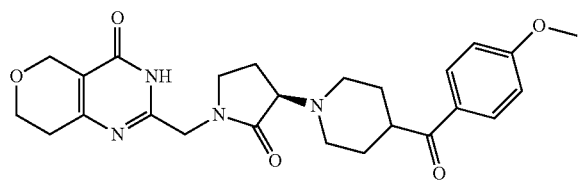 [SMILES: COc1ccc(C(=O)C2CCN([C@@H]3CCN(Cc4nc5c(c(=O)[nH]4)COCC5)C3=O)CC2)cc1]

2-{3-[4-(4-Methoxy-benzoyl)-piperidin-1-yl]-2-oxo-pyrrolidin-1-ylmethyl}-3,5,7,8-tetrahydro-pyrano[4,3-d]pyrimidin-4-one (37 mg) was purified via chiral SFC chromatography on an AS-H column (60 g/min, 21×250 mm) eluting 40% IPA/0.2% DEA/$CO_2$ (v/v) affording 19 mg of crude material which was further purified by HPLC (300×50 mm) eluting with a gradient of 25-35% acetonitrile/water over 45 min., followed by lyophilization of the pure fractions provided the TFA salt of the desired material. Neutralization of the TFA salt by filtration through a bicarbonate MP resin cartridge eluting with methanol (2 mL), DCM (3 mL), and methanol (2 mL) afforded the title compound (5 mg, 26% yield). MW calculated for $C_{25}H_{30}N_4O_5$ 466.5417, HRMS m/z found 467.2305 (M+H)$^+$; $^1$H NMR (400 MHz, MeOD) δ ppm 1.69-1.90 (m, 4H) 2.09-2.32 (m, 2H) 2.48-2.58 (m, 1H) 2.59-2.66 (m, 2H) 2.77-2.87 (m, 1H) 2.90-2.99 (m, 1H) 3.11-3.20 (m, 1H) 3.26-3.42 (m, 12H) 3.50 (s, 2H) 3.63 (s, 1H) 3.87 (s, 3H) 3.91 (t, J=5.77 Hz, 2H) 4.39 (s, 2H) 4.47 (s, 2H) 7.01 (d, J=9.03 Hz, 2H) 7.96 (d, J=9.03 Hz, 2H; HPLC (Novapak 150×3.9 mm C18 column: mobile phase: 10-90% acetonitrile/water with 0.1% TFA, at 2 mL/min over 5 min.) retention time=2.455 min Alternative Procedure To a solution of (R)-3-[4-(4-methoxy-benzoyl)-piperidin-1-yl]-pyrrolidin-2-one (0.165 mmol, 50 mg), which was prepared in a similar manner as (R)-3-[4-(4-methoxy-benzoyl)-piperidin-1-yl]-pyrrolidin-2-one from (S)-3-hydroxypyrrolidin-2-one and 2-chloromethyl-3,5,7,8-tetrahydro-pyrano[4,3-d]pyrimidin-4-one (0.165 mmol, 33.2 mg) in THF (5 mL) was added 1 M solution of potassium hexamethyldisilylamide in THF (0.331 mmol, 0.331 mL) at −78° C. for 2 hours. The reaction was allowed to warm to 0° C. for 16 hours and evaporated under vacuum. The remaining residue was purified by flash column chromatography (silica) eluting over a gradient of 0-50% MeOH/ethyl acetate provided the title compound as an off-white solid (20 mg, 25.9% yield). HRMS calculated for $C_{25}H_{30}N_4O_5$ 466.5417. found (ESI, [M+H]') 467.2296. $^1$H NMR (400 MHz, MeOD) 8 ppm 1.69-1.91 (m, 4H) 2.10-2.33 (m, 2H) 2.49-2.59 (m, 1H) 2.59-2.67 (m, 2H) 2.76-2.89 (m, 1H) 2.91-3.01 (m, 1H) 3.11-3.22 (m, 1H) 3.32-3.44 (m, 2H) 3.46-3.58 (m, 2H) 3.59-3.71 (t, J=8.78 Hz, 1H) 3.88-3.96 (m, 2H) 4.04-4.14 (d, J=15.56 Hz, 2H) 4.36-4.42 (m, 2H) 4.44-4.51 (m, 2H) 6.97 (d, J=9.03 Hz, 2H) 7.92 (d, J=9.03 Hz, 2H), analytical RP-HPLC retention time=4.02 min.

Example 5

2-Chloro-5-((3-(4-(4-methoxybenzoyl)piperidin-1-yl)-2-oxopyrrolidin-1-yl)methyl)benzonitrile

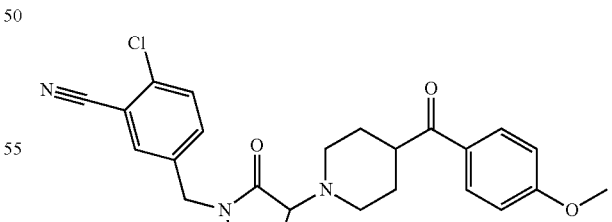

To a mixture of 3-(4-(4-methoxybenzoyl)piperidin-1-yl)pyrrolidin-2-one (70 mg, 0.232 mmol) and 5-(bromomethyl)-2-chlorobenzonitrile (80 mg, 0.347 mmol) in THF (1 mL) and DMF (0.1 mL) was added NaH (46.3 mg, 1.16 mmol, 60%). The reaction was concentrated in vacuo then taken up in dichlormethane and MeOH and filtered through a short plug of silica gel. The pooled fractions containing the title material were pooled, concentrated and neutralized with NaHCO₃. MeOH was added and the solution was cooled in a freezer. The title compound was obtained by collecting the white solid via filtration (45 mg). HRMS calculated for C$_{25}$H$_{26}$ClN$_3$O$_3$ 451.1671. found (ESI, [M+H]$^+$) 452.1744.

Example 6

6-{3-[4-(4-Methoxy-benzoyl)-piperidin-1-yl]-2-oxo-pyrrolidin-1-ylmethyl}-1-methyl-1,3a,5,7a-tetrahydro-pyrazolo[3,4-d]pyrimidin-4-one

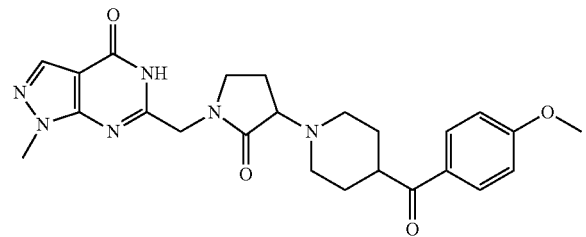 [SMILES: COc1ccc(C(=O)C2CCN(C3CCN(Cc4nc5c(cnn5C)c(=O)[nH]4)C3=O)CC2)cc1]

To a solution of 3-[4-(4-methoxy-benzoyl)-piperidin-1-yl]-pyrrolidin-2-one (0.165 mmol, 50 mg) and 6-chloromethyl-1-methyl-1,5-dihydro-pyrazolo[3,4-d]pyrimidin-4-one (0.165 mmol, 33 mg) in THF (2 mL) was added sodium hydride (60%, 0.331 mmol, 23 mg) and heated to 70° C. for 1 hour. The reaction was allowed to cool to ambient temperature, diluted with 10 mL of ether, and the resulting solid in suspension was filtered and dried under vacuum provided the title compound as an off-white solid (66.4 mg, 87% yield). HRMS calculated for C$_{24}$H$_{28}$N$_6$O$_4$ 464.5286. found (ESI, [M+H]$^+$) 465.2256. $^1$H NMR (400 MHz, MeOD) δ ppm 1.70-1.93 (m, 4H) 2.09-2.31 (m, 2H) 2.53-2.66 (m, 1H) 2.80-2.91 (m, 1H) 2.93-3.02 (m, 1H) 3.10-3.21 (m, 1H) 3.33-3.43 (m, 2H) 3.48-3.57 (m, 2H) 3.65-3.75 (m, 1H) 3.83-3.90 (m, 6H) 4.37-4.51 (m, 2H) 6.97 (d, J=9.03 Hz, 2H) 7.83-7.91 (m, 1H) 7.97 (d, J=9.03 Hz, 2H), analytical RP-HPLC retention time=2.77 min Example 7

2-{3-[4-(4-Methoxy-benzoyl)-piperidin-1-yl]-2-oxo-pyrrolidin-1-ylmethyl}-4a,7a-dihydro-3H-thieno[3,2-d]pyrimidin-4-one

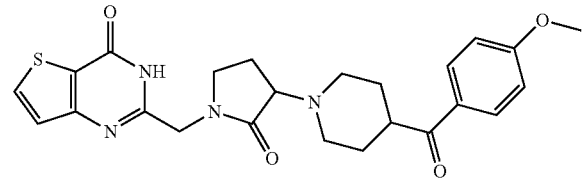 [SMILES: COc1ccc(C(=O)C2CCN(C3CCN(Cc4nc5ccsc5c(=O)[nH]4)C3=O)CC2)cc1]

To a solution of 3-[4-(4-methoxy-benzoyl)-piperidin-1-yl]-pyrrolidin-2-one (0.165 mmol, 50 mg) and 2-chloromethyl-3H-thieno[3,2-d]pyrimidin-4-one (0.165 mmol, 33 mg) in THF (2 mL) was added sodium hydride (60%, 0.331 mmol, 23 mg) and heated to 70° C. for 1 hour. The reaction was allowed to cool to ambient temperature, diluted with 10 mL of ether, and the resulting solid in suspension was filtered and dried under vacuum provided the title compound as an off-white solid (70.5 mg, 95.4% yield). HRMS calculated for C$_{24}$H$_{26}$N$_4$O$_4$S 466.5632. found (ESI, [M+H]$^+$) 467.1740. $^1$H NMR (400 MHz, MeOD) δ ppm 1.65-1.92 (m, 4H) 2.06-2.29 (m, 2H) 2.48-2.62 (m, 1H) 2.78-2.89 (m, 1H) 2.89-3.00 (m, 1H) 3.09-3.18 (m, 1H) 3.34-3.53 (m, 4H) 3.55-3.65 (m, 1H) 3.68-3.77 (m, 1H) 4.23-4.32 (m, 1H) 4.60-4.69 (m, 1H) 6.97 (d, J=9.03 Hz, 2H) 7.17-7.24 (m, 1H) 7.73-7.81 (m, 1H) 7.96 (d, J=9.03 Hz, 2H), analytical RP-HPLC retention time=2.77 min Example 8

2-{3-[4-(4-Methoxy-benzoyl)-piperidin-1-yl]-2-oxo-pyrrolidin-1-ylmethyl}-6-methyl-4a,7a-dihydro-3H-thieno[2,3-d]pyrimidin-4-one

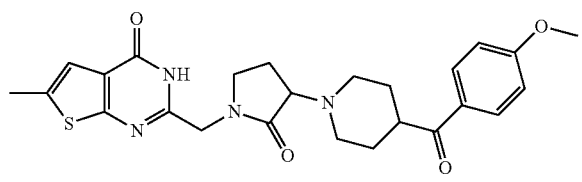

To a solution of 3-[4-(4-methoxy-benzoyl)-piperidin-1-yl]-pyrrolidin-2-one (0.165 mmol, 50 mg) and 2-chloromethyl-6-methyl-3H-thieno[2,3-d]pyrimidin-4-one (0.165 mmol, 33 mg) in THF (2 mL) was added sodium hydride (60%, 0.331 mmol, 23 mg) and heated to 70° C. for 1 hour. The reaction was allowed to cool to ambient temperature, diluted with 10 mL of ether, and the resulting solid in suspension was filtered and dried under vacuum provided the title compound as an off-white solid (70.5 mg, 95.4% yield). HRMS calculated for C$_{25}$H$_{28}$N$_4$O$_4$S 480.5903. found (ESI, [M+H]$^+$) 481.1907. $^1$H NMR (400 MHz, MeOD) δ ppm 1.66-1.93 (m, 4H) 2.05-2.30 (m, 2H) 2.51-2.63 (m, 1H) 2.79-2.90 (m, 1H) 2.90-2.98 (m, 1H) 3.03-3.18 (m, 1H) 3.33-3.54 (m, 4H) 3.65-3.75 (m, 1H) 3.87 (s, 3H) 4.20-4.31 (m, 1H) 4.51-4.62 (m, 1H) 6.94-7.06 (m, 3H) 7.98 (d, J=9.03 Hz, 2H), analytical RP-HPLC retention time=3.22 min Example 9

2-{3-[4-(4-Chloro-benzoyl)-piperidin-1-yl]-2-oxo-pyrrolidin-1-ylmethyl}-3,5,7,8-tetrahydro-pyrano[4,3-d]pyrimidin-4-one

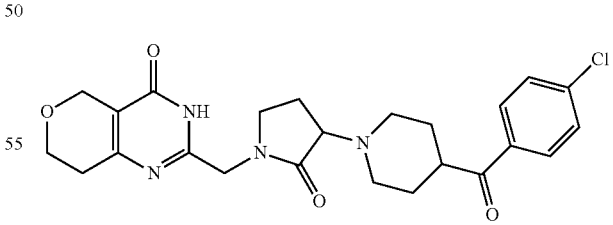

To a solution of 3-[4-(4-chloro-benzoyl)-piperidin-1-yl]-pyrrolidin-2-one (0.17 mmol, 53 mg) and 2-chloromethyl-3,5,7,8-tetrahydro-pyrano[4,3-d]pyrimidin-4-one (0.17 mmol, 35 mg) in THF (15 mL and DMF (2.5 mL) was added sodium hydride (60%, (0.6 mmol, 14 mg) and heated to 70° C. for 15 min. The reaction was concentrated in vacuo and the remainder of the DMF was removed via a stream of N$_2$. The crude material was purified by preparative reverse-phase HPLC (300×50 mm) eluting with a gradient of 25-35% acetonitrile/water over 45 min. Lyophilization of the pure fractions provided the TFA salt of the desired material. Neutralization of the TFA salt by filtration through a bicarbonate MP resin cartridge eluting with methanol (2 mL), DCM (3 mL), and methanol (2 mL) afforded the title compound (7 mg, 8.6% yield). HR-MS m/z (M+H)$^+$: measured 471.1823 calculated for $C_{24}H_{27}ClN_4O_4$=466.5417; $^1$H NMR (400 MHz, MeOD) δ ppm 1.66-1.92 (m, 6H) 2.05-2.28 (m, 3H) 2.47-2.67 (m, 5H) 2.75-2.87 (m, 2H) 2.88-2.97 (m, 2H) 3.08-3.18 (m, 2H) 3.24-3.51 (m, 22H) 3.61-3.70 (m, 2H) 3.91 (t, J=5.52 Hz, 2H) 4.20-4.32 (m, 1H) 4.38-4.54 (m, 3H) 7.51 (d, J=8.53 Hz, 2H) 7.96 (d, J=8.53 Hz, 2H). HPLC (Novapak 150×3.9 mm C18 column: mobile phase: 10-90% acetonitrile/water with 0.1% TFA, at 2 mL/min over 5 min.) retention time=2.666 min.

Example 10

2-{3-[4-(4-Fluoro-benzoyl)-piperidin-1-yl]-2-oxo-pyrrolidin-1-ylmethyl}-3,5,7,8-tetrahydro-pyrano[4,3-d]pyrimidin-4-one

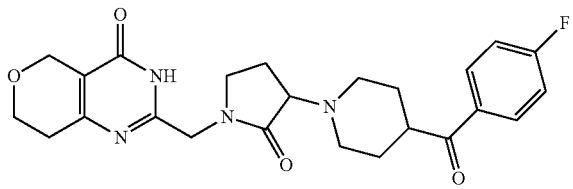 [SMILES: O=C(c1ccc(F)cc1)C1CCN(C2CCN(Cc3nc4c(c(=O)[nH]3)COCC4)C2=O)CC1]

To a solution of 3-[4-(4-fluoro-benzoyl)-piperidin-1-yl]-pyrrolidin-2-one (0.39 mmol, 112 mg) and 2-chloromethyl-3,5,7,8-tetrahydro-pyrano[4,3-d]pyrimidin-4-one (0.39 mmol, 76 mg) in THF (15 mL and DMF (2.5 mL) was added sodium hydride (60%, (1.35 mmol, 54 mg) and heated to 70° C. for 15 min. The reaction was concentrated in vacuo and the remainder of the DMF was removed via a stream of N$_2$. The crude material was purified by preparative reverse-phase HPLC (300×50 mm) eluting with a gradient of 25-35% acetonitrile/water over 45 min., followed by lyophilization of the pure fractions provided the TFA salt of the desired material. Neutralization of the TFA salt by filtration through a bicarbonate MP resin cartridge eluting with methanol (2 mL), DCM (3 mL), and methanol (2 mL) afforded the title compound (100 mg, 57% yield). HR-MS m/z (M+H)$^+$: measured 455.2111, calculated for molecular formula $C_{24}H_{27}FN_4O_4$=454.5056; $^1$H NMR (400 MHz, MeOD) δ ppm 1.58-1.85 (m, 4H) 1.99-2.24 (m, 2H) 2.42-2.57 (m, 3H) 2.67-2.81 (m, 1H) 2.84-2.93 (m, 1H) 3.11-3.17 (m, 1H) 3.36-3.47 (m, 2H) 3.52-3.62 (m, 1H) 3.76-3.86 (m, 2H) 4.26-4.40 (m, 4H) 7.09-7.18 (m, 2H) 7.91-8.00 (m, 2H); HPLC (Novapak 150×3.9 mm C18 column: mobile phase: 10-90% acetonitrile/water with 0.1% TFA, at 2 mL/min over 5 min.) retention time=2.461 min.

Example 11

2-{(S)-3-[4-(4-Fluoro-benzoyl)-piperidin-1-yl]-2-oxo-pyrrolidin-1-ylmethyl}-3,5,7,8-tetrahydro-pyrano[4,3-d]pyrimidin-4-one

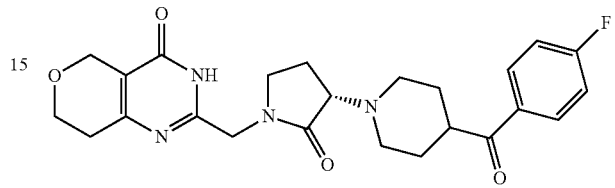

Chiral resolution 2-{3-[4-(4-fluoro-benzoyl)-piperidin-1-yl]-2-oxo-pyrrolidin-1-ylmethyl}-3,5,7,8-tetrahydro-pyrano[4,3-d]pyrimidin-4-one (90 mg) via chiral SFC chromatography on a AS-H column (60 g/min, 21×250 mm) eluting 40% IPA/0.2% DEA/CO$_2$ (v/v) afforded 48 mg of crude material which was further purified by RP-HPLC (300×50 mm) eluting with a gradient of 25-35% acetonitrile/water over 45 min., followed by lyophilization of the pure fractions provided the TFA salt of the desired material. Neutralization of the TFA salt by filtration through a bicarbonate MP resin cartridge eluting with methanol (2 mL), DCM (3 mL), and methanol (2 mL) afforded the title compound (5 mg, 10.4% yield). HRMS m/z (M+H)$^+$: measured 455.2101 calculated for molecular formula $C_{24}H_{27}FN_4O_4$=454.5056; $^1$H NMR (400 MHz, MeOD) δ ppm 1.87-2.10 (m, 2H) 2.11-2.29 (m, 3H) 2.34-2.53 (m, 1H) 2.53-2.70 (m, 3H) 3.23-3.43 (m, 14H) 3.43-3.71 (m, 5H) 3.71-3.84 (m, 1H) 3.86-4.01 (m, 3H) 4.37-4.57 (m, 5H) 7.22-7.33 (m, 2H) 8.07-8.16 (m, 2H). HPLC (Novapak 150×3.9 mm C18 column: mobile phase: 10-90% acetonitrile/water with 0.1% TFA, at 2 mL/min over 5 min.) retention time=2.461 min Example 12

2-{(R)-3-[4-(4-Fluoro-benzoyl)-piperidin-1-yl]-2-oxo-pyrrolidin-1-ylmethyl}-3,5,7,8-tetrahydro-pyrano[4,3-d]pyrimidin-4-one

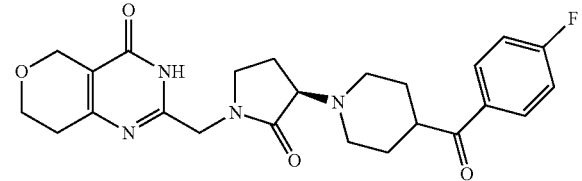 [SMILES: O=C(c1ccc(F)cc1)C1CCN([C@@H]2CCN(Cc3nc4c(c(=O)[nH]3)COCC4)C2=O)CC1]

Chiral resolution of 2-{3-[4-(4-fluoro-benzoyl)-piperidin-1-yl]-2-oxo-pyrrolidin-1-ylmethyl}-3,5,7,8-tetrahydro-pyrano[4,3-d]pyrimidin-4-one (90 mg) via SFC chromatography on a AS-H column (60 g/min, 21×250 mm) eluting 40% IPA/0.2% DEA/CO$_2$ (v/v) afforded 48 mg of crude material which was further purified by RP-HPLC (300×50 mm) eluting with a gradient of 25-35% acetonitrile/water over 45 min., followed by lyophilization of the pure fractions provided the TFA salt of the desired material. Neutralization of the TFA salt by filtration through a bicarbonate MP resin cartridge eluting with methanol (2 mL), DCM (3 mL), and methanol (2 mL) resulted in the free base of the title compound (27 mg, 56% yield). HRMS m/z (M+H)$^+$: measured 455.2088, calculated for molecular formula $C_{24}H_{27}FN_4O_4$=454.505; $^1$H NMR (400 MHz, MeOD) δ ppm 1.66-1.93 (m, 4H) 2.07-2.32 (m, 2H) 2.47-2.58 (m, 1H) 2.58-2.66 (m, 2H) 2.75-2.87 (m, 1H) 2.89-2.99 (m, 1H) 3.10-3.21 (m, 1H) 3.22-3.43 (m, 13H) 3.44-3.53 (m, 2H) 3.60-3.70 (m, 1H) 3.91 (t, J=5.52 Hz, 2H) 4.29-4.53 (m, 4H) 7.17-7.30 (m, 2H) 8.00-8.12 (m, 2H). HPLC (Novapak 150×3.9 mm C18 column: mobile phase: 10-90% acetonitrile/water with 0.1% TFA, at 2 mL/min over 5 min.) retention time=2.461 min

Example 13

2-{(S)-3-[4-(4-Methoxy-3-methyl-benzoyl)-piperidin-1-yl]-2-oxo-pyrrolidin-1-ylmethyl}-3,5,7,8-tetrahydro-pyrano[4,3-d]pyrimidin-4-one

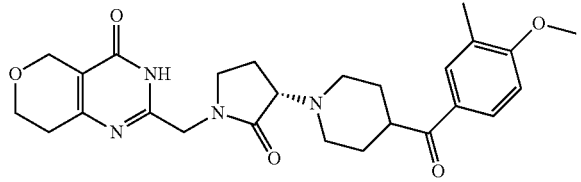 [SMILES: COc1ccc(C(=O)C2CCN([C@H]3CCN(Cc4nc5c(c(=O)[nH]4)COCC5)C3=O)CC2)cc1C]

To a solution of (R)-3-[4-(4-methoxy-3-methyl-benzoyl)-piperidin-1-yl]-pyrrolidin-2-one (0.79 mmol, 250 mg) and 2-chloromethyl-3,5,7,8-tetrahydro-pyrano[4,3-d]pyrimidin-4-one (0.87 mmol, 174 mg) in THF (10 mL) was added sodium hydride (60%, 2.77 mmol, 111 mg) and heated to 70° C. for 1 hour. The reaction was allowed to cool to ambient temperature, diluted with 100 mL of ether, and the resulting solid in suspension was filtered and dried under vacuum provided the title compound as an off-white solid (300 mg). Chiral resolution of 2-3-[4-(4-methoxy-3-methyl-benzoyl)-piperidin-1-yl]-2-oxo-pyrrolidin-1-ylmethyl}-3,5,7,8-tetrahydro-pyrano[4,3-d]pyrimidin-4-one (300 mg) via chiral SFC chromatography on a AS-H column (60 g/min, 21×250 mm) eluting 40% IPA/0.2% DEA/CO$_2$ (v/v) afforded 77 mg of pure material. HRMS calculated for $C_{26}H_{32}N_4O_5$=480.5687. found (ESI, [M+H]$^+$) 481.2455. $^1$H NMR (400 MHz, MeOD) δ ppm 1.69-1.90 (m, 4H) 2.10-2.20 (m, 1H) 2.20-2.31 (m, 4H) 2.48-2.58 (m, 1H) 2.59-2.65 (m, 2H) 2.77-2.88 (m, 1H) 2.90-3.06 (m, 1H) 3.10-3.20 (m, 1H) 3.32-3.42 (m, 3H) 3.46-3.54 (m, 2H) 3.63 (t, J=8.53 Hz, 2H) 3.88-3.94 (m, 5H) 4.39 (s, 2H) 4.47 (s, 2H) 6.99 (d, J=8.53 Hz, 1H) 7.77 (s, 1H) 7.87 (dd, J=8.53, 2.01 Hz, 1H), analytical RP-HPLC (Novapak 150×3.9 mm C18 column: mobile phase: 10-90% acetonitrile/water with 0.1% TFA, at 2 mL/min over 5 min.) retention time=2.731 min.

Example 14

2-{(R)-3-[4-(4-Methoxy-3-methyl-benzoyl)-piperidin-1-yl]-2-oxo-pyrrolidin-1-ylmethyl}-3,5,7,8-tetrahydro-pyrano[4,3-d]pyrimidin-4-one

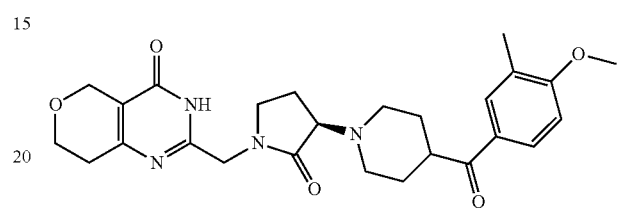

This material was obtained from 2-3-[4-(4-methoxy-3-methyl-benzoyl)-piperidin-1-yl]-2-oxo-pyrrolidin-1-ylmethyl}-3,5,7,8-tetrahydro-pyrano[4,3-d]pyrimidin-4-one (300 mg) via chiral SFC chromatography on a AS-H column (60 g/min, 21×250 mm) eluting 40% IPA/0.2% DEA/CO$_2$ (v/v) afforded 125 mg of pure material. HRMS calculated for $C_{26}H_{32}N_4O_5$ 480.5687. found (ESI, [M+H]$^+$) 481.2463. $^1$H NMR (400 MHz, MeOD) δ ppm 1.69-1.91 (m, 4H) 2.10-2.21 (m, 1H) 2.20-2.31 (m, 4H) 2.59-2.66 (m, 2H) 2.78-2.87 (m, 1H) 2.90-2.98 (m, 1H) 3.11-3.20 (m, 1H) 3.33-3.42 (m, 2H) 3.46-3.55 (m, 2H) 3.63 (t, J=8.78 Hz, 1H) 4.39 (s, 2H) 4.47 (s, 2H) 6.99 (d, J=8.53 Hz, 1H) 7.77 (s, 1H) 7.87 (dd, J=8.53, 2.01 Hz, 1H), analytical RP-HPLC (Novapak 150×3.9 mm C18 column: mobile phase: 10-90% acetonitrile/water with 0.1% TFA, at 2 mL/min over 5 min.) retention time=2.693 min.

Example 15

2-((3-(5-methoxy-1-oxo-1,3-dihydrospiro[indene-2,4'-piperidine]-1'-yl)-2-oxopyrrolidin-1-yl)methyl)-7,8-dihydro-3H-pyrano[4,3-d]pyrimidin-4(5H)-one

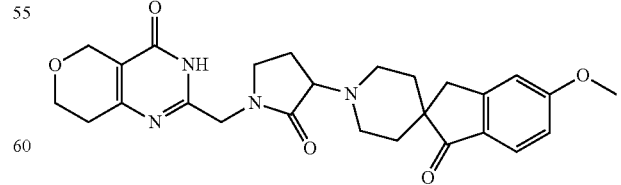

To a solution of 5-methoxy-1'-(2-oxopyrrolidin-3-yl)spiro[indene-2,4'-piperidin]-1(3H)-one (3.34 mmol, 1.05 g) and 2-chloromethyl-3,5,7,8-tetrahydro-pyrano[4,3-d]pyrimidin-4-one (3.67 mmol, 0.737 g) in THF (40 mL) and DMF (5 mL) was added sodium hydride (60%, 11.69 mmol, 0.468 g) and the suspension was heated at 70° C. for 45 min. The reaction was allowed to cool to ambient temperature, diluted with 100 mL of ether, an off-white solid was collected by filtration and was dried in vacuo. Recrystallization from isopropyl alcohol/methyl alcohol provided the title compound as an off-white solid (661 mg, 41.4% yield). Calculated MS=478.6, MS (ESI) m/e 479.0 (M+H$^+$); $^1$H NMR (400 MHz, MeOD) δ ppm 1.33-1.46 (m, 2H) 1.92-2.07 (m, 2H) 2.07-2.27 (m, 2H) 2.49-2.65 (m, 3H) 2.89 (dd, J=8.53, 2.51 Hz, 2H) 3.02-3.15 (m, 3H) 3.35-3.50 (m, 2H) 3.70 (t, J=8.78 Hz, 1H) 3.85-3.98 (m, 6H) 4.16 (d, J=15.06 Hz, 1H) 4.44-4.53 (m, 3H) 6.96 (dd, J=8.53, 2.51 Hz, 1H) 7.05 (s, 1H) 7.62 (d, J=9.03 Hz, 1H). HPLC (Novapak 150×3.9 mm C18 column: mobile phase: 10-90% acetonitrile/water with 0.1% TFA, at 2 mL/min over 5 min.) retention time=2.391 min.

Example 16

Peak 1 and

Example 17

Peak 2

Chiral resolution of 2-((3-(5-methoxy-1-oxo-1,3-dihydrospiro[indene-2,4'-piperidine]-1'-yl)-2-oxopyrrolidin-1-yl)methyl)-7,8-dihydro-3H-pyrano[4,3-d]pyrimidin-4(5H)-one (650 mg) via chiral SFC chromatography on a AS-H column (60 g/min, 21×250 mm) eluting 40% IPA/0.2% DEA/CO$_2$ (v/v) afforded two enantiomers (S)-2-((3-(5-methoxy-1-oxo-1,3-dihydrospiro[indene-2,4'-piperidine]-1'-yl)-2-oxopyrrolidin-1-yl)methyl)-7,8-dihydro-3H-pyrano[4,3-d]pyrimidin-4(5H)-one and (R)-2-((3-(5-methoxy-1-oxo-1,3-dihydrospiro[indene-2,4'-piperidine]-1'-yl)-2-oxopyrrolidin-1-yl)methyl)-7,8-dihydro-3H-pyrano[4,3-d]pyrimidin-4(5H)-one.

Peak 1: 145 mg, HRMS calculated for C$_{26}$H$_{30}$N$_4$O$_6$ 478.5528. found (ESI, [M+H]$^+$) 479.2291. $^1$H NMR (400 MHz, MeOD) δ ppm 1.39 (dd, J=11.29, 7.78 Hz, 3H) 1.91-2.05 (m, 2H) 2.06-2.26 (m, 2H) 2.50-2.65 (m, 3H) 3.02-3.14 (m, 3H) 3.23-3.32 (m, 3H) 3.34 (s, 1H) 3.40-3.47 (m, 2H) 3.68 (t, J=8.78 Hz, 1H) 3.87-3.94 (m, 4H) 4.18 (d, J=15.56 Hz, 1H) 4.44-4.52 (m, 3H) 6.96 (d, J=8.53 Hz, 1H) 7.04 (s, 1H) 7.61 (d, J=8.53 Hz, 1H). HPLC (Novapak 150×3.9 mm C18 column: mobile phase: 10-90% acetonitrile/water with 0.1% TFA, at 2 mL/min over 5 min.) retention time=2.430 min.

Peak 2: 177 mg, HRMS calculated for C$_{26}$H$_{30}$N$_4$O$_6$ 478.5528. found (ESI, [M+H]$^+$) 479.2294. $^1$H NMR (400 MHz, MeOD) δ ppm 1.36-1.52 (m, 10H) 1.91-2.06 (m, 3H) 2.08-2.30 (m, 3H) 2.50-2.65 (m, 6H) 2.76-2.95 (m, 6H) 3.03-3.14 (m, 5H) 3.25-3.36 (m, 16H) 3.38-3.51 (m, 4H) 3.58-3.74 (m, 3H) 3.86-3.94 (m, 8H) 4.20 (d, J=15.56 Hz, 2H) 4.44-4.54 (m, 5H) 6.92-6.97 (m, 1H) 7.05 (s, 2H) 7.62 (d, J=8.53 Hz, 2H). HPLC (Novapak 150×3.9 mm C18 column: mobile phase: 10-90% acetonitrile/water with 0.1% TFA, at 2 mL/min over 5 min.) retention time=2.432 min.

Example 18

2-[4-(4-Methoxy-benzoyl)-2'-oxo-[1,3']bipiperidinyl-1'-ylmethyl]-3,5,7,8-tetrahydro-pyrano[4,3-d]pyrimidin-4-one

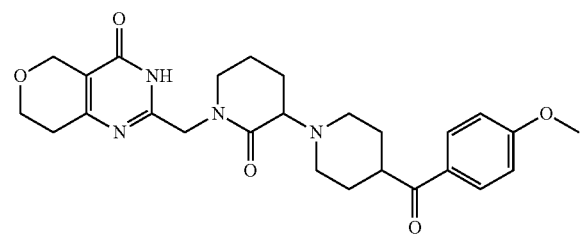 [SMILES: COc1ccc(C(=O)C2CCN(C3CCCN(Cc4nc5c(c(=O)[nH]4)COCC5)C3=O)CC2)cc1]

To a stirred solution of NaH (23.8 mg, 0.942 mmol, 2.1 eq) in THF (10 mL) were added 4-(4-methoxy-benzoyl)-[1,3']bipiperidinyl-2'-one (142 mg, 0.449 mmol, 1.0 eq) and 2-chloromethyl-3,5,7,8-tetrahydro-pyrano[4,3-d]pyrimidin-4-one (90 mg, 0.449 mmol, 1.0 eq). The reaction was let to stir at 70° C. for 3 h. The solid precipitate was filtered off and washed with CH$_2$Cl$_2$. The solvent of the mother liquor was evaporated and the residue purified by flash chromatography on silica gel (0-15% MeOH/CH$_2$Cl$_2$) to afford the title compound as an off-white powder (60 mg, 0.139 mmol, 31.1% yield). $^1$H NMR (400 MHz, DMSO-d$_6$) δ ppm 12.34 (br s, 1H) 7.94 (d, J=8.59 Hz, 2H) 7.03 (d, J=8.59 Hz, 2H) 4.14-4.54 (m, 5H) 4.06-4.10 (m, 1H) 3.45 (br s, 1H) 3.18 (d, J=5.05 Hz, 3H) 3.03 (br s, 1H) 2.85 (br s, 2H) 2.30-2.65 (m, 5H) 1.30-2.05 (m, 9H). HR-MS (m/z, MH+): 481.2461, 482.2471. HPLC retention time: 2.78 min (Agilent column 3.0×100 mm 3 um C18 column; flow rate of 1.0 mL/min with gradient from 5% to 95% acetonitrile in 10 min, 0.1% FA)

Example 19

Peak 1 and

Example 20

Peak 2

Chiral resolution of 2-[4-(4-methoxy-benzoyl)-2'-oxo-[1,3']bipiperidinyl-1'-ylmethyl]-3,5,7,8-tetrahydro-pyrano[4,3-d]pyrimidin-4-one using an OD-H column by SFC with mobile phase of 30% MeOH gave two enantiomers 2-[(S)-4-(4-Methoxy-benzoyl)-2'-oxo-[1,3']bipiperidinyl-1'-ylmethyl]-3,5,7,8-tetrahydro-pyrano[4,3-d]pyrimidin-4-one and 2-[(R)-4-(4-Methoxy-benzoyl)-2'-oxo-[1,3']bipiperidinyl-1'-ylmethyl]-3,5,7,8-tetrahydro-pyrano[4,3-d]pyrimidin-4-one.

Peak 1 retention time=2.31 min.

Peak 2 retention time=3.17 min.

Example 21

2-((3-(4-(4-methoxybenzoyl)piperidin-1-yl)-2-oxopyrrolidin-1-yl)methyl)-6,7-dihydro-3H-cyclopenta[d]pyrimidin-4(5H)-one

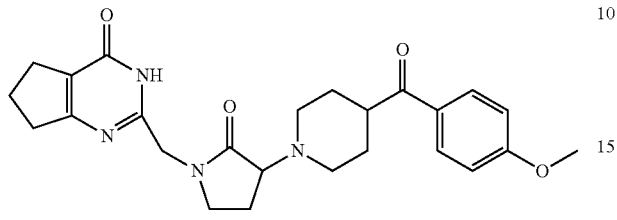

To a solution of 2-(3-(4-(4-methoxybenzoyl)piperidin-1-yl)-2-oxopyrrolidin-1-yl)acetimidamide hydrochloride (140 mg, 0.37 mmol) and methyl 2-oxocyclopentanecarboxylate (0.060 mL, 0.47 mmol) in ethanol (4 mL) was added sodium ethoxide (0.160 mL, 0.44 mmol, 21%). The mixture was heated at 100° C. for 24 h. The resulting mixture was purified via flash column chromatography (methanol: dichloromethane, 1:99 to 10:90) and then crystalized out from methanol to provide slightly yellow solid (33 mg, 20% yield). $^1$H NMR (400 MHz, CDCl$_3$) δ 10.85 (s, 1H), 7.95 (d, J=8.5 Hz, 2H), 6.96 (d, J=8.5 Hz, 2H), 4.32-4.47 (m, 2H), 3.89 (s, 3H), 3.60-3.73 (m, 1H), 3.40-3.56 (m, 2H), 3.23-3.37 (br. s, 1H), 3.00-3.20 (br. s, 3H), 2.84 (ddd, 4H, J=14.7, 7.5, 7.4 Hz), 2.46-2.62 (br. s, 1H), 2.38 (d, 1H, J=7.0 Hz), 2.15-2.25 (br. s, 1H), 2.10 (dq, 2H, J=7.8, 7.6 Hz), 1.82-2.01 (br. s, 4H) HRMS calculated for C$_{25}$H$_{30}$N$_4$O$_4$ 451.2345. found (ESI, [M+H]$^+$), 451.2362.

Example 22

2-{3-[4-(4-Methoxy-benzoyl)-piperidin-1-yl]-2-oxopyrrolidin-1-ylmethyl}-3H-pyrimidin-4-one

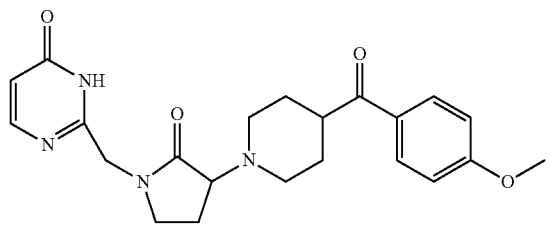 [SMILES: COc1ccc(C(=O)C2CCN(C3CCN(Cc4nccc(=O)[nH]4)C3=O)CC2)cc1]

The title compound (1.8 mg, 1% yield) was prepared using a similar method to the one described in Example 21 from (E)-methyl 3-methoxyacrylate (0.055 mL, 0.47 mmol). $^1$H NMR (400 MHz, CD$_3$OD) δ 8.03 (d, J=9.0 Hz, 2H), 7.92 (d, J=6.5 Hz, 1H), 7.05 (d, J=9.0 Hz, 2H), 6.33 (d, J=7.0 Hz, 1H), 4.48-4.58 (m, 2H), 4.36-4.48 (m, 1H), 3.93-4.05 (br. s. 1H), 3.89 (s, 3H), 3.70-3.83 (br. s, 1H), 3.66 (d, J=8.0 Hz, 2H), 3.51-3.63 (br. s, 2H), 3.25-3.39 (m, 1H), 2.54-2.71 (m, 1H), 2.47 (d, J=10.0 Hz, 1H), 2.19 (d, J=14.1 Hz, 2H), 2.03-2.15 (br. s, 2H). HRMS calculated for C$_{22}$H$_{26}$N$_4$O$_4$ 411.2032. found (ESI, [M+H]$^+$), 411.2047.

Example 23

2-{3-[4-(4-Methoxy-benzoyl)-piperidin-1-yl]-2-oxopyrrolidin-1-ylmethyl}-6-methyl-3H-pyrimidin-4-one

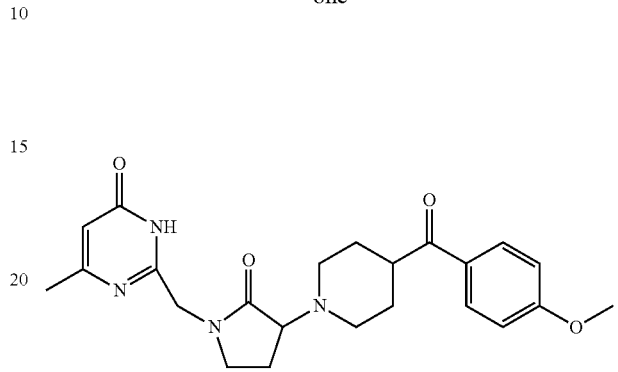

The title compound (73 mg, 47% yield) was prepared using a similar method to the one described in Example 21 from (E)-methyl but-2-enoate (0.044 mL, 0.47 mmol). $^1$H NMR (400 MHz, CDCl$_3$) δ 11.30 (s, 1H), 7.95 (d, J=9.0 Hz, 2H), 6.96 (d, J=9.0 Hz, 2H), 6.20 (s, 1H), 4.40 (s, 2H), 3.89 (s, 3H), 3.70 (d, J=9.0 Hz, 1H), 3.40-3.57 (m, 2H), 3.22-3.40 (m, 1H), 2.98-3.21 (br. s, 3H), 2.45-2.60 (br. s, 1H), 2.30-2.43 (br. s, 1H), 2.28 (s, 3H), 2.11-2.25 (br. s, 1H), 1.82-1.99 (br. s, 4H). HRMS calculated for C$_{23}$H$_{28}$N$_4$O$_4$ 425.2189. found (ESI, [M+H]$^+$), 425.2186.

Example 24

6-Ethyl-2-{3-[4-(4-methoxy-benzoyl)-piperidin-1-yl]-2-oxo-pyrrolidin-1-ylmethyl}-3H-pyrimidin-4-one

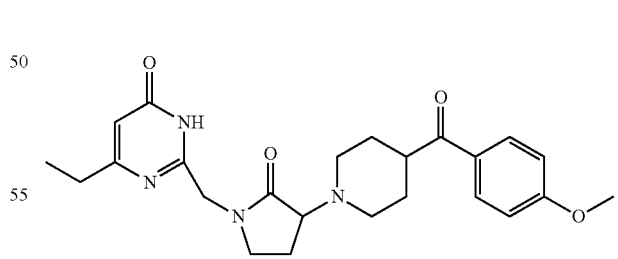

The title compound (64 mg, 40% yield) was prepared using a similar method to the one described in Example 21 from ethyl 3-oxopentanoate (0.067 mL, 0.47 mmol). $^1$H NMR (400 MHz, CDCl$_3$) δ 11.67 (s, 1H), 7.95 (d, J=9.0 Hz, 2H), 6.96 (d, J=8.5 Hz, 2H), 6.19 (s, 1H), 4.42 (s, 2H), 3.89 (s, 3H), 3.68 (t, J=8.3 Hz, 1H), 3.40-3.55 (m, 2H), 3.22-3.35 (br. s, 1H), 3.07-3.18 (br. s, 1H), 2.98-3.07 (br. s, 2H), 2.54 (q, J=7.5 Hz, 3H), 2.25-2.43 (m, 1H), 2.08-2.24 (br. s, 1H), 1.81-1.97 (br. s, 4H), 1.15-1.33 (m, 3H). HRMS calculated for C$_{24}$H$_{30}$N$_4$O$_4$ 439.2345. found (ESI, [M+H]$^+$), 439.2356.

Example 25

2-{3-[4-(4-Methoxy-benzoyl)-piperidin-1-yl]-2-oxo-pyrrolidin-1-ylmethyl}-5-methyl-3H-pyrimidin-4-one

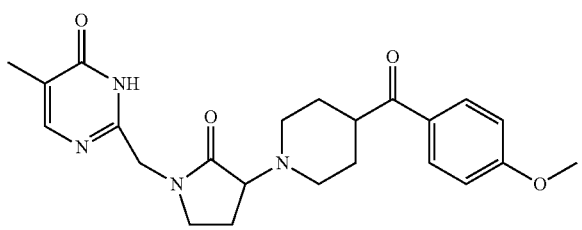

The title compound (96 mg, 62% yield) was prepared using a similar method to the one described in Example 21 from ethyl 2-methyl-3-oxopropanoate (0.057 mL, 0.47 mmol). $^1$H NMR (400 MHz, CDCl$_3$) δ 10.65 (s, 1H), 7.95 (d, J=9.0 Hz, 2H), 7.74 (s, 1H), 6.96 (d, J=8.5 Hz, 2H), 4.25-4.51 (m, 2H), 3.89 (s, 3H), 3.65 (t, J=8.5 Hz, 1H), 3.39-3.58 (m, 2H), 3.17-3.37 (m, 1H), 3.10 (d, J=10.5 Hz, 1H), 2.99 (br. s, 2H), 2.47 (br. s, 1H), 2.22-2.40 (m, 1H), 2.14 (dd, J=13.3, 8.3 Hz, 1H), 2.07 (s, 3H), 1.88 (br. s, 4H). HRMS calculated for C$_{23}$H$_{28}$N$_4$O$_4$ 425.2189. found (ESI, [M+H]$^+$), 425.2191.

Example 26

2-{3-[4-(4-Methoxy-benzoyl)-piperidin-1-yl]-2-oxo-pyrrolidin-1-ylmethyl}-5,6-dimethyl-3H-pyrimidin-4-one

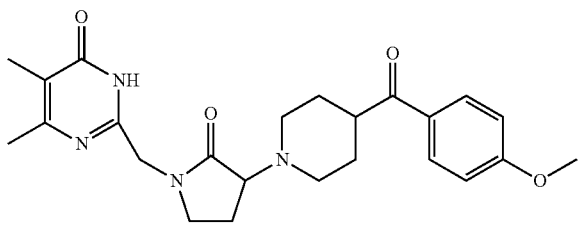

The title compound (40 mg, 19% yield) was prepared using a similar method to the one described in Example 21 from (Z)-ethyl 3-hydroxy-2-methylbut-2-enoate (0.081 mL, 0.56 mmol). $^1$H NMR (400 MHz, CDCl$_3$) δ 10.65 (s, 1H), 7.86 (d, J=9.1 Hz, 2H), 6.87 (d, J=9.1 Hz, 2H), 4.27 (s, 2H), 3.80 (s, 3H), 3.54 (t, J=8.6 Hz, 1H), 3.31-3.47 (m, 2H), 3.18 (ddd, J=9.5, 5.3, 4.9 Hz, 1H), 2.95-3.06 (m, 1H), 2.87-2.95 (m, 2H), 2.33-2.45 (m, 1H), 2.17-2.31 (m, 4H), 1.94-2.10 (m, 4H), 1.70-1.88 (m, 4H). HRMS calculated for C$_{24}$H$_{30}$N$_4$O$_4$ 439.2345. found (ESI, [M+H]$^+$), 439.2347.

Example 27

2-((3-(4-(4-methoxybenzoyl)piperidin-1-yl)-2-oxopyrrolidin-1-yl)methyl)cyclohepta[d]imidazol-4(3H)-one

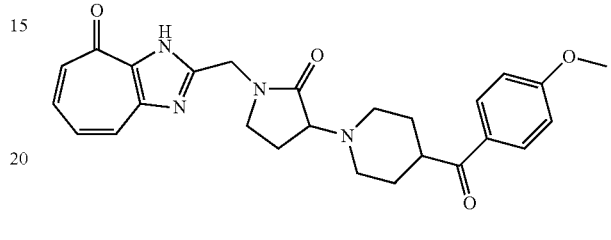

Toluene-4-sulfonic acid 7-oxo-cyclohepta-1,3,5-trienyl ester (0.33 mmol. 91 mg), 2-{3-[4-(4-methoxy-benzoyl)-piperidin-1-yl]-2-oxo-pyrrolidin-1-yl}-acetamidine (0.33 mmol, 130 mg) and tetrabutylammonium bromide (0.132 mmol, 42.4 mg) were added to a solution of 30% NaOH (13.1 mg, 1 mL) and toluene (5 mL) and stirred for 16 hours. The reaction was treated with an excess of brine and extracted with ethyl acetate (3×20 mL). The combined organic layers were concentrated in vacuo. The crude material was purified by preparative reverse-phase HPLC (300×50 mm) eluting with a gradient of 25-35% acetonitrile/water over 45 min., followed by lyophilization of the pure fractions provided the TFA salt of the title compound (23.6 mg, 14% yield). HRMS calculated for C$_{26}$H$_{28}$N$_4$O$_4$ 460.4375. found (ESI, [M+H]$^+$). found 461.2200. $^1$H NMR (400 MHz, MeOD) δ ppm 1.91-2.26 (m, 4H) 2.33-2.50 (m, 1H) 2.54-2.68 (m, 1H) 3.24-3.43 (m, 8H) 3.45-3.82 (m, 6H) 3.88 (s, 3H) 3.92-4.12 (m, 1H) 4.32-4.48 (m, 1H) 4.72-4.92 (m, 2H) 7.04 (d, J=9.03 Hz, 2H) 7.14-7.33 (m, 1H) 7.42-7.65 (m, 1H) 7.69-7.88 (m, 1H) 8.02 (d, J=9.03 Hz, 2H). HPLC (Novapak 150×3.9 mm C18 column: mobile phase: 10-90% acetonitrile/water with 0.1% TFA, at 2 mL/min over 5 min.) retention time=2.572 min.

Example 28

2-{(S)-3-[4-(4-Methoxy-3-methyl-benzoyl)-piperidin-1-yl]-2-oxo-pyrrolidin-1-ylmethyl}-3H-cycloheptaimidazol-4-one

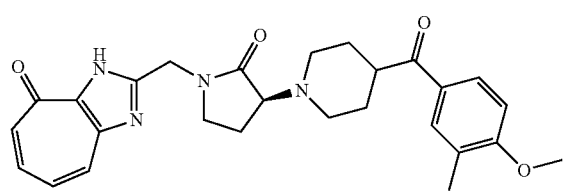 [SMILES: COc1ccc(C(=O)C2CCN([C@H]3CCN(Cc4nc5ccccc(=O)c5[nH]4)C3=O)CC2)cc1C]

Toluene-4-sulfonic acid 7-oxo-cyclohepta-1,3,5-trienyl ester (0.86 mmol. 236 mg), 2-{(S)-3-[4-(4-methoxy-3-methyl-benzoyl)-piperidin-1-yl]-2-oxo-pyrrolidin-1-yl}-acetamidine (0.86 mmol, 350 mg) and tetrabutylammonium bromide (0.34 mmol, 110 mg) were added to a solution of 30% NaOH (13.1 mg, 1 mL) and toluene (5 mL) and stirred for 16 hours. The reaction was treated with an excess of saturated ammonium chloride, diluted w/10% isopropanol/chloroform, washed with brine, dried, concentrated in vacuo. Chiral resolution of 2-((3-(4-(4-methoxybenzoyl)piperidin-1-yl)-2-oxopyrrolidin-1-yl)methyl)cyclohepta[d]imidazol-4(3H)-one (405 mg) via SFC chromatography on a AS-H column (60 g/min, 21×250 mm) eluting 40% IPA/0.2% DEA/$CO_2$ (v/v) afforded 21 mg of pure material. (21 mg, 9% yield). HRMS calculated for $C_{27}H_{30}N_4O_4$ 474.5646. found (ESI, [M+H]$^+$). found 475.2354. $^1$H NMR (400 MHz, CDCl$_3$-d) δ ppm 1.85 (d, 4H) 2.00-2.15 (m, 1H) 2.16-2.33 (m, 4H) 2.39-2.52 (m, 1H) 2.90-3.00 (m, 2H) 3.02-3.12 (m, 1H) 3.18-3.31 (br. s, 1H) 3.38-3.55 (m, 8H) 3.57-3.67 (m, 1H) 3.91 (s, 3H) 4.68-4.86 (m, 2H) 6.83-6.91 (m, 1H) 6.98-7.10 (m, 1H) 7.25-7.34 (m, 3H) 7.35-7.45 (m, 2H) 7.72-7.86 (m, 6H). HPLC (Novapak 150×3.9 mm C18 column: mobile phase: 10-90% acetonitrile/water with 0.1% TFA, at 2 mL/min over 5 min.) retention time=2.920 min.

Example 29

2-{(R)-3-[4-(4-Methoxy-3-methyl-benzoyl)-piperidin-1-yl]-2-oxo-pyrrolidin-1-ylmethyl}-3H-cycloheptaimidazol-4-one

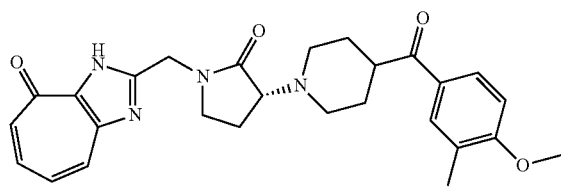 [SMILES: COc1ccc(C(=O)C2CCN([C@@H]3CCN(Cc4nc5ccccc(=O)c5[nH]4)C3=O)CC2)cc1C]

The title compound (18 mg) was prepared following the general procedures of Example 28 starting with 2-{(R)-3-[4-(4-methoxy-3-methyl-benzoyl)-piperidin-1-yl]-2-oxo-pyrrolidin-1-yl}-acetamidine (405 mg, 0.85 mmol). HRMS calculated for $C_{27}H_{30}N_4O_4$ 474.5646. found (ESI, [M+H]$^+$). found 475.2345. $^1$H NMR (400 MHz, CDCl$_3$-d) δ ppm 1.74-2.11 (m, 4H) 2.22-2.44 (m, 5H) 2.57 (d, J=8.03 Hz, 1H) 3.09 (d, J=6.53 Hz, 3H) 3.28-3.40 (m, 1H) 3.50 (t, J=8.28 Hz, 2H) 3.62-3.83 (m, 1H) 3.89-3.97 (m, 3H) 4.82 (br. s, 2H) 6.87 (d, J=8.53 Hz, 1H) 7.00-7.11 (m, 1H) 7.26-7.36 (m, 5H) 7.38-7.47 (m, 1H) 7.72-7.86 (m, 3H) HPLC (Novapak 150×3.9 mm C18 column: mobile phase: 10-90% acetonitrile/water with 0.1% TFA, at 2 mL/min over 5 min.) retention time=2.874 min.

Example 30

2-{(S)-3-[4-(4-Methoxy-benzoyl)-piperidin-1-yl]-2-oxo-pyrrolidin-1-ylmethyl}-3H-cycloheptaimidazol-4-one

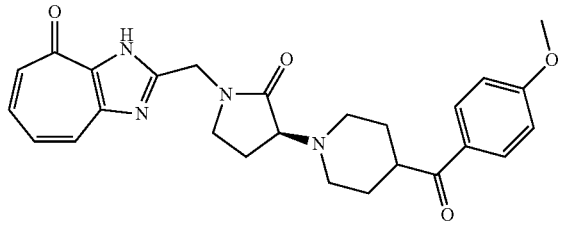 [SMILES: COc1ccc(C(=O)C2CCN([C@H]3CCN(Cc4nc5ccccc(=O)c5[nH]4)C3=O)CC2)cc1]

Chiral resolution of 2-((3-(4-(4-methoxybenzoyl)piperidin-1-yl)-2-oxopyrrolidin-1-yl)methyl)cyclohepta[d]imidazol-4(3H)-one (300 mg, 0.65 mmol) via SFC chromatography on a AS-H column (60 g/min, 21×250 mm) eluting 40% IPA/0.2% DEA/$CO_2$ (v/v) afforded 35 mg of pure material. HRMS calculated for $C_{26}H_{28}N_4O_4$ 460.5375. found (ESI, [M+H]$^+$) 461.2195. $^1$H NMR (400 MHz, MeOD) 1H NMR (400 MHz, chloroform-d) δ ppm 1.17-1.39 (br. s, 2H) 1.41-1.50 (m, 1H) 1.63-1.73 (m, 1H) 1.76-1.96 (br. s, 4H) 2.06-2.19 (m, 1H) 2.23-2.35 (m, 1H) 2.42-2.55 (m, 1H) 2.93-3.03 (m, 2H) 3.06-3.15 (m, 1H) 3.22-3.32 (m, 1H) 3.41-3.55 (m, 2H) 3.60-3.70 (m, 1H) 3.89 (s, 3H) 4.76-4.89 (m, 2H) 6.95 (d, J=9.03 Hz, 2H) 7.02-7.11 (m, 1H) 7.28 (s, 2H) 7.32-7.40 (m, 1H) 7.40-7.50 (m, 1H) 7.78 (d, J=10.54 Hz, 1H) 7.94 (d, J=8.53 Hz, 2H), analytical RP-HPLC (Novapak 150×3.9 mm C18 column: mobile phase: 10-90% acetonitrile/water with 0.1% TFA, at 2 mL/min over 5 min.) retention time=2.638 min.

Example 31

2-{(R)-3-[4-(4-Methoxy-benzoyl)-piperidin-1-yl]-2-oxo-pyrrolidin-1-ylmethyl}-3H-cycloheptaimidazol-4-one

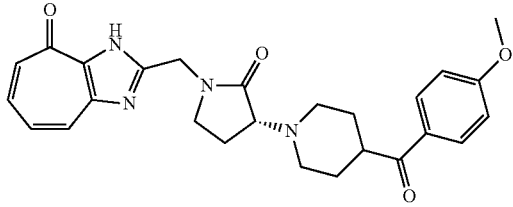 [SMILES: COc1ccc(C(=O)C2CCN([C@@H]3CCN(Cc4nc5ccccc(=O)c5[nH]4)C3=O)CC2)cc1]

Chiral resolution of 2-((3-(4-(4-methoxybenzoyl)piperidin-1-yl)-2-oxopyrrolidin-1-yl)methyl)cyclohepta[d]imidazol-4(3H)-one (300 mg) via SFC chromatography on a AS-H column (60 g/min, 21×250 mm) eluting 40% IPA/0.2% DEA/$CO_2$ (v/v) afforded 35 mg of pure material. HRMS calculated for $C_{26}H_{28}N_4O_4$ 460.5375. found (ESI, [M+H]$^+$) 461.2181. $^1$H NMR (400 MHz, MeOD) 1H NMR (400 MHz, chloroform-d) δ ppm 0.81-0.95 (m, 1H) 1.18-1.35 (m, 2H) 1.78-1.93 (m, 4H) 2.13 (dd, J=11.80, 7.28 Hz, 1H) 2.22-2.34 (m, 1H) 2.49 (d, J=3.51 Hz, 1H) 2.91-3.04 (br. s, 2H) 3.10 (d, J=10.54 Hz, 1H) 3.21-3.31 (m, 1H) 3.40-3.55 (m, 3H) 3.65 (t, J=8.78 Hz, 1H) 3.89 (s, 3H) 4.76-4.91 (m, 2H) 6.95 (d, J=9.03 Hz, 2H) 7.06 (dd, J=10.54, 8.53 Hz, 1H) 7.34-7.49 (m, 2H) 7.78 (d, J=11.04 Hz, 1H) 7.94 (d, J=8.53 Hz, 2H). Analytical RP-HPLC retention time=4.55 min Example 32

N-(5,6-dihydrothiazolo[2,3-c][1,2,4]triazol-3-yl)-2-(3-(4-(4-methoxybenzoyl)piperidin-1-yl)-2-oxopyrrolidin-1-yl)acetamide

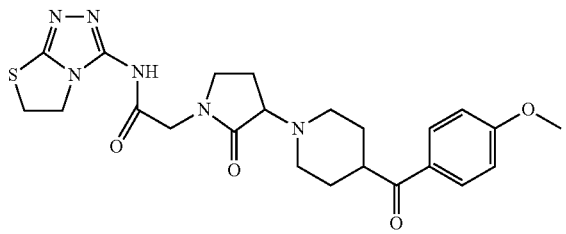 [SMILES: COc1ccc(C(=O)C2CCN(C3CCN(CC(=O)Nc4nnc5n4CCS5)C3=O)CC2)cc1]

A mixture of 500 mg of 76.5% pure 2-(3-(4-(4-methoxybenzoyl)piperidin-1-yl)-2-oxopyrrolidin-1-yl)acetic acid (382 mg, 1.061 mmol) and 5,6-dihydrothiazolo[2,3-c][1,2,4]triazol-3-amine hydrobromide (237 mg, 1.061 mmol) was stirred in diisopropylethylamine (0.741 mL, 549 mg, 4.25 mmol) and dichloromethane (10 mL) before addition of HATU reagent (444 mg, 1.161 mmol). The reaction was stirred over 45 hours at room temperature. A small amount of off-white solid was removed by filtration. The filtrate was eluted through a silica gel column with 0 to 15% methanol/dichloromethane, then 15% to 30%, followed by 30%. The fractions containing contaminated product were concentrated down and eluted through a second silica gel column with 5% to 12% methanol/dichloromethane gradient followed by 12% to afford the title compound (177 mg) as a white solid. Calculated mass for $C_{23}H_{28}N_6O_4S$=484.57. HR-MS [m/z, (M+H)$^+$]=485.1956. HPLC retention time=2.73 minutes (Agilent 1100 HPLC system; 3.0×100 nm 3 um C18 column; flow rate of 1.0 mL/min; gradient of 5-95% acetonitrile/water with 0.1% formic acid over 10 minutes). $^1$H NMR (400 MHz, DMSO-d$_6$) δ ppm 11.06 (br s, 1H), 7.94 (d, J=9.09 Hz, 2H), 7.03 (d, J=8.59 Hz, 2H), 3.92-4.21 (m, 6H), 3.83 (s, 3H), 3.39-3.51 (m, 1H), 3.21-3.37 (m, 3H), 2.99 (d, J=13.14 Hz, 1H), 2.64-2.84 (m, 2H), 2.28-2.42 (m, 1H), 2.03-2.18 (m, 1H), 1.85-2.02 (m, 1H), 1.65-1.78 (m, 2H), 1.44-1.60 (m, 2H).

Example 33

Peak 1 and

Example 34

Peak 2

N-(5,6-Dihydrothiazolo[2,3-c][1,2,4]triazol-3-yl)-2-(3-(4-(4-methoxybenzoyl)piperidin-1-yl)-2-oxopyrrolidin-1-yl)acetamide (166 mg, 0.343 mmol) was eluted through a SCF column (70 mL/min flow rate) with 60% CO$_2$ and 40% modifier (composed of 70% dichloromethane/ethanol and 0.2% diethylamine) to yield two enantiomerically enriched peaks N-(5,6-dihydrothiazolo[2,3-c][1,2,4]triazol-3-yl)-2-((S)-3-(4-(4-methoxybenzoyl)piperidin-1-yl)-2-oxopyrrolidin-1-yl)acetamide and N-(5,6-dihydrothiazolo[2,3-c][1,2,4]triazol-3-yl)-2-((R)-3-(4-(4-methoxybenzoyl)piperidin-1-yl)-2-oxopyrrolidin-1-yl)acetamide.

Peak 1 (54.5 mg), SFC retention time=3.87 minutes (Instrument: sfc_a-250; Column: Whelko (R,R); Mobile Phase: 40%(70% DCM/30% EtOH) 0.2% DEA).

Peak 2 (60 mg) SFC retention time=6.85 minutes (Instrument: sfc_a-250; Column: Whelko (R,R); Mobile Phase: 40%(70% DCM/30% EtOH) 0.2% DEA).

Example 35

N-([1,2,4]triazolo[4,3-a]pyridin-3-yl)-2-(3-(4-(4-methoxybenzoyl)piperidin-1-yl)-2-oxopyrrolidin-1-yl)acetamide

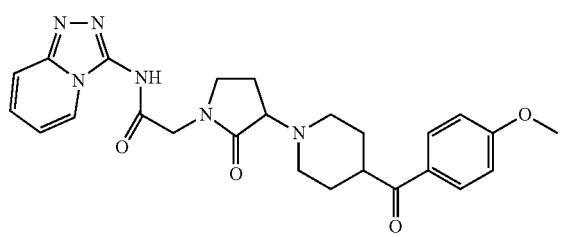 [SMILES: COc1ccc(C(=O)C2CCN(C3CCN(CC(=O)Nc4nnc5ccccn45)C3=O)CC2)cc1]

Following the general procedure of Example 32, the title compound (115 mg) was prepared from [1,2,4]triazolo[4,3-a]pyridin-3-amine (101 mg, 0.472 mmol). The reaction was run 1 hour at room temperature, 5.5 hours at 50° C., then 62 hours at room temperature before workup and purification. Calculated Mass for $C_{25}H_{28}N_6O_4$=476.53. HR-MS [m/z, (M+H)$^+$]=477.2269. HPLC retention time=2.70 minutes (Agilent 1100 HPLC system; 3.0×100 nm 3 um C18 column; flow rate of 1.0 mL/min; gradient of 5-95% acetonitrile/water with 0.1% formic acid over 10 minutes). $^1$H NMR (400 MHz, DMSO-d$_6$) δ ppm 11.06 (br s, 1H), 8.06 (d, J=7.07 Hz, 1H), 7.94 (d, J=8.59 Hz, 2H), 7.75 (d, J=9.09 Hz, 1H), 7.37-7.43 (m, 1H), 6.98-7.07 (m, 3H), 4.16-4.29 (m, 2H), 3.84 (s, 3H), 3.37-3.50 (m, 3H), 3.26-3.30 (m, 2H), 2.95-3.06 (m, 1H), 2.75-2.81 (m, 1H), 2.31-2.43 (m, 1H), 2.07-2.20 (m, 1H), 1.93-2.04 (m, 1H), 1.63-1.77 (m, 2H), 1.45-1.60 (m, 2H).

Example 36

2-(3-(4-(4-methoxybenzoyl)piperidin-1-yl)-2-oxopyrrolidin-1-yl)-N-(1-methyl-1H-tetrazol-5-yl)acetamide

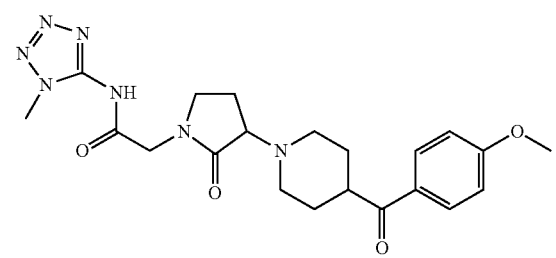 [SMILES: COc1ccc(C(=O)C2CCN(C3CCN(CC(=O)Nc4nnnn4C)C3=O)CC2)cc1]

Following the general procedure of Example 32, the title compound (21 mg) was prepared from 1-methyl-1H-tetrazol- 5-amine (12.7 mg, 0.128 mmol). The reaction was run 1 hour at room temperature followed at 50° C. Calculated Mass for $C_{21}H_{27}N_7O_4$=441.48. HR-MS [m/z, (M+H)$^+$]=442.2209. HPLC retention time=2.73 minutes (Agilent 1100 HPLC system; 3.0×100 nm 3 um C18 column; flow rate of 1.0 mL/min; gradient of 5-95% acetonitrile/water with 0.1% formic acid over 10 minutes). 1H NMR (400 MHz, chloroform-d) δ ppm 7.91 (d, J=8.08 Hz, 2H), 6.93 (d, J=8.08 Hz, 2H), 4.09-4.57 (m, 2H), 3.75-4.06 (m, 6H), 3.40-3.73 (m, 3H), 3.03-3.31 (m, 2H), 2.75-3.02 (m, 2H), 2.38-2.61 (m, 1H), 2.03-2.36 (m, 2H), 1.66-1.95 (m, 4H).

Example 37

N-(3,4-dihydro-2H-pyrano[2,3-d]pyridazin-5-yl)-2-(3-(4-(4-methoxybenzoyl)piperidin-1-yl)-2-oxopyrrolidin-1-yl)acetamide

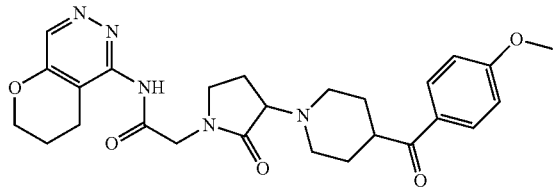 [SMILES: COc1ccc(C(=O)C2CCN(C3CCN(CC(=O)Nc4nncc5c4CCCO5)C3=O)CC2)cc1]

Following the general procedure of Example 32, the title compound (98.7 mg) was prepared from 3,4-dihydro-2H-pyrano[2,3-d]pyridazin-5-amine hydrobromide (186 mg, 0.521 mmol). Calculated Mass for $C_{26}H_{31}N_5O_5$=493.55. HR-MS [m/z, (M+H)$^+$]=494.2390. HPLC retention time=2.82 minutes (Agilent 1100 HPLC system; 3.0×100 nm 3 um C18 column; flow rate of 1.0 mL/min; gradient of 5-95% acetonitrile/water with 0.1% formic acid over 10 minutes). $^1$H NMR (400 MHz, chloroform-d) δ ppm 8.5-8.8 (br s, 1H), 7.88-7.98 (m, 2H), 6.89-7.00 (m, 2H), 4.28-4.39 (m, 2H), 4.19-4.28 (m, 2H), 3.88 (s, 3H), 3.57-3.66 (m, 1H), 3.42-3.58 (m, 2H), 3.19-3.32 (m, 1H), 3.08-3.19 (m, 1H), 2.93-3.06 (m, 2H), 2.59-2.72 (m, 2H), 2.46-2.59 (m, 1H), 2.22-2.37 (m, 1H), 2.10-2.22 (m, 1H), 1.99-2.10 (m, 2H), 1.78-1.97 (m, 4H).

Example 38

N-(isoxazolo[5,4-b]pyridin-3-yl)-2-(3-(4-(4-methoxybenzoyl)piperidin-1-yl)-2-oxopyrrolidin-1-yl) acetamide

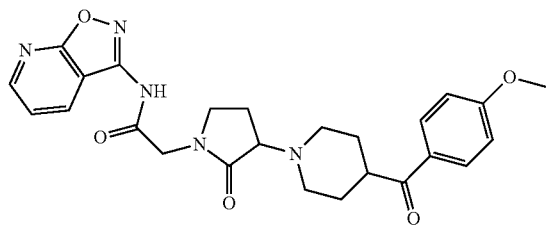 [SMILES: COc1ccc(C(=O)C2CCN(C3CCN(CC(=O)Nc4noc5ncccc45)C3=O)CC2)cc1]

Following the general procedure of Example 32, the title compound (23.9 mg) was prepared from isoxazolo[5,4-b]pyridin-3-amine (100 mg, 0.740 mmol). The reaction was run 1 hour at room temperature and 72 hours at 60° C. before workup and purification. Calculated Mass for $C_{25}H_{27}N_5O_5$=477.51. HR-MS [m/z, (M+H)$^+$]=478.2094. HPLC retention time=2.68 minutes (Agilent 1100 HPLC system; 3.0×100 nm 3 um C18 column; flow rate of 1.0 mL/min; gradient of 5-95% acetonitrile/water with 0.1% ammonium formate over 10 minutes). $^1$H NMR (400 MHz, DMSO-d$_6$) δ ppm 12.11-12.25 (br. s, 1H), 8.18 (dd, J=7.07, 2.53 Hz, 1H), 7.96 (d, J=8.59 Hz, 2H), 7.62-7.67 (m, 1H), 7.04 (d, J=8.59 Hz, 2H), 6.36 (t, J=6.82 Hz, 1H), 4.73-4.85 (m, 2H), 3.84 (s, 3H), 3.38-3.54 (m, 3H), 3.29-3.31 (m, 2H), 2.98-3.05 (m, 1H), 2.77-2.82 (m, 1H), 2.35-2.44 (m, 1H), 2.13-2.24 (m, 1H), 1.97-2.05 (m, 1H), 1.68-1.79 (m, 2H), 1.47-1.63 (m, 2H).

Biological Assays and Data

Biochemical Assay to Determine Compound Inhibition of TNKS Enzyme Activity

The human tankyrase 1 PARP catalytic domain, TNKS1P, was cloned into a pDONR221 vector using the Invitrogen Gateway Technology. This entry clone was then subcloned into the destination vector pDEST20 to obtain the N-terminal Glutathione S-transferase (GST)-tagged fusion protein. GST-TNKS1 P was then expressed in Sf21 cells using the Invitrogen baculovirus expression system (Invitrogen-Bac-to-Bac® Baculovirus Expression System, Version D). The protein was purified by a GSTrap column (GE Healthcare). The N-terminal GST-tagged tankyrase 2 protein PARP domain, TNKS2P, was cloned, expressed, and purified in a similar manner. Human PARP1 (Cat. No. 4668-100-01) and activated DNA (Cat. No. 4671-096-06) were purchased from Trevigen, Inc. PARP2 (Cat. No. ALX-201-064-C020) was purchased from Alexis Biochemical.

The autoparsylation activity of the TNKS 1/2 or PARP1/2 enzymes was measured by the liquid chromatography-mass spectrometry (LC/MS) detection of nicotinamide as readout. Compound activity in inhibiting the TNKS and PARP autoparsylation was evaluated by IC$_{50}$ measurements. In the compound screening assays, the reaction is composed of 5 μL of compound in 8-point serial dilutions with concentrations ranging from 0.0086 to 18.75 μM, 20 nM of purified enzyme, and 250 μM of p-NAD+ in the 1× Assay Buffer. After 60 min incubation at room temperature, the reactions were quenched by the addition of 10 μL of 5× quenching solution (20% formic acid and 500 nM [d]-nicotinamide in water). For the background control wells, 10 μL of the 5× quenching solution per well was added prior to the addition of p-NAD+. The % Inhibition was calculated as: (Control−Sample)/(Control−Background)*100. "Control" is the average value of 8 wells without compound; and "Background" is the average of 8 wells mixed with 5× quenching solution measured prior to initiation of the reaction.

Examples 1-38 were tested in one or more of the above enzymatic assays, the results of which are given in Table 1.

TABLE 1

| Example | TNKS2 AP IC$_{50}$ (μM) | TNKS1 AP IC$_{50}$ (μM) | PARP1 IC$_{50}$ (μm) | PARP2 Ic$_{50}$(μm) |
| --- | --- | --- | --- | --- |
| 1 | 0.081 ± 0.001 | 0.162 ± 0.004 | | |
| 2 | 0.015 ± 0.004 | 0.033 ± 0.007 | 9.3 ± 1.8 | 5.4 ± 0.4 |
| 3 | 0.0095 ± 0.0007 | 0.0128 ± 0.0026 | 21.0 ± 8.7 | 4.8 ± 0.6 |
| 4 | 0.60 ± 0.33 | 1.6 ± 1.2 | | |
| 5 | 0.015 ± 0.001 | 0.036 ± 0.001 | | |
| 6 | 0.025 ± 0.004 | 0.022 ± 0.004 | >19 | >19 |
| 7 | 0.083 ± 0.005 | 0.211 ± 0.063 | | |
| 8 | 0.141 ± 0.04 | 0.096 ± 0.028 | | |
| 9 | 0.023 ± 0.001 | 0.030 ± 0.002 | 16.6 ± 4.2 | 4.62 ± 0.95 |
| 10 | 0.006 ± 0.001 | 0.027 ± 0.001 | 23.6 ± 2.7 | 9.20 ± 2.2 |
| 11 | 0.017 ± 0.002 | 0.037 ± 0.005 | 37.4 ± 0.3 | 10.2 ± 4.2 |

TABLE 1-continued

| Example | TNKS2 AP IC$_{50}$ (µM) | TNKS1 AP IC$_{50}$ (µM) | PARP1 IC$_{50}$ (µm) | PARP2 Ic$_{50}$(µm) |
|---|---|---|---|---|
| 12 | 2.12 ± 0.05 | 5.34 ± 0.34 | | |
| 13 | 0.003 ± 0.001 | 0.006 ± 0.001 | 24 ± 3 | 4.0 ± 1.1 |
| 14 | 0.206 ± 0.02 | 0.711 ± 0.02 | | |
| 15 | 0.018 ± 0.002 | 0.033 ± 0.002 | | |
| 16 | <0.0086 | 0.012 ± 0.001 | | |
| 17 | 1.72 ± 0.12 | 3.85 ± 0.48 | | |
| 18 | 0.015 ± 0.001 | 0.046 ± 0.001 | | |
| 19 | 0.009 ± 0.001 | 0.024 ± 0.001 | | |
| 20 | 0.218 ± 0.002 | 0.483 ± 0.01 | | |
| 21 | 0.017 ± 0.002 | 0.034 ± 0.001 | 29.6 ± 2.8 | 10.7 ± 0.2 |
| 22 | 0.764 ± 0.056 | 1.50 ± 0.12 | | |
| 23 | 0.137 ± 0.022 | 0.286 ± 0.005 | | |
| 24 | 0.053 ± 0.005 | 0.115 ± 0.004 | >19 | >19 |
| 25 | 0.036 ± 0.006 | 0.072 ± 0.002 | >19 | >19 |
| 26 | 0.026 ± 0.001 | 0.047 ± 0.002 | >19 | >19 |
| 27 | 0.019 ± 0.001 | 0.036 ± 0.003 | | |
| 28 | 0.007 ± 0.001 | 0.0195 ± 0.0035 | 20.2 ± 1.5 | 2.9 ± 0.3 |
| 29 | 0.112 | 0.278 ± 0.05 | | |
| 30 | 0.005 ± 0.001 | 0.0095 ± 0.0007 | | |
| 31 | 0.39 ± 0.07 | 1.08 ± 0.01 | >19 | 10.1 ± 2.6 |
| 32 | 0.021 ± 0.001 | 0.043 ± 0.001 | >19 | 5.09 ± 0.12 |
| 33 | 0.374 ± 0.002 | 0.83 ± 0.02 | | |
| 34 | 0.016 ± 0.001 | 0.038 ± 0.001 | >19 | 6.3 ± 0.7 |
| 35 | 0.636 ± 0.036 | 2.47 ± 0.03 | | |
| 36 | 1.48 ± 0.02 | 3.08 ± 0.23 | | |
| 37 | 0.97 ± 0.06 | 3.01 ± 0.06 | | |
| 38 | 4.56 ± 0.04 | 6.5 ± 0.8 | | |

Cellular Reporter Gene Assay to Determine Compound Inhibition of Wnt Signaling Activity Compound activity in inhibiting Wnt ligand-induced signaling was measured using a Wnt-responsive Super-TOp-Flash (STF) luciferase reporter gene assay in HEK293 cells. On day 1 of the assay, cells were plated at a density of 8000 cells per well of 384-well plate in 25 µl medium containing 5% fetal bovine serum (FBS). On the second day, 20 Wnt3A condition medium (CM) produced from mouse L cells was added to the cells to induce Wnt signaling, followed by addition of 5 µL of compounds each well in 10-point serial dilution. On the third day, the luciferase activity was measured by the Bright-Glo™ Luciferase Assay System following manufacture's protocol (Promega, E2620). The Inhibition was calculated as: (Maximum Wnt-induced signaling−Sample)/(Maximum Wnt-induced signaling−Background)*100. "Maximum Wnt-induced signaling" is the STF signal level induced by 20% Wnt3A CM without compound; and "Background" is the STF signal level without the addition of Wnt3A CM or compound.

Cellular ELISA Assay to Determine Compound Effect on Stabilizing the Axin2 Protein Compound activity in stabilizing the Axin2 protein was measured by Sandwich Enzyme-Linked Immuosorbent (ELISA) assay in the colorectal cell line SW480. 30,000 SW480 cells were seeded per well in 96-well plate and incubated overnight prior to compound treatment. Cells were then treated with compounds in 6-point dilution starting at 10 µM for 24 hrs. Cells were then washed with 100 µL of cold Phosphate Buffer Saline (PBS), and lysed in 125 µl of cold 1× lysis buffer (Cell Signaling Technology, 9803) supplemented with Protease inhibitor (Roche, 11836170) and Phosphatase inhibitors (Sigma, P2850, P5726). For the ELISA assay, anti Axin-2 capture antibody (Strategic Diagnostics) antibody was diluted to a concentration of 1 µg/ml (1:1000) in Carbonate Coating buffer, pH 9.2 (Sigma, C3041-50CAP). 100µ of the diluted anti Axin-2 capture antibody per well was then used to coat the 96-well ELISA plate (Thermo Electron Corp., MicroLite 1 flat bottom plate #7571) overnight at 4° C. Plates were then washed three times with 300 µl/well of wash solution, PBST20 (PBS+0.05% Tween), and blocked with 300 µl/well 1% BSA/PBS (BSA, Millipore Probumin #82-045-1) for 1.5 hours at room temperature while shaking gently. After blocking, plates were then washed three times with 300 µl/well of wash solution. 100 µL of prepared SW480 cell lysate was then added to each well and incubated at room temperature for 2 hours while shaking gently. After washing, 100 µL of Biotinylated anti-Axin2 antibody (CST, 2151) was added to each well and incubated room temperature for 2 hours. 100 µL of Streptavidin-HRP (R&D systems, DY998) diluted 1:200 in 1% BSA/PBS was then added in each well and incubate for 30 mins at R/T in the dark. Signal was detected by Chemiluminescence (Pierce SuperSignal ELISA Femto #3704), and measured on PerkinElmer Wallac 1420 plate reader.

Cellular Proliferation Assay to Determine Compound Inhibition of Cancer Cell Growth Non-small lung cancer ABC-1 cells were plated at 5000 cells per well in 96-well plates and treated with 8 serial compound dilutions starting from 10 µM as the highest concentration. Viable cells were measured after 3 days of compound treatment using the CellTiter-Glo assay (Promega, G7570). Assay was performed following the manufacture protocol. Excel XLf it 4 was used for plotting of the growth curves and calculation of IC$_{50}$ values. % growth following compound treatment was calculated as: (treated sample/(DMSO control)*100. IC$_{50}$ values are concentrations of the compound at which cell growth is inhibited by 50%.

Examples 1-38 were tested in one or more of the above cellular assays, the results of which are given in Table 2.

TABLE 2

| Example | STF IC$_{50}$ (µM) | Axin AC$_{50}$ (µM) | ABC-1 IC$_{50}$ (µM) |
|---|---|---|---|
| 1 | 0.099 ± 0.011 | 0.239 ± 0.031 | 0.408 |
| 2 | 0.0013 ± 0.0008 | 0.0313 ± 0.0036 | 0.030 ± 0.005 |
| 3 | 0.0011 ± 0.0004 | 0.0063 ± 0.0013 | 0.012 ± 0.003 |
| 4 | 0.095 ± 0.011 | 0.31 ± 0.27 | 1.02 ± 0.34 |
| 5 | 0.017 ± 0.003 | 0.066 ± 0.001 | 0.156 |
| 6 | 0.0059 ± 0.0015 | 0.023 ± 0.003 | 0.043 |
| 7 | 0.054 ± 0.012 | 0.451 ± 0.068 | 1.47 |
| 8 | 0.018 ± 0.004 | 0.078 ± 0.013 | 0.133 |
| 9 | 0.003 ± 0.003 | 0.052 ± 0.004 | 0.060 |
| 10 | 0.010 ± 0.001 | 0.257 ± 0.067 | 0.291 |
| 11 | 0.005 ± 0.005 | 0.132 ± 0.022 | 0.301 |
| 12 | 0.62 ± 0.09 | >10 | >10 |
| 13 | 0.0012 ± 0.001 | 0.0021 ± 0.0001 | 0.003 |
| 14 | 0.031 ± 0.003 | 0.128 ± 0.13 | 0.149 |
| 15 | <0.0005± | 0.016 ± 0.001 | 0.043 |
| 16 | 0.0017 ± 0.0002 | 0.007 ± 0.001 | 0.082 |
| 17 | 0.396 ± 0.010 | 1.79 ± 0.14 | 2.0 ± 0.9 |
| 18 | 0.0056 ± 0.0007 | 0.051 ± 0.007 | 0.099 |
| 19 | 0.00080 ± 0.00005 | 0.021 ± 0.001 | 0.037 |
| 20 | 0.0173 ± 0.002 | 0.203 ± 0.018 | 0.212 |
| 21 | 0.00110 ± 0.00017 | 0.007 ± 0.002 | 0.018 |
| 22 | 0.39 ± 0.19 | | |
| 23 | 0.056 ± 0.033 | 0.227 ± 0.025 | 0.489 |
| 24 | 0.0104 ± 0.0023 | 0.104 ± 0.015 | 0.183 |
| 25 | 0.0034 ± 0.0015 | 0.046 ± 0.003 | 0.117 |
| 26 | 0.0041 ± 0.0021 | 0.021 ± 0.003 | 0.043 |
| 27 | 0.00040 ± 0.0003 | 0.0032 ± 0.0001 | 0.0015 |
| 28 | 0.0015 ± 0.0005 | 0.00046 ± 0.0002 | 0.0008 ± 0.0009 |
| 29 | 0.014 ± 0.004 | 0.009 ± 0.001 | 0.010 |
| 30 | 0.0011 ± 0.0001 | 0.00060 ± 0.0001 | 0.00086 ± 0.0001 |
| 31 | 0.065 ± 0.014 | 0.089 ± 0.002 | 0.085 |
| 32 | 0.0059 ± 0.0089 | 0.131 ± 0.008 | 0.076 |
| 33 | 0.379 ± 0.067 | 1.34 ± 0.11 | 1.61 |
| 34 | 0.012 | 0.078 ± 0.006 | 0.049 |
| 35 | 0.94 ± 0.07 | 1.89 ± 0.16 | 2.63 |
| 36 | 7.6 ± 0.8 | | >10 |
| 37 | 0.396 ± 0.026 | | 2.23 |
| 38 | 2.03 ± 0.18 | | 7.90 |

What is claimed is:

1. A compound according to formula (I)

(I)

wherein:
$R^1$ is $R^2$ or $R^2$—NHC(O)—;
$R^2$ is phenyl optionally substituted with one or two substituents each independently selected from the group consisting of: halo, OH, CN, $NO_2$, $C_{1-6}$ alkyl, $C_{1-6}$ alkoxy, $C_{1-6}$ haloalkyl, $C(O)R^a$, $COOR^a$, $NR^aR^b$, $NHC(O)R^a$, and $C(O)NR^aR^b$;
or
$R^2$ is a 5 membered heteroaryl having one to four heteroatoms selected from the group consisting of N, O, and S, or $R^2$ is a 6 membered heteroaryl having one or two N, said 5 and 6 membered heteroaryl rings being optionally substituted with one to three substituents each independently selected from the group consisting of: halo, oxo, OH, CN, $NO_2$, $C_{1-6}$ alkyl, $C_{1-6}$ alkoxy, $C_{1-6}$ haloalkyl, $C(O)R^a$, $COOR^a$, $NR^aR^b$, $NHC(O)R^a$, and $C(O)NR^aR^b$;
or
$R^2$ is an 8-10 membered bicyclic heteroaryl having 3 or 4 heteroatoms selected from the group consisting of N, O, and S,
said 8-10 membered heteroaryl being optionally substituted with one to three substituents each independently selected from the group consisting of:
(a) halo,
(b) oxo,
(c) OH,
(d) CN,
(e) $NO_2$,
(f) $C_{1-6}$alkyl optionally substituted with one hydroxy or one $C_{1-6}$ alkoxy,
(g) $C_{1-6}$ alkoxy,
(h) $C_{1-6}$ haloalkyl,
(i) $C(O)R^a$,
(j) $COOR^a$,
(k) $NR^aR^b$,
(l) $NHC(O)R^a$, and
(m) $C(O)NR^aR^b$;
$R^3$ is H and $R^4$ is phenyl optionally substituted with one to three substituents each independently selected from the group consisting of: halo, OH, CN, $NO_2$, $C_{1-6}$alkyl, $C_{1-6}$ alkoxy, $C_{1-6}$ haloalkyl, $C(O)R^a$, $COOR^a$, $NR^aR^b$, $NHC(O)R^a$, and $C(O)NR^aR^b$;
or
$R^3$ and $R^4$ together with the atoms to which they are attached form optionally substituted indan-1-one, said indan-1-one is attached to the piperidine ring of formula (I) through spiro carbon 4 and is optionally substituted with one to three substituents each independently selected from the group consisting of: halo and $C_{1-6}$ alkoxy;
$R^a$ is H or $C_{1-6}$ alkyl;
$R^b$ is H or $C_{1-6}$ alkyl; and
n is 1 or 2; or a pharmaceutically acceptable salt thereof.

2. The compound according to claim 1 having the following formula (II)

or a pharmaceutically acceptable salt thereof.

3. The compound according to claim 1 wherein $R^3$ is H; or a pharmaceutically acceptable salt thereof.

4. The compound according to claim 1 wherein $R^4$ is optionally substituted phenyl; or a pharmaceutically acceptable salt thereof.

5. The compound according to claim 4 wherein $R^4$ is substituted phenyl; or a pharmaceutically acceptable salt thereof.

6. The compound according to claim 5 wherein $R^4$ is phenyl substituted by one or two substituents each independently selected from the group consisting of halo, $C_{1-6}$ alkyl, and $C_{1-6}$ alkoxy; or a pharmaceutically acceptable salt thereof.

7. The compound according to claim 1 wherein $R^3$ and $R^4$ together with the atoms to which they are attached form optionally substituted indan-1-one; or a pharmaceutically acceptable salt thereof.

8. The compound according to claim 1 wherein n is 1; or a pharmaceutically acceptable salt thereof.

9. The compound according to claim 1 wherein n is 2; or a pharmaceutically acceptable salt thereof.

10. The compound according to claim 1 wherein $R^1$ is $R^2$; or a pharmaceutically acceptable salt thereof.

11. The compound according to claim 1 wherein $R^2$ is optionally substituted phenyl; or a pharmaceutically acceptable salt thereof.

12. The compound according to claim 1 wherein $R^2$ is an optionally substituted 5 or 6 membered heteroaryl; or a pharmaceutically acceptable salt thereof.

13. The compound according to claim 1 wherein $R^2$ is an optionally substituted 8-10 membered bicyclic heteroaryl; or a pharmaceutically acceptable salt thereof.

14. The compound according to claim 1 wherein $R^2$ is (a)

(b)

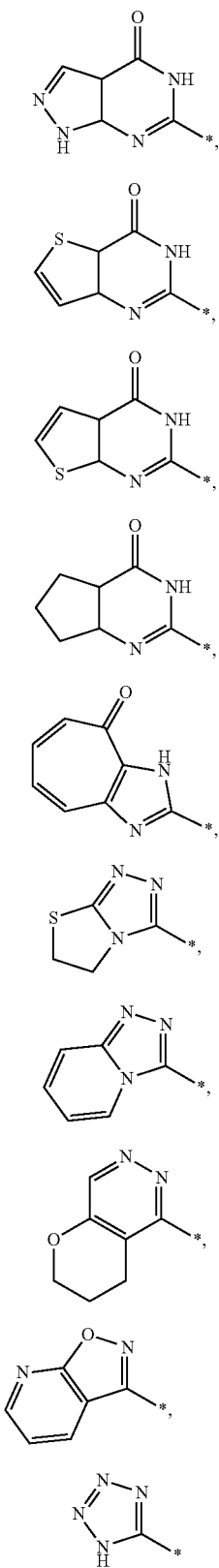

wherein each of (a)-(1) is optionally substituted with one or two substituents each independently selected from the group consisting of halo, OH, CN, NO$_2$, C$_{1-6}$ alkyl, C$_{1-6}$ alkoxy, C$_{1-6}$ haloalkyl, C(O)R$^a$, COOR$^a$, NR$^a$R$^b$, NHC(O)R$^a$, and C(O)NR$^a$R$^b$; or a pharmaceutically acceptable salt thereof.

15. The compound according to claim 1 which is:
2-Chloro-6-{3-[4-(4-methoxy-benzoyl)-piperidin-1-yl]-2-oxo-pyrrolidin-1-ylmethyl}-benzonitrile;
2-{3-[4-(4-Methoxy-benzoyl)-piperidin-1-yl]-2-oxo-pyrrolidin-1-ylmethyl}-3,5,7,8-tetrahydro-pyrano[4,3-d]pyrimidin-4-one;
2-{(R)-3-[4-(4-Methoxy-benzoyl)-piperidin-1-yl]-2-oxo-pyrrolidin-1-ylmethyl}-3,5,7,8-tetrahydro-pyrano[4,3-d]pyrimidin-4-one;
2-Chloro-5-((3-(4-(4-methoxybenzoyl)piperidin-1-yl)-2-oxopyrrolidin-1-yl)methyl)benzonitrile;
6-{3-[4-(4-Methoxy-benzoyl)-piperidin-1-yl]-2-oxo-pyrrolidin-1-ylmethyl}-1-methyl-1,3a,5,7a-tetrahydro-pyrazolo[3,4-d]pyrimidin-4-one;
2-{3-[4-(4-Methoxy-benzoyl)-piperidin-1-yl]-2-oxo-pyrrolidin-1-ylmethyl}-4a,7a-dihydro-3H-thieno[3,2-d]pyrimidin-4-one;
2-{3-[4-(4-Methoxy-benzoyl)-piperidin-1-yl]-2-oxo-pyrrolidin-1-ylmethyl}-6-methyl-4a,7a-dihydro-3H-thieno[2,3-d]pyrimidin-4-one;
2-{3-[4-(4-Chloro-benzoyl)-piperidin-1-yl]-2-oxo-pyrrolidin-1-ylmethyl}-3,5,7,8-tetrahydro-pyrano[4,3-d]pyrimidin-4-one;
2-{3-[4-(4-Fluoro-benzoyl)-piperidin-1-yl]-2-oxo-pyrrolidin-1-ylmethyl}-3,5,7,8-tetrahydro-pyrano[4,3-d]pyrimidin-4-one;
2-{(S)-3-[4-(4-Fluoro-benzoyl)-piperidin-1-yl]-2-oxo-pyrrolidin-1-ylmethyl}-3,5,7,8-tetrahydro-pyrano[4,3-d]pyrimidin-4-one;
2-{(R)-3-[4-(4-Fluoro-benzoyl)-piperidin-1-yl]-2-oxo-pyrrolidin-1-ylmethyl}-3,5,7,8-tetrahydro-pyrano[4,3-d]pyrimidin-4-one;
2-{(R)-3-[4-(4-Methoxy-3-methyl-benzoyl)-piperidin-1-yl]-2-oxo-pyrrolidin-1-ylmethyl}-3,5,7,8-tetrahydro-pyrano[4,3-d]pyrimidin-4-one;
2-((3-(5-methoxy-1-oxo-1,3-dihydrospiro[indene-2,4'-piperidine]-1'-yl)-2-oxopyrrolidin-1-yl)methyl)-7,8-dihydro-3H-pyrano[4,3-d]pyrimidin-4(5H)-one;
(S)-2-((3-(5-methoxy-1-oxo-1,3-dihydrospiro[indene-2,4'-piperidine]-1'-yl)-2-oxopyrrolidin-1-yl)methyl)-7,8-dihydro-3H-pyrano[4,3-d]pyrimidin-4(5H)-one;
(R)-2-((3-(5-methoxy-1-oxo-1,3-dihydrospiro[indene-2,4'-piperidine]-1'-yl)-2-oxopyrrolidin-1-yl)methyl)-7,8-dihydro-3H-pyrano[4,3-d]pyrimidin-4(5H)-one;
2-[4-(4-Methoxy-benzoyl)-2'-oxo-[1,3']bipiperidinyl-1'-ylmethyl]-3,5,7,8-tetrahydro-pyrano[4,3-d]pyrimidin-4-one;
2-[(S)-4-(4-Methoxy-benzoyl)-2'-oxo-[1,3']bipiperidinyl-1'-ylmethyl]-3,5,7,8-tetrahydro-pyrano[4,3-d]pyrimidin-4-one;
2-[(R)-4-(4-Methoxy-benzoyl)-2'-oxo-[1,3']bipiperidinyl-1'-ylmethyl]-3,5,7,8-tetrahydro-pyrano[4,3-d]pyrimidin-4-one;
2-((3-(4-(4-methoxybenzoyl)piperidin-1-yl)-2-oxopyrrolidin-1-yl)methyl)-6,7-dihydro-3H-cyclopenta[d]pyrimidin-4(5H)-one;
2-{3-[4-(4-Methoxy-benzoyl)-piperidin-1-yl]-2-oxo-pyrrolidin-1-ylmethyl}-3H-pyrimidin-4-one;
2-{3-[4-(4-Methoxy-benzoyl)-piperidin-1-yl]-2-oxo-pyrrolidin-1-ylmethyl}-6-methyl-3H-pyrimidin-4-one;
6-Ethyl-2-{3-[4-(4-methoxy-benzoyl)-piperidin-1-yl]-2-oxo-pyrrolidin-1-ylmethyl}-3H-pyrimidin-4-one;
2-{3-[4-(4-Methoxy-benzoyl)-piperidin-1-yl]-2-oxo-pyrrolidin-1-ylmethyl}-5-methyl-3H-pyrimidin-4-one;

2-{3-[4-(4-Methoxy-benzoyl)-piperidin-1-yl]-2-oxo-pyrrolidin-1-ylmethyl}-5,6-dimethyl-3H-pyrimidin-4-one;

2-((3-(4-(4-methoxybenzoyl)piperidin-1-yl)-2-oxopyrrolidin-1-yl)methyl)cyclohepta[d]imidazol-4(3H)-one;

2-{(R)-3-[4-(4-Methoxy-3-methyl-benzoyl)-piperidin-1-yl]-2-oxo-pyrrolidin-1-ylmethyl}-3H-cycloheptaimidazol-4-one;

2-{(S)-3-[4-(4-Methoxy-benzoyl)-piperidin-1-yl]-2-oxo-pyrrolidin-1-ylmethyl}-3H-cycloheptaimidazol-4-one;

2-{(R)-3-[4-(4-Methoxy-benzoyl)-piperidin-1-yl]-2-oxo-pyrrolidin-1-ylmethyl}-3H-cycloheptaimidazol-4-one;

N-(5,6-dihydrothiazolo[2,3-c][1,2,4]triazol-3-yl)-2-(3-(4-(4-methoxybenzoyl)piperidin-1-yl)-2-oxopyrrolidin-1-yl)-acetamide;

N-(5,6-Dihydro-thiazolo[2,3-c][1,2,4]triazol-3-yl)-2-{(S)-3-[4-(4-methoxy-benzoyl)-piperidin-1-yl]-2-oxo-pyrrolidin-1-yl}-acetamide;

N-(5,6-Dihydro-thiazolo[2,3-c][1,2,4]triazol-3-yl)-2-{(R)-3-[4-(4-methoxy-benzoyl)-piperidin-1-yl]-2-oxo-pyrrolidin-1-yl}-acetamide;

N-([1,2,4]triazolo[4,3-a]pyridin-3-yl)-2-(3-(4-(4-methoxybenzoyl)piperidin-1-yl)-2-oxopyrrolidin-1-yl)acetamide;

2-(3-(4-(4-methoxybenzoyl)piperidin-1-yl)-2-oxopyrrolidin-1-yl)-N-(1-methyl-1H-tetrazol-5-yl)acetamide;

N-(3,4-dihydro-2H-pyrano[2,3-d]pyridazin-5-yl)-2-(3-(4-(4-methoxybenzoyl)piperidin-1-yl)-2-oxopyrrolidin-1-yl)acetamide; or N-Isoxazolo[5,4-b]pyridin-3-yl-2-{3-[4-(4-methoxy-benzoyl)-piperidin-1-yl]-2-oxo-pyrrolidin-1-yl}-acetamide; or a pharmaceutically acceptable salt thereof.

16. A compound which is 2-{(S)-3-[4-(4-methoxy-benzoyl)-piperidin-1-yl]-2-oxo-pyrrolidin-1-ylmethyl}-3,5,7,8-tetrahydro-pyrano[4,3-d]pyrimidin-4-one having the following formula

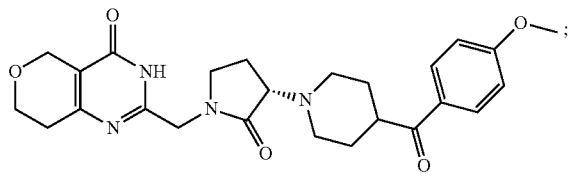 [SMILES: COc1ccc(C(=O)C2CCN([C@H]3CCN(Cc4nc5c(c(=O)[nH]4)COCC5)C3=O)CC2)cc1]

or a pharmaceutically acceptable salt thereof.

17. A compound which is 2-{(S)-3-[4-(4-methoxy-3-methyl-benzoyl)-piperidin-1-yl]-2-oxo-pyrrolidin-1-ylmethyl}-3,5,7,8-tetrahydro-pyrano[4,3-d]pyrimidin-4-one having the following formula

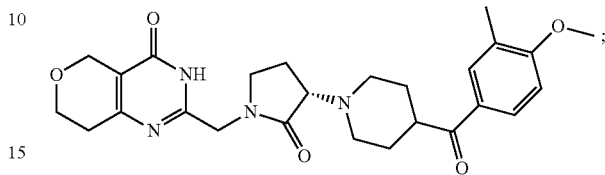

or a pharmaceutically acceptable salt thereof.

18. A compound which is 2-{(S)-3-[4-(4-methoxy-3-methyl-benzoyl)-piperidin-1-yl]-2-oxo-pyrrolidin-1-ylmethyl}-3H-cycloheptaimidazol-4-one having the following formula

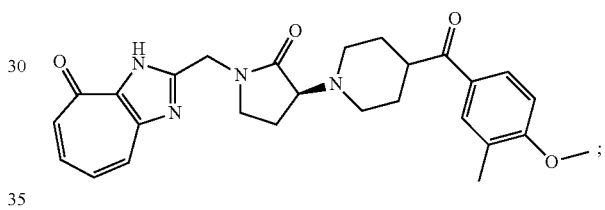

or a pharmaceutically acceptable salt thereof.

19. A pharmaceutical composition comprising a compound according to claim 1 or a pharmaceutically acceptable salt thereof and a pharmaceutically acceptable excipient.

20. A method for the treatment of cancer comprising administration of an effective amount of a compound according to claim 1 or a pharmaceutically acceptable salt thereof to a subject in need thereof.

* * * * *